US005871745A

United States Patent [19]
Perron et al.

[11] Patent Number: 5,871,745
[45] Date of Patent: Feb. 16, 1999

[54] MULTIPLE SCLEROSIS RELATED VIRUS

[75] Inventors: Herve Perron, Grenoble; Francois Mallet; Bernard Mandrand, both of Villeurbanne; Frederic Bedin, Lyons; Frederic Beseme, Villefontaine, all of France

[73] Assignee: Bio Merieux, Marcy l'Etoile, France

[21] Appl. No.: 471,969

[22] Filed: Jun. 6, 1995

Related U.S. Application Data

[62] Division of Ser. No. 384,137, Feb. 6, 1995.

[30] Foreign Application Priority Data

| Feb. 4, 1994 | [FR] | France | 94 01529 |
| Feb. 4, 1994 | [FR] | France | 94 01530 |
| Feb. 4, 1994 | [FR] | France | 94 01531 |
| Feb. 4, 1994 | [FR] | France | 94 01532 |
| Nov. 24, 1994 | [FR] | France | 94 14322 |
| Dec. 23, 1994 | [FR] | France | 94 15810 |

[51] Int. Cl.⁶ ............................ A61K 39/21; C07K 1/00
[52] U.S. Cl. ............................ 424/207.1; 424/187.1; 424/204.1; 424/185.1; 536/23.72; 530/350; 530/387.1
[58] Field of Search ............................ 530/387.1, 350; 536/23.72; 424/187.1, 207.1, 204.1, 185.1

[56] References Cited

U.S. PATENT DOCUMENTS

| 4,311,686 | 1/1982 | Angers et al. . |
| 4,346,074 | 8/1982 | Gilmour et al. . |
| 4,388,298 | 6/1983 | Nazerian et al. . |
| 4,396,600 | 8/1983 | Messineo et al. . |
| 4,520,113 | 5/1985 | Gallo et al. . |
| 4,647,773 | 3/1987 | Gallo et al. . |
| 4,708,818 | 11/1987 | Montagnier et al. . |
| 4,900,553 | 2/1990 | Silver et al. . |
| 5,158,976 | 10/1992 | Rosenburg et al. . |
| 5,219,837 | 6/1993 | Cohen et al. . |
| 5,225,352 | 7/1993 | Zanetta et al. . |
| 5,585,262 | 12/1996 | Perron et al. . |

FOREIGN PATENT DOCUMENTS

| 0 222 310 | 5/1987 | European Pat. Off. . |
| 0 326 395 | 8/1989 | European Pat. Off. . |
| 93/07259 | 4/1993 | WIPO . |
| 93/20188 | 10/1993 | WIPO . |
| WO 93/23550 | 11/1993 | WIPO . |
| WO 94/28138 | 12/1994 | WIPO . |

OTHER PUBLICATIONS

S. Haahr et al., "Is Multiple Sclerosis Caused by a Dual Infection with Retrovirus and Epstein–Barr Virus?", *Neuroepidemiology*, vol. 11, pp. 299–303, (1992).

G. La Mantia et al., "Identification of New Human Repetitive Sequences: Characterization of the Corresponding cDNAs and their Expression in Embryonal Carcinoma Cells", *Nucleic Acids Research*, vol. 17, No. 15, 5913–5922, (1989).

J. Merregaert et al., "Nucleotide Sequence of a Radiation Leukemia Virus Genome", *Virology*, vol. 158, No. 1, pp. 88–102, (1987).

Perron et al., "Retrovirus Isolation from Patients with Multiple Sclerosis: Epiphenomenon or Causative Factor?", *AIDS Research and Human Retroviruses*, vol. 8, No. 5, May 1992, p. 922.

Norby, "Viral Antibodies in Multiple Sclerosis", *Prog. Med. Virol.*, vol. 24 1978, pp. 1–39.

Johnson, "Viral Aspects of Multiple Sclerosis", *Handbook of Clinical Neurology*, vol. 3(47): Demyelinating Diseases, 1985, pp. 319–336.

Cook et al., "Multiple Sclerosis and Distemper in Iceland 1966–1978", *Acta Neurol. Scandinav.* 61, 1980, pp. 244–251.

Rosati et al. "Incidence of Multiple Sclerosis in the Town of Sassari, Sardina, 1965 to 1985: Evidence for Increasing Occurrence of the Disease", *Neurology* 38 (Mar. 1988), pp. 384–388.

Riise et al., "Clustering of Residence of Multiple Sclerosis Patients at Age 13 to 20 Years in Hordaland, Norway", *Am J Epidermiol* 1991, vol. 133, No. 9, pp. 932–939.

Elian et al., "Multiple Sclerosis Among United Kingdom–Born Children of Immigrants from the Indian Subcontinent, Africa and the West Indies", *J Neurol Neurosurg Psychiat*, 1990; 53, pp. 906–911.

Lisak et al., "In Vitro Cell–Mediated Immunity of Cerebrospinal–Fluid Lymphocytes to Myelin Basic Protein in Primary Demyelinating Diseases", *New Engl. J. Med.* 1977, vol. 297, No. 16, pp. 850–953.

Lassmann et al., "Chronic Relapsing Experimental Allergic Encephalomyelitis", *Arch. Neurol.*, 1979, vol. 36, Aug. 1979, pp. 490–497.

Hirayama et al., "Serum–Mediated Oligodendrocyte Cytotoxicity in Multiple Sclerosis Patients and Controls", *Neurology* 1986, vol. 36, pp. 276–278.

Warren et al., "Diagnostic Value of Cerebrospinal Fluid Anti–Myelin Basic Protein in Patients with Multiple Sclerosis", *Ann. Neurol.*, vol. 20, No. 1, July 1986, pp. 20–25.

Suzumura et al., "Serum Cytotoxicity to Oligodendrocytes in Multiple Sclerosis and Controls: Assessment by $^{51}$Cr Release Assay", *J. Neuroimmunol.*, 11 (1986), pp. 137–147.

(List continued on next page.)

Primary Examiner—Marian C. Knode
Assistant Examiner—Ali R. Salimi
Attorney, Agent, or Firm—Oliff & Berridge, PLC

[57] ABSTRACT

Composition including two pathogenic and/or infective agents associated with multiple sclerosis, namely a first agent which consists of a human virus possessing reverse transcriptase activity and related to a family of endogenous retroviral elements, or a variant of the virus, and a second agent, or a variant of the second agent, these two pathogenic and/or infective agents originating from the same viral strain chosen from the strains designated, respectively, POL-2 deposited with the ECACC on Jul. 22, 1992 under Accession Number V92072202 and MS7PG deposited with the ECACC on Jan. 8, 1993 under Accession Number V93010816, and from their variant strains.

10 Claims, 22 Drawing Sheets

OTHER PUBLICATIONS

Johnson et al., "Quantitation of the Myelin–Associated Glycoprotein in Human Nervous Tissue from Controls and Multiple Sclerosis Patients", *J. Neurochem.*, vol. 46, No. 4, 1986, pp. 1086–1093.

James, "Multiple Sclerosis or Blood–Brain Barrier Disease", *The Lancet,* Jan. 7, 1989, p. 46.

Rudge, "Does a Retrovirally Encoded Superantigen Cause Multiple Sclerosis?", *J. Neurology Neurosurgery & Psychiatry* 1991, vol. 54, pp. 853–855.

Gessain et al., "Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *J. Infect. Disease,* vol. 157, No. 6, Jun. 1988, pp. 1226–1234.

Koprowski et al., "Multiple Sclerosis and Human T–Cell Lymphotropic Retroviruses", *Nature,* vol. 318, Nov. 1985, pp. 154–160.

Ohta et al., "Sera From Patients with Multiple Sclerosis React with Human T Cell Lymphotropic Virus–I Gag Proteins but Not ENV Proteins–Western Blotting Analysis", *J. Immun.,* vol. 137, Dec. 1, 1986, pp. 3440–3443.

Reddy et al., "Amplification and Molecular Cloning of HTLV–I Sequences from DNA of Multiple Sclerosis Patients", *Science*, vol. 243, 27 Jan. 1989, pp. 529–533.

Greenberg et al., "Detection of Sequences Homologous to Human Retroviral DNA in Multiple Sclerosis by Gene Amplification", *Proc. Natl. Acad. Sci. USA,* vol. 86, Apr. 1989, pp. 2878–2882.

Richardson et al., "PCR Analysis of DNA from Multiple Sclerosis Patients for the Presence of HTLV–I", *Science,* vol. 246, 10 Nov. 1989, pp. 821–824.

Hauser et al., "Analysis of Human T–Lymphotropic Virus Sequences in Multiple Sclerosis Tissue", *Nature,* vol. 322, 10 Jul. 1986, pp. 176–177.

Karpas et al., "Lack of Evidence for Involvement of Known Human Retroviruses in Multiple Sclerosis", *Nature,* vol. 322, 10 Jul. 1986, pp. 177–178.

Perron et al., "Leptomeningeal Cell Line from Multiple Sclerosis with Reverse Transcriptase Activity and Viral Particles", *Res. Virol.,* 1989, 140, pp. 551–561.

Perron et al., "Isolations of an Unknown Retrovirus from CSF, Blood and Brain Cells of Patients with Multiple Sclerosis", in *Current Concepts in Multiple Sclerosis,* Wietholter et al., eds., 1991, Elsevier publ., pp. 111–116.

H. Perron et al., "Isolation of Retrovirus from Patients with Multiple Sclerosis", *The Lancet,* vol. 337, Apr. 6, 1991, pp. 862–864.

Perron et al., Herpes Simplex Virus ICP0 and ICP4 Immediate Early Proteins Strongly Enhance Expression of a Retrovirus Harboured by a Leptomeningeal Cell Line from a Patient with Multiple Sclerosis, *J. Gen. Virol.,* vol. 74, 1993, pp. 65–72.

Huang, "Defective Interfering Viruses", *Fundamental Virology,* Fields et al., eds., 1986, pp. 101–117.

Nielsen et al., "Sequence–Selective Recognition of DNA by Strand Displacement with a Thymine–Substituted Polyamide", *Science,* vol. 254, pp. 1497–1500.

Southern, "Detection of Specicific Sequences Among DNA Fragments Separated by Gel Electrophoresis", *J. Mol. Biol.,* 1975, vol. 98, pp. 503–517.

Dunn et al., "A Novel Method to Map Transcripts: Evidence for Homology Between an Adenovirus mRNA and Discrete Multiple Regions of the Viral Genome", *Cell,* vol. 12, Sep. 1977, pp. 23–36.

Shih et al., "Detection of Multiple, Novel Reverse Transcriptase Coding Sequences in Human Nucleic Acids: Relation to Primate Retroviruses", *J. Virol.,* Jan. 1989, vol. 63, No. 1, pp. 64–75.

Perron et al., "In Vitro Transmission and Antigenicity of a Retrovirus Isolated from a Multiple Sclerosis Patient", *Res. Virol.,* vol. 143, No. 5, 1992, pp. 337–350.

Chomczynski et al., "Single–Step Method of RNA Isolation by Acid Guanidinium Thiocyanate–Phenol–Chloroform Extraction", *Anal. Biochem.,* 1987, vol. 162, pp. 156–159.

Meyerhans et al., "Temporal Fluctuations in HIV Quasispecies in Vivo Are Not Reflected by Sequential HIV Isolations", *Cell,* vol. 58, Sep. 8, 1989, pp. 901–910.

Linial et al., "Retroviral RNA Packaging: Sequence Requirements and Implications", in *Current Topics in Microbiology and Immunobiology. Retroviruses, Strategies of Replication,* Swanstrom et al., eds., vol. 157, 1990, pp. 125–152.

Lori et al., "Viral DNA Carried by Human Immunodeficiency Virus Type 1 Virions", *J. Virol.,* vol. 66, No. 8, Aug. 1992, pp. 5067–5074.

La Mantia et al., "Identification and Characterization of Novel Human Endogenous Retroviral Sequences Prefentially Expressed in Undifferentiated Embryonal Carcinoma Cells", *Nucleic Acids Res.,* 1991, vol. 19, No. 7, pp. 1513–1520.

Frohman et al., "Rapid Production of Full–Length cDNAs from Rare Trancripts: Amplication Using a Single Gene–Specific Oligonucleotide Primer", *Proc. Natl. Acad. Sci. USA,* 1988, vol. 85, pp. 8998–9002.

Mallet et al., "Enzyme–Linked Oligosorbent Assay for Detection of Polymerase Chain Reaction–Amplified Human Immunodeficiency Virus Type I", *J. Clin. Microbiol.,* Jun. 1993, vol. 31, No. 6, pp. 1444–1449.

Acha–Orbea et al., "M1s—A Retrovirus Exploits the Immune System", *Immunology Today,* vol. 12, No. 10, 1991, pp. 356–361.

Asai et al., "J. of Neurochem", vol. 59, No. 1, pp. 307–17, 1992.

*ATCC Catalogue of Cell Lines and Hybridomas,* Sixth Edition, 1988, pp. 165 and 344–355.

C.R.M. Bangham et al., "PCR Analysis of DNA from Multiple Sclerosis Patients for the Presence of HTLV–I", *Science,* vol. 246, Nov. 10, 1989, pp. 821–824.

R. Baccala et al., "Genomically Imposed and Somatically Modified Human Thymocyte vb Gene Repertoires", *Proc. Natl. Acad. Sci.,* vol. 88, pp. 2908, 1991.

Barna et al., "Human Astrocytes Proliferate un Response to Tumor Necrosis Factor Alpha", *J. Neuroimmunol.,* 30 (1990), pp. 239–243.

Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.,* 78, pp. 318–23.

Bergamini et al., "Multiple Sclerosis. I. The Immune Pathogenetic Hypothesis", *Riv. Neurol.,* vol. 59, No. 5, Oct. 1989, pp. 176–190.

T. Bergström et al., "Isolation of Herpes virus Type 1 During First Attack of Multiple Sclerosis.", *Annales Neurology,* vol. 26, pp. 283–285, (1989).

Bernton et al., "No Direct Neuronotoxicity by HIV–1 Virions or Culture Fluids from HIV–1 Infected T Cells or Monocytes", *Aids Research and Human Retroviruses*, vol. 8, No. 4, 1992, pp. 495–403.

Birnbaum et al., "Spinal Fluid Lymphocytes from a Sub-Group of Multiple Sclerosis Patients Respond to Myobacterial Antigens", *Ann. Neurol.*, vol. 34, No. 1, Jul. 1993, pp. 18–24.

Bjare, "Serum–Free Cell Culture", *Pharmac. Ther.*, vol. 53, 1992, pp. 355–374.

C. Bosgiraud et al., "Ultrastructural Study on Visna Virus in Sheep Plexus Choroid Cells", *Biological Abstrats*, vol. 83, No. 7, 1987.

Boyle et al., "Cellular Immune Response in Multiple Sclerosis Plaques", *American Journal of Pathology*, vol. 137, No. 3, Sep. 1990, pp. 575–584.

Bradford, A Rapid and Sensitive Method for the Quantitation of Microgram and Quantities of Protein Utilizing the Principle of Protein–Dye Binding, *Anal. Biochem.*, 72, 1976, pp. 248–254

Brocke et al., "Induction of Relapsing Paralysis in Experimental Autoimmune Encephalomyelitis by Bacterial Superantigen", *Nature*, vol. 365, Oct. 14, 1993, pp. 642–644.

Calder, et al., "MS: A Localized Immune Disease of the Central Nervous System", *Immunology Today*, vol. 10, No. 3, 1989, pp. 99–103.

Carp et al., "Viral Etiology of multiple Sclerosis", *Prog. Med. Virol.*, vol. 24, pp. 158–177, 1978.

Charcot, "Histologie de la sclerose en plaques [Histology of Multiple Sclerosis]", Gaz. Hop. (Paris), 1868; 41, 554–566.

Cole et al., "The Mycoplasma Arthritidis T–Cell Mitogen, MAM: A Model Superantigen", *Immunology Today*, vol. 12, No. 8, 1991, pp. 271–276.

Dalgleish et al., "Do Human T–Lymphotrophic Viruses (HTLVs) and Other Enveloped Viruses Induce Autoimmunity in Multiple Sclerosis?", *Neuropath. App. Neurobiol.*, 1987, 13, pp. 241–250.

A. N. Davison et al., "Biosynthesis of Myelin and Neurotoxic Factors in the Serum of Multiple Sclerosis Patients", *Advances in Experimental Medicine and Biology*, vol. 100, pp. 19–25, 1978.

De Keyser, "Autoimmunity in Multiple Sclerosis", *Neurology*, 38, Mar. 1988, pp. 371–374.

S. Dhib–Jalbut et al., "Measles Virus Polypeptide–Specific Antibody Profile in Multiple Sclerosis", *Neurology*, vol. 40, pp. 430–435, (1990).

Ebers et al., "The Geography of MS Reflects Genetic Susceptibility", *Neurology*, 36, Apr. 1986, Suppl. 1, p. 108.

Escourolle et al., "Principales Donnees Morphologigues Approches Physiopathologigues et Etiologiques de la Sclerose en Plaques [Principle Morphological Data, Physiopathological and Etiological Approaches to Multiple Sclerosis]", *La Reveue du Praticien*, Paris, 1980; 30, pp. 2047–2053.

E. J. Field, "Immunological Treatment for Multiple Sclerosis", *The Lancet*, Jun. 3, 1989, p. 1272.

Medline Abstract of FU et al., "Rabies virus nucleoprotein expressed in and purified from insect cells is efficacious as a vaccine," Proc Natl Acad Sci USA 88: 2001–05 (1991).

Galiana et al., "Estabishment of Permanent Astroglial Cell Lines, Able to Differentiate in Vitro, From Transgenic Mice Carrying the Polyoma Virus Large T Gene: An Alternative Approach to Brain Cell Immortalization", *Journal of Neuroscience Research*, 1990; 26: pp. 269–277.

M. B. Gardner et al., "Cogenital Transmission of Murine Leukaemia Virus from Wild Mice Prone to Development of Lymphoma and Paralysis", *J. Natl. Cancer Inst.*, vol. 62, pp. 63–69, (1979).

M. B. Gardner, "Genetic resistance to a Retroviral Neurologic Disease in Wild Mice, in Retrovirus Infections of the Nervous System", *Oldstone M.B.A. and Koprowsky H. Eds. Current Topice in Microbiology and Immunology*, No. 160, pp. 3–10, (Springer–Verlag, Berlin, 1990).

Gay, "Is Multiple Sclerosis Caused by an Oral Spirochaete", *The Lancet*, Jul. 12, 1986, pp. 75–77.

A. Gessain et al., Antibodies to Human T–lymphotrophic Virus type–I in Patients with Tropical Spastic Paraparesis, *Lancet*, vol. 2, pp. 407–410, (1985).

Giulian et al., "The Envelope Glycoprotein of Human Immunodeficiency Virus Type 1 Stimulates Release of Neurotoxins from Monocytes", *Proc. Natl. Acad. Sci. USA*, vol. 90, 1993, pp. 2769–2773.

D. Giulian et al., "Secretion of Neurotoxins by Mononuclear Phagocytes Infected with HIV–1", *Science*, vol. 250, Dec. 14, 1990. pp. 1593–1596.

Gonzalez–Scarano et al., "Multiple Sclerosis Disease Activity Correlates with Gadolinium–Enhanced Magnetic Resonance Imaging", *Annals of Neurology*, vol. 21, No. 3, Mar. 1987, pp. 300–306.

F. Gonzalez–Scarano et al., "Sequence Similarities Between Human Immunodeficiency Virus gp41 and Paramyxovirus Fusion Proteins.", *AIDS Res. Hum. Retrov.*, vol. 3, pp. 245–252, (1987).

S. Haahr et al., "A Putative New Retrovirus Associated with Multiple Sclerosis and the Possbile Involvement of Epstein–Barr Virus in this Disease", *NY Acad. Science*, vol. 724, pp. 148–156, 1994.

S. Haahr et al., "Just Another Dubious Virus in Cells from a Patient with Multiple Sclerosis?", *The Lancet*, vol. 337, Apr. 6, 1991, pp. 863–864.

A. T. Haase, "Pathogenesis of Lentivirus Infectious", *Nature*, vol. 322, Jul. 10, 1986, pp. 130–136.

Haegert et al. HLA–DRβ, –DQα, and –DQβ Restriction Fragment Length Polymorphisms in Multiple Sclerosis, *J. Neurosci. Res.*, 1989; 23, pp. 46–54.

Hauw et al., "Aspects Anatomo–Pathologiques de la Sclerose en Plaques [Anatomopathological Aspects of Multiple Sclerosis]", *La Sclerose en Plaques [Multiple Sclerosis]*, 9–47 (Racol et al. eds., 1980).

Hoffman et al., "Handbook of Clinical Neurology, 12; Viral Diseases", R.R. McKendall, ed., Elsevier Science Publishing, Amsterdam, 1989, pp. 453–466.

Huck et al., "J. of Nerosei", vol. 4, No. 10, pp. 2650–2657, 1984.

A. W. Hugin et al., "A Virus–Encoded Superantigen in a Retrovirus–Induced Immunodeficiency Syndrome of Mice", *Science*, vol. 252, pp. 424–427, (1991).

Medline abstract of JARRETT et al., "Studies on vaccination against papillomaviruses: a comparison of purified virus, tumour extract and transformed cells in prophylactic vaccination," Vet Rec 126: 449–52 (1990).

Jervis et al., "Allergic Encephalomyelitis", *J. Neuropathol. Exp. Neurol.*, 1948; 7, pp. 309–320.

R.T. Johnson, "Nononcogenic Retrovirus Infections as Models for Chronic and Relapsing Human Diseases: Introduction", *Revies of Infectious Diseases*, vol. 7, No. 1, Jan.–Feb. 1985, pp. 66–67.

Juntunen et al. "Multiple Sclerosis and Occupational Exposure to Chemicals: A Co–Twin Study of a Nationwide Series of Twins", *Br. J. Int. Med.,* 1989; 46: pp. 417–419.

Kent et al., "Cerebral Blood Flow, Cerebral Metabolism and Blood–Brain Barrier," *Handbook of Clinical Neurology,* vol. 56(12), 1989, pp. 79–91.

Medline abstract of LEAO, "Tuberculosis: new strategies for the development of diagnostic tests and vaccines," Braz J Biol Res 26: 827–33 (1993).

Levi et al., Human Immunodeficiency Coat Protein gp120 Inhibits the β–adrenergic Regulation of Astroglial and Microglial Functions, *Proc. Natl. Acad. Sci. USA,* vol. 90, Feb. 1993, pp. 1541–1545.

Levine et al., "Conversion of Lytic to Persistent Alphavirus Infection by the bcl-2 Cellular Oncogene", *Nature,* vol. 361, Feb. 25, 1993, pp. 739–742.

Y.S. Lie et al., Journal of Virology, vol. 68, No. 12, Dec. 1994, pp. 7840–7849, "Chinese hamster ovary cells contain transcriptionally active full length type C provirises".

Lo et al, "Newly Discovered Mycoplasma Isolated from Patients Infected with HIV", *The Lancet,* vol. 338, Dec. 7, 1991, pp. 1415–1418.

F. Mallet et al., "Continuous RT–PCR and tag DNA Polymerase: Characterization and Comparison to Uncoupled Procedures", *Biotechniques,* vol. 18, pp. 678–687, 1985.

Marie, "Sclerose en Plaques et Maladies Infectieuses [Multiple Sclerosis and Infectious Diseases]", *Le Progres Medical,* 1884, 12, pp. 287–289.

P. Marrack et al., "A Maternally Inherited Superantigen Encoded by a Mammary Tumor Virus", *Nature,* vol. 349, pp. 524–526, (1991).

McDonald, "The Mystery of the Orgin of Multiple Sclerosis", *J. Neurol. Neurosurg. Psych.,* 1986; 49, pp. 113–123.

J.D. Mosca et al., "Activation of human immunodeficiency virus by herpesvirus infection: Identification of a region within the long terminal repeat that responds to a transacting factor encoded by herpes simplex virus 1", *Proceedings of the National Academy of Sciences of USA,* vol. 84, No. 21, Nov. 1987, pp. 7408–7412.

Mosmann, "Rapid Colorimetric Assay for Cellular Growth and Survival: Application to Proliferation and Cytotoxicity Assays", *Journal of Immunological Methods,* 65, 1983, pp. 55–63.

O. Narayan et al., "Lentiviral Diseases of Sheep and Goats: Pneumonia Leukoencephalomyelitis, and Arthritis", *Reviews of Infectious Diseases,* vol. 7, No. 1, Jan.–Feb. 1985, pp. 89–98.

N. Nathanson et al., "Experimental Visna in Icelandic Sheep: The Protytepe Lentiviral Infection", *Reviews of Infectious Diseases,* vol. 7, no. 1, Jan.–Feb. 1985, pp. 75–82.

Newell et al., "Ligation of Major Histocompatibility Complex II Molecules Mediates Apoptotic Cell Death in Resting B Lymphocytes", *Proc. Natl. Acad. Sci. USA,* vol. 90, Nov. 1993, pp. 10459–10463.

Medline abstract of ORLANDI et al., "Characterization of the 175–kilodalton erthrocyte binding antigen of Plasmodium falciparum," Mol Biochem Parasitol 40: 285–94 (1990).

Ostrove et al., "Activation of the Human Innumodeficiency Virus by Herpes Simplex Virus Type 1", J Virol 61(12), Dec. 1987, pp. 3726–3732.

J.L. Pablos et al., "A novel retroviral POL sequence is present in patients with rheumatoid arthritis", & American College of Rheumatology 57th Annual Scientifc Meeting, Nov. 7–11, 1993 San Antonio, Texas, USA, *Arthritis and Rheumatism,* vol. 36, No. 9 suppl. 1993, p S55, Abstract No. 102.

Medline abstract of PEI et al., "Identification, purification, and characterization of major antigenic proteins of Campylobacter jejuni," J Biol Chem 266: 16363–69 (1991).

H. Perron et al., "Leptomeningeal cell line from multiple sclerosis with reverse transcriptase activity and viral particles", Biological Abstracts, vol. 89, No. 9, May 1, 1990.

H. Perron et al., "Antibody to Reverse Transcriptase of Human Retrovirus in Multiple Sclerosis", Biological Abstracts, vol. 93, No. 6, Mar. 15, 1992.

Perron et al., "Retroviral Reactibation by Herpesviruses in MS: Serological Arguments", Current Concepts in Multiple Sclerosis 1991, pp. 331–332.

A. Plaza et al., Theofilopoulos, A.N. New Human vβ 12DD Genes and Polymorphic Variants. J. Imm; vol. 147, No. 12, pp. 4360–4365, 1991.

Poirier et al., "La Barriere Hemato–Encephalique. Donnees Morphologiques [The Blood–Brain Barrier. Morphological Data]", *La Revue de Medecine Interne,* vol. IV, no. 2, Jun. 1983, pp. 131–144.

J. L. Portis, "Wild Mouse Retrovirus: Pathogenesis in Retrovirus Infections of the Nervous System". Oldstone M.B.A. and Koprowsky H. Eds. Current topics in microbiology and immuology, n°160, pp. 11–27, (Springer–Verlag, Berlin, 1990).

C.M. Poser et al., "New Diagnostic Criteria for Multiple Sclerosis: Guidelines for Research Protocols, In The diagnosis of Multiple Sclerosis", *Thieme Stratton Inc.,* pp. 225–229, 1984.

D.N., Posnet, "Do Superantigens Play a Role in Autoimmunity?", *Semin. Immunol.,* vol. 5, pp. 65–72, 1993.

Prineas, "The Neuropathology of Multiple Sclerosis", *Handbook of Clinical Neurology,* vol. 3 (47), 1985, pp. 213–257.

Prineas et al., "Multiple Sclerosis: Remyelination of Nascent Lesions", *Annals of Neurology,* vol. 33, No. 2, Feb. 1993, pp. 137–151.

Prineas, "Pathology of the Early Lesion in Multiple Sclerosis", *Human Pathology,* vol. 5, Sep. 1975, pp. 531–554.

Prineas et al., "Macrophages, Lymphocytes, and Plasma Cells in the Preivascular Compartment in Chronic Multiple Sclerosis", *Laboratory Investigation,* vol. 38, No. 4, 1978, pp. 409–421.

Ransohoff et al., "Heat–Shock Proteins and Autoimmunity: Implications for Multiple Sclerosis", *Annals of Neurology,* vol. 34, No. 1, Jul. 1993, pp. 5–7.

Rapoport, *Blood–Brain Barrier in Physiology and Medicine,* 129 (1976).

S. S. Rhee et al., "A single Amino Acid Substitution Within the Matrix Protein of a D–Type Retrovirus Converts Its Morphogenesis to that of a C–Type Retrovirus", Cell 63, pp. 77–86, (1990).

Robbins et al., "Production of Cytotoxic Factor for Oligodendrocytes by Stimulated Astrocytes", *Journal of Immunology,* vol. 139, No. 8, Oct. 15, 1987, pp. 2593–2597.

Medline abstract of Rumschlag et al., "Immunologic characterization of a 35–kilodalton recombinant antigen of Mycobacterium tuberculosis," J Clin Microbiol 28: 591–95 (1990).

Medline abstract of Sakulramrung et al., "Antigenic and immunogenic characteristics of subcellular fractions and whole cells of a rough E. coli 0111 (J5) mutant," Immunobiology 169: 372–88 (1985).

Selmaj, et al., "Tumor Necrosis Factor Mediates Myelin and Oligodendrocyte Damage In Vitro", *Annals of Neurology*, vol. 23, No. 4, Apr. 1988, pp. 339–346.

Silberberg et al., "Tissue Culture Demyelination by Normal Human Serum", *Annals of Neurology*, vol. 15, No. 6, Jun. 1994, pp. 575–580.

M. Sommerlund et al., "Retrovirus–like particles in an Epstein–Barr virus–producing cell line derived from a patient with chronic progressive myelopathy", *Acta Neurol Scand*, 1993: 87: pp. 71–76.

P. Sonigo et al., "Nucleotide Sequence of Mason–Pfizer Monkey Virus: An immunosuppressive D–Type Retrovirus", Cell 45, pp. 375–385, (1986).

Traugott, "Multiple Sclerosis: Relevance of Class I and Class II MHC–Expressing Cells to Lesion Development", *Journal of Neuroimmunity*, 16, 1987, pp. 283–302.

Waksman, "Mechanisms in Multiple Sclerosis", *Nature*, vol. 318, Nov. 14, 1985, pp. 104–105.

Williams et al., "Molecular Regulation of Apoptosis: Genetic Controls on Cell Death", *Cell*, vol. 74, Sep. 10, 1993, pp. 777–779.

Wienfield et al., "Stress Proteins, Autoimmunity, and Autoimmunity, and Autoimmune Disease", *Current Topics in Microbiology and Immunology*, vol. 167, Springer–Verlag, Berlin, 1991, pp. 161–189.

D. L. Wilkinson et al., "Evidence for a functional subclass of the RTLV–H family of human endogenous retrovirus–like sequences", *J. Virol.*, vol. 67, pp. 2981–2989, (1993).

Wollinsky et al., "Liquorpherese bei 10 Patienten mit Multipler Sklerose [Fluid Phoresis in 10 Patients With Multiple Sclerosis]", *Verhandlungen der Deutschen Deutschen Gesellschaft fur Neurologie*, vol. 7, 1992, pp. 444–445.

Woodland, et al., "An Endogenous Retorvirus Mediating Deletion of αβT cells?", *Nature,* vol. 349, Feb. 7, 1991, pp. 529–530.

Boswell et al., 1988, Oxford Univ. Pres), Chapt. 14, pp. 161–178.

Shih et al., 1989, J. of Virol., vol. 63, pp. 64–75.

Perron et al, 1992, Rej. virol, vol. 143, pp. 337–350.

Greenberg et al, 1989, PNAS USA, vol. 86, pp. 2878–2882.

FIG. 1

```
pol  SHIH    TGGAAAGTGT  TGCCACAGGG  CGCTGAAGCC  TATCGCGTGC  AGTTGCCGGA    50
pol  SHIH    TGCCGCCTAT  AGCCTCTACA  TGGATGACAT  CCTGCTGGCC  TCC           93
```

*SEQ ID NO 10*

FIG. 2

| | | | | | | |
|---|---|---|---|---|---|---|
| Consensus | GTTTAGGGAT | ANCCCTCATC | TCTTTGGTCA | GGTACTGGCC | CAAGATCTAG | 50 |
| Consensus | GCCACTTCTC | AGGTCCAGSN | ACTCTGTYCC | TTCAG | 85 | |

*SEQ ID NO 3*

| | | | | | | |
|---|---|---|---|---|---|---|
| Consensus | GTTCAGGGAT | AGCCCCCATC | TATTTGGCCA | GGCACTAGCT | CAATACTTGA | 50 |
| Consensus | GCCAGTTCTC | ATACCTGGAC | AYTCTYGTCC | TTCGGT | 86 | |

*SEQ ID NO 4*

| | | | | | | |
|---|---|---|---|---|---|---|
| Consensus | GTTCARRGAT | AGCCCCCATC | TATTTGGCCW | RGYATTAGCC | CAAGACTTGA | 50 |
| Consensus | GYCAATTCTC | ATACCTGGAC | ACTCTTGTCC | TTYRG | 85 | |

*SEQ ID NO 5*

| | | | | | | |
|---|---|---|---|---|---|---|
| Consensus | GTTCAGGGAT | AGCTCCCATC | TATTTGGCCT | GGCATTAACC | CGAGACTTAA | 50 |
| Consensus | GCCAGTTCTY | ATACGTGGAC | ACTCTTGTCC | TTTGG | 85 | |

*SEQ ID NO 6*

| | | | | | |
|---|---|---|---|---|---|
| Consensus | GTGTTGCCAC | AGGGGTTTAR | RGATANCYCY | CATCTMTTTG | GYCWRGYAYT |
| Consensus | RRCYCRAKAY | YTRRGYCAVT | TCTYAKRYSY | RGSNAYTCTB | KYCCTTYRGT |
| Consensus | ACATGGATGA | C | | | |

*SEQ ID NO 7*

FIG. 4

CONSENSUS A

```
GTTTAGGGATAGCCC   TCATCTCTTTGGTCA   GGTACTGGCCCAAGA   TCTAGGCCACTTCTC   60
V - G - P         S   S   L   W   S   G   T   G   P   R     S   R   P   L   L
  F   R   D   S   P     H   L   F   G   Q     V   L   A   Q   D     L   G   H   F   S
    L   G   I   A   L     I   S   L   V   R     Y   W   P   K   I     -   A   T   S   Q

AGGTCCAGGCACTCT   GTTCCTTCAG                                          85
R   S   R   H   S   V   P   S
  G   P   G   T   L     F   L   Q
    V   Q   A   L   C     S   F
```

CONSENSUS B

```
GTTCAGGGATAGCCC   CCATCTATTTGGCCA   GGCACTAGCTCAATA   CTTGAGCCAGTTCTC   60
V   Q   G   -   P   P   S   I   W   P   G   T   S   S   I     L   E   P   V   L
  F   R   D   S   P     H   L   F   G   Q     A   L   A   Q   Y     L   S   Q   F   S
    S   G   I   A   P     I   Y   L   A   R     H   -   L   N   T     -   A   S   S   H

ATACCTGGACACTCT   TGTCCTTCGGT                                         86
I   P   G   H   S   C   P   S
  Y   L   D   T   L     V   L   R
    T   W   T   L   L     S   F   G
```

CONSENSUS C

```
GTTCAGGGATAGCCC   CCATCTATTTGGCCA   GGCATTAGCCCAAGA   CTTGAGTCAATTCTC   60
V   Q   G   -   P   P   S   I   W   P   G   I   S   P   R     L   E   S   I   L
  F   R   D   S   P     H   L   F   G   Q     A   L   A   Q   D     L   S   Q   F   S
    S   G   I   A   P     I   Y   L   A   R     H   -   P   K   T     -   V   N   S   H

ATACCTGGACACTCT   TGTCCTTCAG                                          85
I   P   G   H   S   C   P   S
  Y   L   D   T   L     V   L   Q
    T   W   T   L   L     S   F
```

CONSENSUS D

```
GTTCAGGGATAGCTC   CCATCTATTTGGCCT   GGCATTAACCCGAGA   CTTAAGCCAGTTCTC   60
V   Q   G   -   L   P   S   I   W   P   G   I   N   P   R     L   K   P   V   L
  F   R   D   S   S     H   L   F   G   L     A   L   T   R   D     L   S   Q   F   S
    S   G   I   A   P     I   Y   L   A   W     H   -   P   E   T     -   A   S   S   H

ATACGTGGACACTCT   TGTCCTTTGG                                          85
I   R   G   H   S   C   P   L
  Y   V   D   T   L     V   L   W
    T   W   T   L   L     S   F
```

FIG. 5

| | | | | | | |
|---|---|---|---|---|---|---|
| Consensus | TTGGATCCAG | TGYTGCCACA | GGGCGCTGAA | GCCTATCGCG | TGCAGTTGCC | 50 |
| Consensus | GGATGCCGCC | TATAGCCTCT | ACGTGGATGA | CCTSCTGAAG | CTTGAG | 96 |

*SEQ ID NO 11*

FIG. 8

| | | | | | |
|---|---|---|---|---|---|
| CAAGCCACCC | AAGAACTCTT | AAATTTCCTC | ACTACCTGTG | GCTACAAGGT | 50 |
| TTCCAAACCA | AAGGCTCAGC | TCTGCTCACA | GGAGATTAGA | TACTTAGGGT | 100 |
| TAAAATTATC | CAAAGGCACC | AGGGGCCTCA | GTGAGGAACG | TATCCAGCCT | 150 |
| ATACTGGGTT | ATCCTCATCC | CAAAACCCTA | AAGCAACTAA | GAGGGTTCCT | 200 |
| TAGCATGATC | AGGTTTCTGC | CGAAAACAAG | ATTCCCAGGT | ACAACCAAAA | 250 |
| TAGCCAGACC | ATTATATACA | CTAATTAAGG | AAACTCAGAA | AGCCAATACC | 300 |
| TATTTAGTAA | GATGGACACC | TAAACAGAAG | GCTTTCCAGG | CCCTAAAGAA | 350 |
| GGCCCTAACC | CAAGCCCCAG | TGTTCAGCTT | GCCAACAGGG | CAAGATTTTT | 400 |
| CTTTATATGG | CACAGAAAAA | ACAGGAATCG | CTCTAGGAGT | CCTTACACAG | 450 |
| GTCCGAGGGA | TGAGCTIGCA | ACCCGTGGCA | TACCTGAATA | AGGAAATTGA | 500 |
| TGTAGTGGCA | AAGGGTIGGC | CTCATNGTTT | ATGGGTAATG | GNGGCAGTAG | 550 |
| CAGTCINAGT | ATCTGAAGCA | GTTAAAATAA | TACAGGGAAG | AGATCTINCT | 600 |
| GTGTGGACAT | CTCATGATGT | GAACGGCATA | CTCACTGCTA | AAGGAGACTT | 650 |
| GTGGTTGTCA | GACAACCATT | TACTTAANTA | TCAGGCTCTA | TTACTTGAAG | 700 |
| AGCCAGTGCT | GNGACTGCGC | ACTTGTGCAA | CTCTTAAACC | C | 741 |

SEQ ID NO 9

FIG. 9

TCAGGGATAGCCCCCATCTATTTGGCCAGGCATTAGCCCAAGACTTGAGTC

AATTCTCATACCTGGACACTCTTGTCCTTCAGTACATGGATGATTTACTTT

TAGTCGCCCGTTCAGAAACCTTGTGCCATCAAGCCACCCAAGAACTCTTAA

CTTTCCTCACTACCTGTGGCTACAAGGTTTCCAAACCAAAGGCTCGGCTCT

GCTCACAGGAGATTAGATACTNAGGGCTAAAATTATCCAAAGGCACCAGG

GCCCTCAGTGAGGAACGTATCCAGCCTATACTGGCTTATCCTCATCCCAAA

ACCCTAAAGCAACTAAGAGGGTTCCTTGGCATAACAGGTTTCTGCCGAAA

ACAGATTCCCAGGTACASCCCAATAGCCAGACCATTATATACACTAATTA

NGGAAACTCAGAAAGCCAATACCTATTTAGTAAGATGGACACCTACAGAA

GTGGCTTTCCAGGCCCTAAAGAAGGCCCTAACCCAAGCCCCAGTGTTCAGC

TTGCCAACAGGGCAAGATTTTTCTTTATATGCCACAGAAAAAACAGGAAT

AGCTCTAGGAGTCCTTACGCAGGTCTCAGGGATGAGCTTGCAACCCGTGGT

ATACCTGAGTAAGGAAATTGATGTAGTGGCAAAGGGTT

*SEQ ID NO 8*

FIG. 10

```
         10              20              30              40              50              60              70
         *               *               *               *               *               *               *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R >
___a_____a_____a_____a_____a_____a_____a___ TRANSLATION OF F11-1 (A) _a_____a_____a_____a___

80              90             100             110             120             130             140
         *               *               *               *               *               *               *
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I   P >
___a_____a_____a_____a_____a_____a_____a___ TRANSLATION OF F11-1 (A) _a_____a_____a___

150             160             170             180             190             200             210
         *               *               *               *               *               *               *
GAG GAA GCA GAG TGG TTT ACA GTC CTG GAC CTT AAG GAT GCC TTT TTC TGC ATC CCT GTA CGT CCT GAC TCT
 E   E   A   E   W   F   T   V   L   D   L   K   D   A   F   F   C   I   P   V   R   P   D   S >
___a_____a_____a_____a_____a_____a_____a___ TRANSLATION OF F11-1 (A) _a_____a_____a___

220             230             240             250             260             270             280
         *               *               *               *               *               *               *
CAA TTC TTG TTT GCC TTT GAA GAT CCT TTG AAC CCA ACG TCT CAA CTC ACC TGG ACT GTT TTA CCC CAA GGG
 Q   F   L   F   A   F   E   D   P   L   N   P   T   S   Q   L   T   W   T   V   L   P   Q   G >
___a_____a_____a_____a_____a_____a_____a___ TRANSLATION OF F11-1 (A) _a_____a_____a___

290
         *
TTC AAG GGA
 F   K   G >
___a___
```

SEQ ID NO 2

FIG. 11A

```
            10         20         30         40         50         60         70
             *          *          *          *          *          *          *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R>
___a___a___a___a___a___a___a___TRANSLATION OF MSRV-1 POL    (A)___a___a___a___a___a___a___a___>

80         90        100        110        120        130        140
             *          *          *          *          *          *          *
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I   P>
___a___a___a___a___a___a___a___TRANSLATION OF MSRV-1 POL    (A)___a___a___a___a___a___a___a___>

150        160        170        180        190        200        210
             *          *          *          *          *          *          *
GAG GAA GCA GAG TGG TTT ACA GTC CTG GAC CTT AAG GAT GCC TTT TTC TGC ATC CCT GTA CGT CCT GAC TCT
 E   E   A   E   W   F   T   V   L   D   L   K   D   A   F   F   C   I   P   V   R   P   D   S>
___a___a___a___a___a___a___a___TRANSLATION OF MSRV-1 POL    (A)___a___a___a___a___a___a___a___>

220        230        240        250        260        270        280
             *          *          *          *          *          *          *
CAA TTC TTG TTT GCC TTT GAA GAT CCT TTG AAC CCA ACG TCT CAA CTC ACC TGG ACT|GTT TTA CCC CAA GGG|
 Q   F   L   F   A   F   E   D   P   L   N   P   T   S   Q   L   T   W   T | V   L   P   Q   G>|
___a___a___a___a___a___a___a___TRANSLATION OF MSRV-1 POL    (A)___a___a___a___a___a___a___a___>

290        300        310        320        330        340        350        360
  *          *          *          *          *          *          *          *
TTC AGG GAT AGC CCC CAT CTA TTT GGC CAG GCA TTA GCC CAA GAC TTG AGT CAA TTC TCA TAC CTG GAC ACT
 F   R   D   S   P   F   E   D   P   L   N   P   T   S   Q   L   T   W   T   V   L   P   Q   G>
___a___a___a___a___a___a___a___TRANSLATION OF MSRV-1 POL    (A)___a___a___a___a___a___a___a___>

370        380        390        400        410        420
                   *          *          *          *          *          *          *
CTT GTC CTT CAG|TAC ATG GAT GAT|TTA CTT TTA GTC GCC CGT TCA GAA ACC TTG TGC CAT CAA GCC ACC CAA
 L   V   L   Q | Y   M   D   D | L   L   L   V   A   R   S   E   T   L   C   M   Q   A   T   Q>
___a___a___a___a___a___a___a___TRANSLATION OF MSRV-1 POL    (A)___a___a___a___a___a___a___a___>

440        450        460        470        480        490        500
             *          *          *          *          *          *          *
GAA CTC TTA ACT TTC CTC ACT ACC TGT GGC TAC AAG GTT TCC AAA CCA AAG GCT CGC CTC TGC TCA CAG GAG
 E   L   L   T   F   L   T   T   C   G   Y   K   V   S   K   F   K   A   K   L   C   I   Q   F>
___a___a___a___a___a___a___a___TRANSLATION OF MSRV-1 POL    (A)___a___a___a___a___a___a___a___>

510        520        530        540        550        560        570
             *          *          *          *          *          *          *
ATT AGA TAC TNA GGG CTA AAA TTA TCC AAA GGC ACC AGG GCC CTC AGT GAG GAA CGT ATC CAG CCT ATA CTG
 I   R   Y   X   G   L   K   L   S   K   G   T   R   A   L   S   E   E   R   I   Q   F   I   L>
___a___a___a___a___a___a___a___TRANSLATION OF MSRV-1 POL    (A)___a___a___a___a___a___a___a___>

580        590        600        610        620        630        640
             *          *          *          *          *          *          *
GCT TAT CCT CAT CCC AAA ACC CTA AAG CAA CTA AGA GGG TTC CTT GGC ATA ACA GGT TTC TGC CGA AAA CAG
 A   Y   P   M   P   K   T   L   K   Q   L   K   G   F   L   G   I   T   G   F   C   R   K   Q>
___a___a___a___a___a___a___a___TRANSLATION OF MSRV-1 POL    (A)___a___a___a___a___a___a___a___>

650        660        670        680        690        700        710        720
  *          *          *          *          *          *          *          *
ATT CCC AGG TAC ASC CCA ATA GCC AGA CCA TTA TAT ACA CTA ATT ANG GAA ACT CAG AAA GCC AAT ACC TAT
 I   F   R   Y   X   P   I   A   R   P   L   Y   T   L   I   X   K   T   Q   K   A   M   T   Y>
___a___a___a___a___a___a___a___TRANSLATION OF MSRV-1 POL    (A)___a___a___a___a___a___a___a___>

730        740        750'       760        770        780        790
                  *          *          *          *          *          *          *
TTA GTA AGA TGG ACA CCT ACA GAA GTG GCT TTC CAG GCC CTA AAG AAG GCC CTA ACC CAA GCC CCA GTG TTC
 L   V   R   W   T   P   T   E   V   A   F   Q   A   L   K   K   A   L   T   Q   A   P   V   F>
___a___a___a___a___a___a___a___TRANSLATION OF MSRV-1 POL    (A)___a___a___a___a___a___a___a___>
```

FIG. 11B

```
          800            810            820            830            840            850            860
           *              *              *              *              *              *              *
AGC TTG CCA ACA GGG CAA GAT TTT TCT TTA TAT GCC ACA GAA AAA ACA GGA ATA GCT CTA GGA GTC CTT ACG
 S   L   P   T   G   Q   D   F   S   L   Y   A   T   E   K   T   G   I   A   L   G   V   L   T>
___a___a___a___a___a___a___a___TRANSLATION OF MSRV-1 POL

FIG. 12

```
         10                    20          30              40
          *                     *           *               *
   TGCAAGCTTCACCGC       TTGCTGGATGTAGGC        CTCAGTACCGGNTG 50          60             70              80          90
          *           *              *               *           *
   CCCCGCGCGCTGTAG       TTCGATGTAGAAAGC        GCCCGGAAACACGCG 100                   110         120             130
          *                     *           *               *
   GGACCAATGCGTCGC       CAGCTTGCGCGCCAG        CGCCTCGTTGCCATT 140         150            160             170         180
          *           *              *               *           *
   GGCCAGCGCCACGCC       GATATCACCCGCCAT        GGCGCCGGAGAGCGC 190                   200         210             220
          *                     *           *               *
   CAGCAGACCGGCGGC       CAGCGGCGCATTCTC        AACGCCGGGCTCGTC 230         240            250             260         270
          *           *              *               *           *
   GAACCATTCGGGGGC       GATTTCCGCACGACC        GCGATGCTGGTTGGA 280                   290         300             310
          *                     *           *               *
   GAGCCAGGCCCTGGC       CAGCAACTGGCACAG        GTTCAGGTAACCCTG 320         330            340             350         360
          *           *              *               *           *
   CTTGTCCOGCACCAA       CAGCAGCAGGCGGGT        CGGCTTGTCGCGCTC 370                   380         390             400
          *                     *           *               *
   GTCGTGATTGGTGAT       CCACACGTCAGCCCC        GACGATGGGCTTCAC 410         420            430             440         450
          *           *              *               *           *
   GCCCTTGCCACGCGC       TTCCTTGTAGANGCG        CACCAGCCCGAAGGC 460                   470         480             490
          *                     *           *               *
   ATTGGCGAGATCGGT       CAGCGCCAAGGCGCC        CATGCCATCTTTGGC 500         510            520             530         540
          *           *              *               *           *
   GGCAGCCTTGACGGC       ATCGTCGAGACGGAC        ATTGCCATCGACGAC 550                   560         570             580
          *                     *           *               *
   GGAATATTCGGAGTG       GAGACGGAGGTGGAC        GAAGCGCGGCGAATT 590         600            610             620         630
          *           *              *               *           *
   CATCCGCGTATTGTA       ACGGGTGACACCTTC        CGCAAAGCATTCCGG 640                   650         660             670
          *                     *           *               *
   ACGTGCCCGATTGAC       CCGGAGCAACCCCGC        ACGGCTGCGCGGGCA 680         690            700             710         720
          *           *              *               *           *
   GTTATAATTTCGGCT       TACGAATCAACGGGT        TACCCCAGGGCGCTG 730                   740
          *                     *
   AAGCCTATCG CGTGC    AGTTGCCGGATGC
```

SEQ ID NO 12

SEQ ID NO 12

FIG. 14

```
                 10              20              30              40              50              60              70              80              90
                  *               *               *               *               *               *               *               *               *
MSRV-2A   TGGAAAGTGTTGCCA CAGGGGCGCTGAAGCC TATCGCGTGCAGTTG CCGGATGCCGCCTAT AGCCTCTACATGGAT GACATCCTGCTGGCC TCC
                 700             710             720             730             740
          cAAcGgTTaCCc CAGGGGCGCTGAAGCC TATCG[CGTGCAGTTG CCGGATGC]>
          ** * *** **

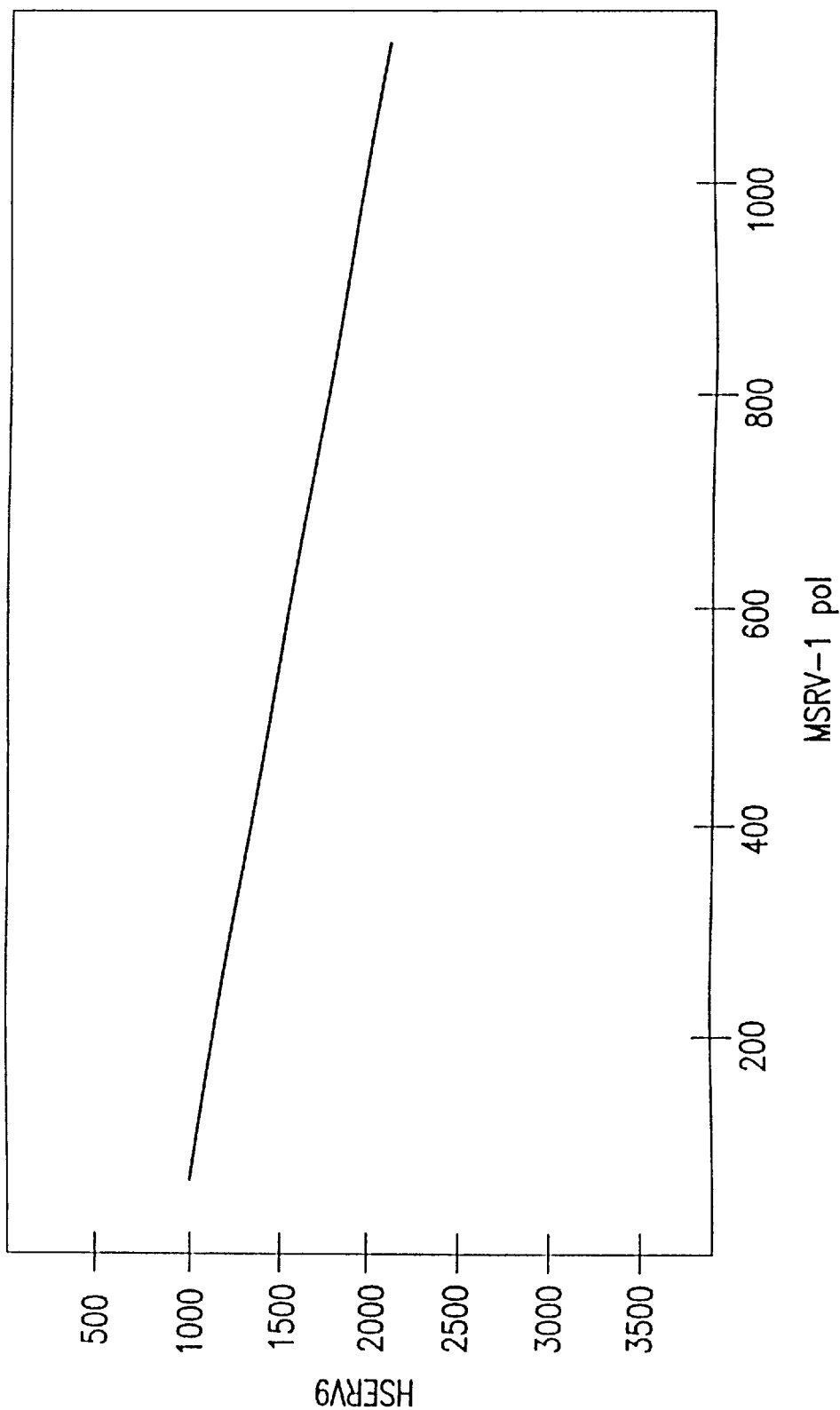

MULTIPLE SCLEROSIS RELATED VIRUS

This is a divisional application of Ser. No. 08/384,137, filed Feb. 6, 1995.

BACKGROUND

Multiple sclerosis (MS) is a demyelinating disease of the central nervous system (CNS) the cause of which remains as yet unknown.

Many studies have supported the hypothesis of a viral etiology of the disease, but none of the known viruses tested has proved to be the causal agent sought: a review of the viruses sought for several years in MS has been compiled by E. Norrby (1) and R. T. Johnson (2).

Concomitantly, the possibility of an exogenous and/or infectious factor is suggested by the existence of localized epidemics or "clusters" of MS, as have been observed in the Faro Islands between 1943 and 1960 (3), in Sardinia (4), in Norway (5), and also by studies on migrant populations (6). Among all the exogenous factors suggested, viruses have been most often studied, and a viral etiology is traditionally called to mind.

The observation in MS of phenomena which can be likened to an autoimmunity reaction has led to an "essential" autoimmunity etiological hypothesis (7 and 8). However, this autoimmunity directed against certain components of the CNS has been found not to be specific to MS and common in inflammation of the CNS, whether or not associated with an infection (9, 10, 11 and 12). Furthermore, none of the immunosuppressive therapies has enabled decisive results to be obtained against MS (13). It now seems likely that the "autoimmune" manifestations are induced by a mechanism of viral origin: cosensitization to viral determinants associated with molecules of cellular origin, phenomena of molecular mimicry (14), or by expression of retroviral superantigens (15).

Some studies have supported a hypothesis according to which a retrovirus is at the origin of the disease: the recent discovery (16) of neurological syndromes associated with the HTLV-I virus, originally known as an adult T-cell leukemia agent, has led many authors (17, 18, 19, 20, 21, 22, 23) to look for an involvement of this human retrovirus in MS, however without success or with results suggesting cross-reactions.

Recently, a retrovirus different from the known human retroviruses has been isolated in patients suffering from MS (24, 25 and 26). The authors were also able to show that this retrovirus could be transmitted in vitro, that patients suffering from MS produced antibodies capable of recognizing proteins associated with the infection of leptomeningeal cells by this retrovirus, and that the expression of the latter could be strongly stimulated by the immediate-early genes of some herpesviruses (27).

All these results point to a role in MS of at least one unknown retrovirus or of a virus having reverse transcriptase activity which is detectable according to the method published by H. Perron (24) and qualified as "LM7-like RT" activity. The content of the publication identified by (24) is incorporated in the present description by reference.

Recently, the Applicant's studies have enabled two continuous cell lines infected with natural isolates originating from two different patients suffering from MS to be obtained by a culture method as described in the document WO-A-9320188, the content of which is incorporated in the present description by reference. These two lines, derived from human choroid plexus cells, designated LM7PC and PLI-2, were deposited with the ECACC on Jul. 22 1992 and Jan. 8 1993, respectively, under numbers 92072201 and 93010817, in accordance with the provisions of the Budapest Treaty. Moreover, the viral isolates possessing LM7-like RT activity were also deposited with the ECACC under the overall designation of "strains". The "strain" or isolate harbored by the PLI-2 line, designated POL-2, was deposited on Jul. 22 1992 under No. V92072202. The "strain" or isolate harbored by the LM7PC line, designated MS7PG, was deposited on Jan. 8 1993 under No. V93010816.

Starting from the cultures and isolates mentioned above, characterized by biological and morphological criteria, the next step was to endeavour to characterize the nucleic acid material associated with the viral particles produced in these cultures.

SUMMARY OF THE INVENTION

Thus, the subjects of the invention are the following:

(i) as biological material, the composition comprising two pathogenic and/or infective agents, in the isolated or purified state, associated with multiple sclerosis, namely a first agent which consists of a human virus possessing reverse transcriptase activity and related to a family of endogenous retroviral elements, or a variant of said virus, and a second agent, or a variant of said second agent, these two pathogenic and/or infective agents originating from the same viral strain chosen from the strains designated, respectively, POL-2 deposited with the ECACC on Jul. 22 1992 under Accession Number V92072202 and MS7PG deposited with the ECACC on Jan. 8 1993 under Accession Number V93010816, and from their variant strains, (ii) as biological material, the composition comprising two pathogenic and/or infective agents, in the isolated or purified state, associated with multiple sclerosis, namely a first agent consisting of a human virus possessing reverse transcriptase activity and related to a family of endogenous retroviral elements, or a variant of said virus, and a second agent, or a variant of said second agent, these two pathogenic and/or infective agents being produced by the same cell line chosen from the lines designated, respectively, PLI-2 deposited with the ECACC on Jul. 22 1992 under Accession Number 92072201 and LM7PC deposited with the ECACC on Jan. 8 1993 under Accession Number 93010817, and by all infected cell cultures capable of producing at least one or other of the pathogenic and/or infective agents, and/or their variants, (iii) the composition comprising two pathogenic and/or infective agents, in the isolated or purified state, namely a first agent consisting of a virus, or a variant of said virus, whose genome comprises a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9, their complementary sequences and their equivalent sequences, in particular the nucleotide sequences displaying, for any succession of 100 contiguous monomers, at least 50% and preferably at least 70% homology with a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID N09 and their complementary sequences, and a second pathogenic and/or infective agent whose genome comprises a nucleotide sequence chosen from SEQ ID NO10, SEQ ID NO11 and SEQ ID NO12, their complementary sequences and their equivalent sequences, in particular the nucleotide sequences displaying, for any succession of 100 contiguous monomers, at least 70% and preferably at least 90% homology with a nucleotide sequence chosen from SEQ ID NO10, SEQ ID NO11, and SEQ ID NO12, and their complementary sequences, (iv) a method for detecting a first pathogenic and/or infective agent and/or a second pathogenic and/or infective agent associated with multiple sclerosis, characterized in that at least one nucleic acid fragment is employed, namely a first fragment whose nucleotide sequence comprises a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9, their complementary sequences and their equivalent sequences, in particular the nucleotide sequences displaying, for any succession of 100 contiguous monomers, at least 50% and preferably at least 70% homology with a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9 and their complementary sequences, and/or a second fragment whose nucleotide sequence comprises a nucleotide sequence chosen from SEQ ID NO10, SEQ ID NO11, SEQ ID NO12, their complementary sequences and their equivalent sequences, in particular the nucleotide sequences displaying, for any succession of 100 contiguous monomers, at least 70% and preferably at least 90% homology with a nucleotide sequence chosen from SEQ ID NO10, SEQ ID NO11, SEQ ID NO12 and their complementary sequences, each of said fragments being, in particular, a probe, (v) a diagnostic, prophylactic or therapeutic composition, characterized in that it comprises at least one nucleic acid fragment, namely a first nucleic acid fragment whose nucleotide sequence comprises a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9, their complementary sequences and the equivalent sequences, in particular a nucleotide sequence displaying, for any succession of 100 contiguous monomers, at least 50% and preferably at least 70% homology with a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9 and their complementary sequences, and/or a second nucleic acid fragment whose nucleotide sequence comprises a nucleotide sequence chosen from SEQ ID NO10, SEQ ID NO11, SEQ ID NO12, their complementary sequences and the equivalent sequences, in particular the nucleotide sequences displaying, for any succession of 100 contiguous monomers, at least 70% and preferably at least 90% homology with a nucleotide sequence chosen from SEQ ID NO10, SEQ ID NO11, SEQ ID NO12 and their complementary sequences, (vi) a method for detecting and/or identifying a combination of pathological and/or infective agents associated with multiple sclerosis, in a biological sample, characterized in that an RNA and/or a DNA presumed to belong to at least one said pathological and/or infective agent, and/or their complementary RNA and/or DNA, is/are brought into contact with a composition comprising a first nucleotide fragment and a second nucleotide fragment, the nucleotide sequence of said first fragment comprising a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9, their complementary sequences and their equivalent sequences, in particular the nucleotide sequences displaying, for any succession of 100 contiguous monomers, at least 50% and preferably at least 70% homology with a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9 and their complementary sequences, and the nucleotide sequence of said second fragment comprising a nucleotide sequence chosen from SEQ ID NO10, SEQ ID NO11, SEQ ID NO12, their complementary sequences and their equivalent sequences, in particular the nucleotide sequences displaying, for any succession of 100 contiguous monomers, at least 70% and preferably at least 90% homology with a nucleotide sequence chosen from SEQ ID NO10, SEQ ID NO11, SEQ ID NO12 and their complementary sequences, (vii) a method for detecting, in a biological sample, a first pathological and/or infective agent and/or a second pathological and/or infective agent associated with multiple sclerosis, characterized in that a composition comprising a first polypeptide partially or completely encoded by the first nucleotide fragment defined in (vi), and/or a second polypeptide partially or completely encoded by the second nucleotide fragment also defined in (vi), is employed, (viii) a diagnostic, prophylactic or therapeutic composition, characterized in that it comprises the first polypeptide and/or the second polypeptide which are defined in (vii) above, or in that it comprises a first ligand, in particular antibody, specific for said first polypeptide, and/or a second ligand, in particular antibody, specific for said second polypeptide, (ix) a cell line designated PLI-2 as deposited with the ECACC on Jul. 22 1992 under Accession Number 92072201, or any derived cell line, or any progeny of this line, insofar as these lines and progeny are capable of producing an antibody obtained from said PLI-2 line, or any other antibody displaying an immunological cross-reaction with said antibody, (x) a viral strain designated POL-2 as deposited with the ECACC on Jul. 22 1992 under Accession Number V92072202, or any derived strain, or any progeny of this strain, insofar as these strains and progeny are capable of producing an antigen obtained from said POL-2 strain, or any other antigen displaying an immunological cross-reaction with said antigen, (xi) a cell line designated LM7PC as deposited with the ECACC on Jan. 8 1993 under Accession Number 93010817, or any derived cell line, or any progeny of this line, insofar as these lines and progeny are capable of producing an antibody obtained from said LM7PC line, or any other antibody displaying an immunological crossreaction with said antibody, (xii) a viral strain designated MS7PG as deposited with the ECACC on Jan. 8 1993 under Accession Number V93010816, or any derived strain, or any progeny of this strain, insofar as these strains and progeny are capable of producing an antigen obtained from said MS7PG strain, or any other antigen displaying an immunological cross-reaction with said antigen, (xiii) as biological material, and in the purified or isolated state, a viral material possessing reverse transcriptase activity, associated with a family of endogenous retroviral elements and associated with multiple sclerosis, originating from a viral strain possessing reverse transcriptase activity, chosen from either of the abovementioned strains POL-2 and MS7PG, and the variant strains consisting of viruses comprising at least one antigen which is recognized by at least one antibody directed against at least one corresponding antigen of one or other of the viruses of said viral strains, (xiv) as biological material, and in the purified or isolated state, a viral material possessing reverse transcriptase activity, associated with a family of endogenous retroviral elements, associated with multiple sclerosis, produced by either of the cell lines PLI-2 and LM7PC, or by any infected cell culture capable of producing a virus comprising at least one antigen which is recognized by at least one antibody directed against at least one corresponding antigen of one or other of the viruses produced by said PLI-2 and LM7PC lines, (xv) a viral material, characterized in that its genome comprises a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9, their complementary sequences and their equivalent sequences, in particular the nucleotide sequences displaying, for any succession of 100 contiguous monomers, at least 50% and preferably at least 70% homology with a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9 and their complementary sequences, (xvi) a retroviral material associated with multiple sclerosis, characterized in that the pol gene of its genome comprises an equivalent nucleotide sequence, and in particular one displaying at least 50% homology, preferably at least 65%, with a nucleotide sequence belonging to the pol gene of the ERV-9 or HSERV-9 retrovirus genome, (xvii) a retroviral material associated with multiple sclerosis, characterized in that the pol gene of its genome codes for a peptide sequence displaying at least 50% and preferably at least 70% homology with a peptide sequence encoded by the pol gene of the ERV-9 or HSERV-9 retrovirus genome, (xviii) a retroviral material associated with multiple sclerosis, characterized in that the pol gene of its genome codes for a peptide sequence displaying, for any contiguous succession of at least 30 amino acids, at least 50% and preferably at least 70% homology with a peptide sequence encoded by a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9 and their complementary sequences, (xix) a nucleotide fragment whose nucleotide sequence comprises a nucleotide sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9, their complementary sequences and their equivalent sequences, in particular the nucleotide sequences displaying, for any succession of 100 contiguous monomers, at least 50% and preferably at least 70% homology with a sequence chosen from SEQ ID NO1, SEQ ID NO2, SEQ ID NO3, SEQ ID NO4, SEQ ID NO5, SEQ ID NO6, SEQ ID NO7, SEQ ID NO8, SEQ ID NO9 and their complementary sequences, (xx) a specific primer for the amplification by polymerization of an RNA or DNA of a viral material described above, characterized in that it comprises a nucleotide sequence identical or equivalent to at least part of the nucleotide sequence of a fragment described in (xix), in particular a nucleotide sequence displaying, for any succession of 10 contiguous monomers, at least 70% homology with at least part of said fragment; a preferential primer of the invention comprises a nucleotide sequence chosen from SEQ ID NO16, SEQ ID NO17, SEQ ID NO18, SEQ ID NO19, SEQ ID NO20, SEQ ID NO21, SEQ ID NO22, SEQ ID NO23, SEQ ID NO24, SEQ ID NO25, SEQ ID NO26, SEQ ID NO31, SEQ ID NO32, SEQ ID NO33 and their complementary sequences, (xxi) a probe capable of specifically hybridizing with an RNA or DNA of a viral material described above, characterized in that it comprises a nucleotide sequence identical or equivalent to at least part of the nucleotide sequence of a fragment described in (xix), in particular a nucleotide sequence displaying, for any succession of 10 contiguous monomers, at least 70% homology with at least part of said fragment; a preferential probe according to the invention comprises a nucleotide sequence chosen from SEQ ID NO3, SEQ ID NO4, SEQ ID NO5, SEQ ID NO6, SEQ ID NO7, SEQ ID NO16, SEQ ID NO17, SEQ ID NO18, SEQ ID NO19, SEQ ID NO20, SEQ ID NO21, SEQ ID NO22, SEQ ID NO23, SEQ ID NO24, SEQ ID NO25, SEQ ID NO26, SEQ ID NO31, SEQ ID NO32, SEQ ID NO33, and their complementary sequences, (xxii) the use of a probe described in (xxi) or primer described in (xx) for detecting, separating or identifying, in a biological sample, a viral material defined above, (xxiii) a method for detecting, separating or identifying, in a biological sample, the viral material defined above, characterized in that an RNA and/or a DNA presumed to belong to said virus, and/or their complementary DNA and/or RNA, is/are brought into contact with at least one probe described in (xxi); according to an advantageous embodiment, before the RNA and/or DNA or their complementary DNA and/or RNA is/are brought into contact with the probe, said RNA and/or said DNA is/are hybridized with at least one amplification primer described in (xx), and said RNA and/or DNA is/are amplified, (xxiv) a method for quantifying, in a biological sample, the expression of a viral material, defined above, associated with multiple sclerosis, characterized in that an RNA and/or a DNA specific to said virus, and/or their complementary DNA and/or RNA, is/are brought into contact with at least one probe described in (xxi), amplification is carried out where appropriate and said RNA and/or DNA is/are detected, (xxv) as biological material, and in the isolated or purified state, a pathogenic and/or infective agent different from the viral material according to (xiii), or (xiv) or (xv) or (xvi) or (xvii) or (xix), associated with multiple sclerosis, originating from either of the abovementioned viral strains POL-2 and MS7PG, and the variant strains consisting of pathogenic and/or infective agents comprising at least one antigen which is recognized by at least one antibody directed against at least one corresponding antigen of one or other of the pathogenic and/or infective agents of said viral strains, the agents being different, respectively, from either viral material of said strains, (xxvi) as biological material, and in the isolated or purified state, a pathogenic and/or infective agent different from the viral material according to (xiii), or (xiv) or (xv) or (xvi) or (xvii) or (xix), associated with multiple sclerosis, produced by either of the abovementioned cell lines PLI-2 and LM7PC, and all infected cell cultures capable of producing a pathogenic and/or infective agent comprising at least one antigen which is recognized by at least one antibody directed against at least one corresponding antigen of one or other of the pathogenic and/or infective agents produced by said PLI-2 and LM7PC lines, the agents being, respectively, different from either viral material of said strains, (xxvii) a pathogenic and/or infective agent, characterized in that it comprises a nucleic acid comprising a nucleotide sequence chosen from SEQ ID NO10, SEQ ID NO11, SEQ ID NO12, their complementary sequences and their equivalent sequences, in particular the nucleotide sequences displaying at least 70% and preferably at least 90% homology with a nucleotide sequence comprising a sequence chosen from SEQ ID NO10, SEQ ID NO11, SEQ ID NO12 and their complementary sequences, (xxviii) a nucleotide fragment, characterized in that it comprises a nucleotide sequence chosen from SEQ ID NO10, SEQ ID NO11, SEQ ID NO12, their complementary sequences and their equivalent sequences, in particular the nucleotide sequences displaying, for any succession of 100 contiguous monomers, at least 70% and preferably at least 90% homology with a sequence chosen from SEQ ID NO10, SEQ ID NO11, SEQ ID NO12 and their complementary sequences, (xxix) a specific primer for the amplification by polymerization of an RNA or DNA of a pathogenic and/or infective agent defined in (xxv), or (xxvi) or (xxvii), characterized in that it comprises a nucleotide sequence identical or equivalent to at least part of the nucleotide sequence of a fragment described in (xxviii), in particular a nucleotide sequence displaying, for any succession of 10 contiguous monomers, at least 90% homology with at least part of said fragment; a preferential primer according to the invention comprises a nucleotide sequence chosen from SEQ ID NO13, SEQ ID NO14, SEQ ID NO15, SEQ ID NO27, SEQ ID NO28, SEQ ID NO29, SEQ ID NO30, SEQ ID NO34, SEQ ID NO35, SEQ ID NO36, SEQ ID NO37 and their complementary sequences, (xxx) a probe capable of specifically hybridizing with an RNA or DNA of a pathogenic and/or infective agent defined in (xxv), or (xxvi) or (xxvii), characterized in that it comprises a nucleotide sequence identical or equivalent to at least part of the nucleotide sequence of a fragment described in (xxviii), in particular a nucleotide sequence displaying, for any succession of 10 contiguous monomers, at least 90% homology with at least part of said fragment; a preferential probe according to the invention comprises a nucleotide sequence chosen from SEQ ID NO10, SEQ ID NO11, SEQ ID NO13, SEQ ID NO14, SEQ ID NO15, SEQ ID NO27, SEQ ID NO28, SEQ ID NO29, SEQ ID NO30, SEQ ID NO34, SEQ ID NO35, SEQ ID NO36, SEQ ID NO37 and their complementary sequences, (xxxi) the use of a probe described in (xxx) and/or a primer described in (xxix) for detecting and/or identifying, in a biological sample, a pathological and/or infective agent defined in (xxv), or (xxvi) or (xxvii), (xxxii) a method for detecting, separating or identifying, in a biological sample, the pathogenic and/or infective agent defined in (xxv), or (xxvi) or (xxvii), characterized in that an RNA and/or a DNA presumed to belong to said agent, and/or their complementary DNA and/or RNA, is/are brought into contact with at least one probe described in (xxx); according to an advantageous embodiment, before the RNA and/or DNA or their complementary DNA and/or RNA is/are brought into contact with the probe, said RNA and/or said DNA is/are hybridized with at least one amplification primer described in (xxxi), and said RNA and/or DNA is/are amplified, (xxxiii) a method for quantifying in a biological sample, the expression of an infective and/or pathogenic agent, defined in (xxv), or (xxvi) or (xxvii), associated with multiple sclerosis, characterized in that an RNA and/or a DNA specific to said agent, and/or their complementary DNA and/or RNA, is/are brought into contact with at least one probe described in (xxx), and said RNA and/or DNA is/are amplified, (xxxiv) a diagnostic, prophylactic or therapeutic composition, in particular for inhibiting the expression of at least one pathogenic and/or infective agent associated with multiple sclerosis, characterized in that it comprises at least one probe described in (xxi) or one probe described in (xxx), and/or at least one primer described in (xx) or one primer described in (xxix), (xxxv) an RNA or DNA, and in particular replication vector, comprising a fragment described in (xix) or fragment described in (xxviii), (xxxvi) a polypeptide having at least 5 and preferably 10 amino acids, encoded by any nucleotide sequence of the genome of a virus associated with multiple sclerosis, characterized in that it is encoded by at least part of a nucleotide fragment described in (xix) or a fragment described in (xxviii), (xxxvii) a diagnostic and/or therapeutic and/or prophylactic composition, characterized in that it comprises at least one polypeptide defined in (xxxvi), or in that it comprises a ligand, in particular antibody, specific for at least one said polypeptide.

Definitions

Before describing the invention in detail, different terms used in the description and the claims are now defined:

strain or isolate is understood to mean any infective and/or pathogenic biological fraction containing, for example, viruses and/or bacteria and/or parasites and generating pathogenic and/or antigenic activity, harbored by a culture or a living host; as an example, a viral strain according to the above definition can contain a coinfective agent, for example a pathogenic protist, the term "MSRV" used in the present description denotes any pathogenic and/or infective agent associated with multiple sclerosis, in particular a viral species, the attenuated strains of said viral species or the defective-interfering particles derived from this species. Viruses, and especially viruses containing RNA, are known to have a variability resulting, in particular, from relatively high rates of spontaneous mutation (28), which will be borne in mind below for defining the notion of equivalence, human viruses are understood to mean a virus capable of infecting human beings, in view of all the natural or induced variations which may be encountered when implementing the present invention, the subjects of the latter, defined above and in the claims, have been expressed including the equivalents or derivatives of the different biological materials defined below, in particular of the homologous nucleotide or peptide sequences, the variant of a virus or of a pathogenic and/or infective agent according to the invention comprises at least one antigen recognized by at least one antibody directed against at least one corresponding antigen of said virus and/or said pathogenic and/or infective agent, and/or a genome any part of which is detected by at least one hybridization probe and/or at least one nucleotide amplification primer specific for said virus and/or pathogenic and/or infective agent, such as, for example, the primers having a nucleotide sequence chosen from SEQ ID NO13 through SEQ ID NO38, and their complementary sequences, under particular hybridization conditions well known to a person skilled in the art, according to the invention, a nucleotide fragment or an oligonucleotide or polynucleotide is an arrangement of monomers, or a biopolymer, characterized by the informational sequence of the natural nucleic acids, which are capable of hybridizing with any other nucleotide fragment under predetermined conditions, it being possible for the arrangement to contain monomers of different chemical structures and to be obtained from a molecule of natural nucleic acid and/or by genetic recombination and/or by chemical synthesis, thus, a monomer can be a natural nucleotide of nucleic acid whose constituent elements are a sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or the nucleotide can be modified in at least one of the three constituent elements; as an example, the modification can occur in the bases, generating modified bases such as inosine, 5-methyldeoxycytidine, deoxyuridine, 5-(dimethylamino)deoxyuridine, 2,6-diaminopurine, 5-bromodeoxyuridine and any other modified base promoting hybridization; in the sugar, the modification can consist of the replacement of at least one deoxyribose by a polyamide (29), and in the phosphate group, the modification can consist of its replacement by esters chosen, in particular, from diphosphate, alkyl and arylphosphonate and phosphorothioate esters, "informational sequence" is understood to mean any ordered succession of monomers whose chemical nature and order in a reference direction constitute or otherwise an item of functional information of the same quality as that of the natural nucleic acids, hybridization is understood to mean the process during which, under suitable working conditions, two nucleotide fragments having sequence pairs sufficiently complementary to form a complex structure, in particular double or triple, preferably in the form of a helix, a probe comprises a nucleotide fragment synthesized chemically or obtained by digestion or enzymatic cleavage of a longer nucleotide fragment, comprising at least six monomers, advantageously from 10 to 100 monomers and preferably 10 to 30 monomers, and possessing a specificity of hybridization under particular conditions; preferably, a probe possessing fewer than 10 monomers is not used alone, but used in the presence of other probes of equally short size or otherwise; under certain special conditions, it may be useful to use probes of size greater than 100 monomers; a probe may be used, in particular, for diagnostic purposes, such molecules being, for example, capture and/or detection probes, the capture probe may be immobilized on a solid support by any suitable means, that is to say directly or indirectly, for example by covalent bonding or passive adsorption, the detection probe may be labeled by means of a label chosen, in particular, from radioactive isotopes, enzymes chosen, in particular, from peroxidase and alkaline phosphatase and those capable of hydrolyzing a chromogenic, fluorogenic or luminescent substrate, chromophoric chemical compounds, chromogenic, fluorogenic or luminescent compounds, nucleotide base analogs and biotin, the probes used for diagnostic purposes of the invention may be employed in all known hybridization techniques, and in particular the techniques termed "DOT-BLOT" (30), "SOUTHERN BLOT" (31), "NORTHERN BLOT", which is a technique identical to the "SOUTHERN BLOT" technique but which uses RNA as target, and the SANDWICH technique (32); advantageously, the SANDWICH technique is used in the present invention, comprising a specific capture probe and/or a specific detection probe, on the understanding that the capture probe and the detection probe must possess an at least partially different nucleotide sequence, the invention also covers a probe capable of hybridizing in vivo or in vitro with RNA and/or with DNA in order to block the phenomena of replication, in particular translation and/or transcription, and/or to degrade said DNA and/or RNA, a primer is a probe comprising at least six monomers, and advantageously from 10 to 30 monomers, possessing a specificity of hybridization under particular conditions for the initiation of an enzymatic polymerization, for example in an amplification technique such as PCR (Polymerase Chain Reaction), in an elongation process such as sequencing, in a method of reverse transcription or the like, two nucleotide or peptide sequences are termed equivalent or derived with respect to one another, or with respect to a reference sequence, if functionally the corresponding biopolymers can perform substantially the same role, without being identical, as regards the application or use in question, or in the technique in which they participate; two sequences are, in particular, equivalent if they are obtained as a result of natural variability, in particular spontaneous mutation of the species from which they have been identified, or induced variability, as are homologous sequences, homology being defined below, variability is understood to mean any spontaneous or induced modification of a sequence, in particular by substitution and/or insertion and/or deletion of nucleotides and/or of nucleotide fragments, and/or extension and/or shortening of the sequence at one or both ends;

an unnatural variability can result from the genetic engineering techniques used, for example the choice of synthesis primers, degenerate or otherwise, selected for amplifying a nucleic acid; this variability can manifest itself in modifications of any starting sequence, considered as reference, and capable of being expressed by a degree of homology relative to said reference sequence, homology characterizes the degree of identity of two nucleotide or peptide fragments compared; it is measured by the percentage identity which is determined, in particular, by direct comparison of nucleotide or peptide sequences, relative to reference nucleotide or peptide sequences, this percentage identity has been specifically determined for the nucleotide fragments dealt with in the present invention which are homologous with the fragments identified by SEQ ID NO1 through NO9 (MSRV-1) on the one hand, and those which are homologous with the fragments identified by SEQ ID NO10 through NO12 (MSRV-2) on the other hand, as well as for the probes and primers homologous with the probes and primers identified by SEQ ID NO16 through NO26 and SEQ ID NO31 through NO33 on the one hand, and with the probes and primers identified by SEQ ID NO13 through NO15, SEQ ID NO27 through SEQ ID NO30 and SEQ ID NO34 through NO37 on the other hand; as an example, the smallest percentage identity observed between the different general consensus sequences of nucleic acids obtained from fragments of MSRV-1 viral RNA, originating from the LM7PC and PLI-2 lines according to a protocol detailed later, is 67% in the region described in FIG. 2, any nucleotide fragment is termed equivalent to or derived from a reference fragment if it possesses a nucleotide sequence equivalent to the reference sequence; according to the above definition, the following in particular are equivalent to a reference nucleotide fragment:
   a) any fragment capable of hybridizing at least partially with the complement of the reference fragment
   b) any fragment whose alignment with the reference fragment results in the demonstration of a larger number of identical contiguous bases than with any other fragment originating from another taxonomic group
   c) any fragment resulting, or capable of resulting, from the natural variability of the species from which it is obtained
   d) any fragment capable of resulting from the genetic engineering techniques applied to the reference fragment
   e) any fragment containing at least eight contiguous nucleotides encoding a peptide which is homologous with or identical to the peptide encoded by the reference fragment,
   f) any fragment which is different from the reference fragment by insertion, deletion or substitution of at least one monomer, or extension or shortening at one or both of its ends; for example, any fragment corresponding to the reference fragment flanked at one or both of its ends by a nucleotide sequence not coding for a polypeptide, polypeptide is understood to mean, in particular, any peptide of at least two amino acids, in particular an oligopeptide or protein, extracted, separated or substantially isolated or synthesized through human intervention, in particular those obtained by chemical synthesis or by expression in a recombinant organism, polypeptide partially encoded by a nucleotide fragment is understood to mean a polypeptide possessing at least 3 amino acids encoded by at least 9 contiguous monomers included in said nucleotide fragment, an amino acid is termed analogous to another amino acid when their respective physicochemical properties, such as polarity, hydrophobicity and/or basicity and/or acidity and/or neutrality are substantially the same; thus, a leucine is analogous to an isoleucine.

any polypeptide is termed equivalent to or derived from a reference polypeptide if the polypeptides compared have substantially the same properties, and in particular the same antigenic, immunological, enzymological and/or molecular recognition properties; the following in particular are equivalent to a reference polypeptide:
   a) any polypeptide possessing a sequence in which at least one amino acid has been replaced by an analogous amino acid,
   b) any polypeptide having an equivalent peptide sequence, obtained by natural or induced variation of said reference polypeptide and/or of the nucleotide fragment coding for said polypeptide,
   c) a mimotope of said reference polypeptide,
   d) any polypeptide in whose sequence one or more amino acids of the L series are replaced by an amino acid of the D series, and vice versa,
   e) any polypeptide into whose sequence a modification of the side chains of the amino acids has been introduced, such as, for example, an acetylation of the amine functions, a carboxylation of the thiol functions, an esterification of the carboxyl functions,
   f) any polypeptide in whose sequence one or more peptide bonds have been modified, such as, for example, carba, retro, inverso, retro-inverso, reduced and methylenoxy bonds.
   (g) any polypeptide at least one antigen of which is recognized by an antibody of the reference polypeptide, the percentage identity characterizing the homology of two peptide fragments compared is, according to the present invention, at least 50% and preferably at least 70%.

In view of the fact that a virus possessing reverse transcriptase enzymatic activity may be genetically characterized equally well in RNA and in DNA form, both the viral DNA and RNA will be referred to for characterizing the sequences relating to a virus possessing such reverse transcriptase activity (MSRV-1).

In view of the fact that the pathogenic and/or infective agent (MSRV-2) has been detected both in DNA and in RNA in infected cells, it may also be characterized in DNA or RNA form.

The expressions of order used in the present description and the claims, such as "first nucleotide sequence", are not adopted so as to express a particular order, but so as to define the invention more clearly.

BRIEF DESCRIPTION OF THE DRAWINGS

A better understanding of the invention will be gained on reading the detailed description which follows, prepared with reference to the attached figures, in which:

FIG. 1 shows the MSRV-2A type sequence obtained from LM7 cultures according to the protocol of Shih (33); this sequence is identified under the reference SEQ ID NO10, FIG. 2 shows general consensus sequences of nucleic acids of the MSRV-1B sequences amplified by the PCR technique in the "pol" region, from viral DNA originating from the LM7PC and PLI-2 lines, identified under the references SEQ ID NO3, SEQ ID NO4, SEQ ID NO5 and SEQ ID NO6, and the common consensus with amplification primers bearing the reference SEQ ID NO7, FIG. 3 (comprising FIGS. 3A and 3B) shows the phylogenetic tree of the MSRV-1B type sequences obtained by PCR in the "pol" region defined by Shih (33), FIG. 4 gives the definition of a functional reading frame for each MSRV-1B/"PCR pol" type family, said families A through D being defined, respectively, by the nucleotide sequences SEQ ID NO3, SEQ ID NO4, SEQ ID NO5 and SEQ ID NO6 described in FIG. 2, FIG. 5 gives an example of consensus of the MSRV-2B sequences, identified by SEQ ID NO11, FIG. 8 shows the nucleotide sequence of the clone PSJ17 (SEQ ID NO9)

FIG. 9 shows the nucleotide sequence SEQ ID NO8 of the clone designated M003-P004, FIG. 10 shows the nucleotide sequence SEQ ID NO2 of the clone F11-1; the portion located between two arrows in the region of the primer corresponds to a variability imposed by the choice of primer which was used for the cloning of F11-1; in this same figure, the translation into amino acids is shown, FIG. 11 (comprising FIGS. 11A and 11B) shows the nucleotide sequence SEQ ID NO1, and a possible functional reading frame of SEQ ID NO1 in terms of amino acids; on this sequence, the consensus sequences of the retroviral reverse transcriptases are underlined, FIG. 12 shows the nucleotide sequence SEQ ID NO12 of the clone designated MSRV2EL1, FIG. 13 (comprising FIGS. 13A–13D), separated into three successive plates 13/18 to 15/18, shows the translation into amino acids of SEQ ID NO12, including the primer SEQ ID NO13, according to 6 possible reading frames, FIG. 14 presents an alignment of the MSRV2-A sequence (SEQ ID NO10) with the MSRV2-EL1 sequence (SEQ ID NO12); in this same diagram, the hybridization region of the primer identified under the reference SEQ ID NO13 (apart from the cloning tail) is boxed; that of the primer identified under the reference SEQ ID NO14 is indicated between square brackets, FIG. 15 gives the results of a PCR, in the form of a photograph under ultraviolet light of an ethidium bromide-impregnated agarose gel, of the amplification products obtained from the primers identified by SEQ ID NO14 and SEQ ID NO15, FIG. 16 gives the results of a PCR, in the form of a photograph under ultraviolet light of an ethidium bromide-impregnated agarose gel, of the amplification products obtained from the primers identified by SEQ ID NO16, SEQ ID NO17, SEQ ID NO18 and SEQ ID NO19. The photograph shows the result of specific MSRV-2 amplification.

FIG. 18 gives a representation in matrix form of the homology between SEQ ID NO1 of MSRV-1 and that of an endogenous retrovirus designated HSERV9; this homology of at least 65% is demonstrated by a continuous line, the absence of a line meaning a homology of less than 65%.

DETAILED DESCRIPTION OF PREFERRED EMBODIMENTS

EXAMPLE 1

Figure 3A:
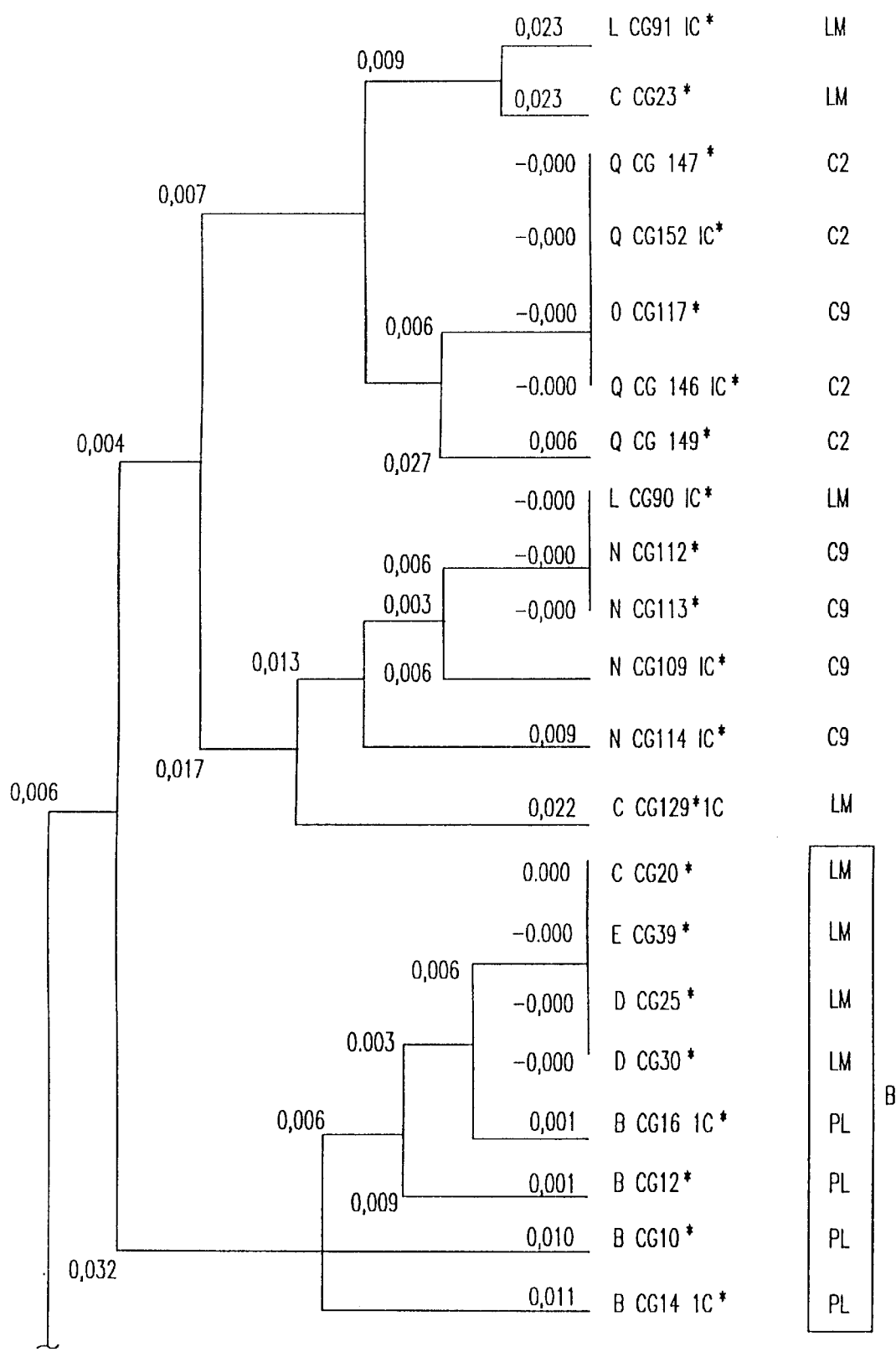

OBTAINING MSRV-2 CLONES DESIGNATED MSRV-2A, BY AMPLIFICATION OF THE CONSERVED REGIONS OF THE GENES FOR RNA-DEPENDENT DNA POLYMERASES ON A PREPARATION OF INFECTIVE AGENT PURIFIED FROM LM7 LINE CELL CULTURE

The molecular approach consisted in using a PCR technique (33) which makes it possible to amplify a relatively conserved region of the pol gene of exogenous and endogenous retroviruses, but also of viruses coding for an enzyme having reverse transcriptase (RT) activity, such as, in particular, the hepatitis B virus, and, implicitly, of any gene for RNA-dependent DNA polymerase or for an enzyme, displaying sufficient sequence homologies in the regions defined by the amplification primers used. This PCR technique was used on the nucleic acids extracted from a purified preparation of infective agent, obtained according to the protocol (34) from supernatants of the original LM7culture (24) which were kept frozen at −80° C. since that time. The fractions containing the peak of LM7-like RT activity are taken up in one volume of a buffer containing guanidine thiocyanate (35), and are stored at −80° C. until the nucleic acids are extracted according to the technique described by P. Chomzynski (35).

Prior to the PCR reaction, the RNA of the sample was transcribed into complementary DNA (cDNA) with so-called "random" primers (mixed hexanucleotides) using the "cDNA synthesis system plus" kit (Amersham) according to the manufacturer's instructions, and on the basis of an approximate value, to the nearest log factor, of the amount of RNA present in the sample.

The DNA obtained after PCR amplification of the cDNA was inserted into a plasmid using the TA Cloning® kit (British Biotechnology). The 2 µl of DNA solution were mixed with 5 µl of sterile distilled water, 1 µl of a 10-fold concentrated ligation buffer "10× LIGATION BUFFER", 2 µl of "pCR™ VECTOR" (25 ng/ml) and 1 µl of "TA DNA LIGASE". This mixture was incubated overnight at 12° C. The following steps were carried out in accordance with the instructions of the TA Cloning® kit. At the end of the procedure, the white colonies of recombinant bacteria were picked out in order to be cultured and to permit extraction of the plasmids incorporated according to the so-called "miniprep" procedure (36). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the "TA cloning kit". The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems model 373 A "Automatic Sequencer" apparatus according to the manufacturer's instructions.

The sequences obtained were then analyzed using the Mac Vector® and Geneworks® software on Genebank® computerized data bank for the nucleic acid sequences, and Swiss Prot® for the amino acid sequences deduced from the reading frames revealed in the nucleic acid sequences. Analysis of the sequences obtained from the viral sample originating from the thawed LM7 supernatants, and which was purified at the peak of reverse transcriptase activity on a sucrose gradient, revealed a majority population of clones (approximately 42% of the clones), relative to the extent of individual representation of the other sequences (always less than 5%, or 10% in a small number of cases), displaying partial homologies with known retroviruses in the expected "pol" region. This clone is designated MSRV2-A and identified by SEQ ID NO10 (see FIG. 1). The region amplified between the PCR primers is homologous with the corresponding sequence MSRV2-B identified by SEQ ID NO11 (see FIG. 5), described in Example 2. The differences observed in the sequences located at the PCR primers is explained by the use of degenerate primers in mixture form, used under different technical conditions. Interrogation of the Genebank® data bank, fully updated, did not enable an identical sequence or one displaying significant homologies to be revealed.

This sequence is presented in FIG. 1. It possesses an open reading frame in frame with the two PCR primers to be found at the ends, but it is shorter than the set of known retroviral sequences in the expected region between these primers. A deletion of 45 base pairs (15 amino acids) is observed therein following the sequence of the upstream primer, whereas the sequences preceding the downstream primer are present. However, the reading frame is open and uninterrupted over the whole of the sequence including the primers, and the deduced amino acid sequence displays a significant homology with the corresponding region of the known retroviruses. In the sequence lying inside the PCR primers, the amino acids Glu, Arg, Gln, Pro and Asp, normally fairly well conserved in this pol region of retroviruses and of known viruses with reverse transcriptase activity (33), are to be found conserved at the correct positions in the reading frame of the novel sequence.

Lastly, in view of the fact that this sequence is sufficiently divergent from the retroviral sequences already described in the data banks, it may be suggested that the sequence in question belongs to a new infective and/or pathogenic agent, designated MSRV-2A. This agent is, in principle, on the basis of the analysis of the sequences obtained, related to a retrovirus but, in view of the technique used for obtaining this sequence, it may also be an RNA virus whose genome codes for an enzyme which incidentally possesses reverse transcriptase activity, as is the case, for example, with the hepatitis B virus, HBV (33). Furthermore, the random nature of the degenerate primers used for this PCR amplification technique may very well have permitted, as a result of unforeseen sequence homologies or of conserved sites in the gene for a related enzyme, the amplification of a nucleic acid originating from a prokaryotic or eukaryotic pathogenic and/or coinfective agent (protist).

EXAMPLE 2
OBTAINING CLONES DESIGNATED MSRV-1B AND MSRV-2B, DEFINING, RESPECTIVELY, A RETROVIRUS MSRV-1 AND A COINFECTIVE AGENT MSRV2, BY "NESTED" PCR AMPLIFICATION OF THE CONSERVED POL REGIONS OF RETROVIRUSES ON VIRION PREPARATIONS ORIGINATING FROM THE LM7PC AND PLI-2 LINES

A PCR technique derived from the technique published by Shih (33) was used. This technique enables all trace of contaminant DNA to be removed by treating all the components of the reaction medium with DNase. It concomitantly makes it possible, by the use of different but overlapping primers in two successive series of PCR amplification cycles, to increase the chances of amplifying a cDNA synthesized from an amount of RNA which is small at the outset and further reduced in the sample by the spurious action of the DNAse on the RNA. In effect, the DNase is used under conditions of activity in excess which enable all trace of contaminant DNA to be removed before inactivation of this enzyme remaining in the sample by heating to 85° C. for 10 minutes. This variant of the PCR technique described by Shih (33) was used on a cDNa synthesized from the nucleic acids of fractions of infective particles purified on a sucrose gradient according to the technique described by H. Perron (34) from the "POL-2" isolate (ECACC No. V92072202) produced by the PLI-2 line (ECACC No. 92072201) on the one hand, and from the MS7PG isolate (ECACC No. V93010816) produced by the LM7PC line (ECACC No. 93010817) on the other hand. These cultures were obtained according to the methods which formed the subject of the patent applications published under Nos WO 93/20188 and WO 93/20189.

After cloning the products amplified by this technique with the TA Cloning Kit® and analysis of the sequence using the automatic sequencer as has been described in Example 1, the sequences were analyzed using the Geneworks® software on the latest available version of the Genebank® data bank.

The sequences cloned and sequenced from these samples correspond, in particular, to two types of sequence: a first type of sequence, to be found in the majority of the clones (55% of the clones originating from the POL-2 isolates of the PLI-2 culture, and 67% of the clones originating from the MS7PG isolates of the LM7PC cultures), which corresponds to a family of "pol" sequences closely similar to, but different from, the endogenous human retrovirus designated ERV-9 or HSERV-9, and a second type of sequence which corresponds to sequences very strongly homologous with the sequence attributed to an infective and/or pathogenic agent previously designated MSRV-2.

The first type of sequence, representing the majority of the clones, consists of sequences whose variability enables four subfamilies of sequences to be defined. These subfamilies are sufficiently similar to one another for it to be possible to consider them to be quasi-species originating from the same retrovirus, as is well known for the HIV-1 retrovirus (37), or to be the outcome of interference with several endogenous pro-viruses coregulated in the producing cells. These more or less defective endogenous elements are sensitive to the same regulatory signals possibly generated by a replicative provirus, since they belong to the same family of endogenous retroviruses (38). This new family of endogenous retroviruses, or alternatively this new retroviral species from which the generation of quasispecies has been obtained in culture, and which contains a consensus of the sequences described below, is designated MSRV-1B.

FIG. 2 presents the general consensus sequences of the sequences of the different MSRV-1B clones sequenced in this experiment, these sequences being identified, respectively, by SEQ ID NO3, SEQ ID NO4, SEQ ID NO5 and SEQ ID NO6. These sequences display a homology with respect to nucleic acids ranging from 70% to 88% with the HSERV9 sequence referenced X57147 and M37638 in the Genebank® data base. The phylogenetic tree of these sequences is presented in FIG. 3. In this figure, the subfamilies A, B, C and D represent the sequences which have turned up preponderantly in similar experiments repeated subsequently, in the samples of pure RNA of virions purified from the MS7PG and POL-2 isolates. From these families of sequences, four "consensus" nucleic acid sequences representative of different quasispecies of a possibly exogenous retrovirus MSRV-1B, or of different subfamilies of an endogenous retrovirus MSRV-1B, have been defined. These representative consensus sequences are presented in FIG. 4, with the translation into amino acids. A functional reading frame exists for each subfamily of these MSRV-1B sequences, and it can be seen that the functional open reading frame corresponds in each instance to the amino acid sequence appearing on the second line under the nucleic acid sequence. The general consensus of the MSRV-1B sequence, identified by SEQ ID NO7 and obtained by this PCR technique in the "pol" region, is presented in FIG. 2.

The second type of sequence representing the majority of the clones sequenced is represented by the sequence MSRV-2B presented in FIG. 5 and identified by SEQ ID NO11. The region amplified between the PCR primers is homologous, apart from a single base, with the MSRV2-A sequence (SEQ ID NO10 according to FIG. 1) lying inside the PCR primers, described in Example 1. The differences observed in the sequences corresponding to the PCR primers are explained by the use of degenerate primers in mixture form used under different technical conditions.

The sequences MSRV-2A (SEQ ID NO10) and MSRV-2B (SEQ ID NO11) are manifestly homologous, or even identical, derived from the same organism and sufficiently divergent from the retroviral sequences already described in the data banks for it to be suggested that the sequence region in question belongs to a new infective agent, designated MSRV-2. This infective agent would be, in principle, on the basis of the analysis of the first sequences obtained, related to a retrovirus but, in view of the technique used for obtaining this sequence, it could also be a DNA virus whose genome codes for an enzyme which incidentally possesses reverse transcriptase activity, as is the case, for example, with the hepatitis B virus, HBV (33). Furthermore, the random nature of the degenerate primers used for this PCR amplification technique may very well have permitted, as a result of unforeseen sequence homologies or of conserved sites in the gene for a related enzyme, the amplification of a nucleic acid originating from a prokaryotic or eukaryotic pathogenic and/or coinfective agent (protist).

Figure 6:
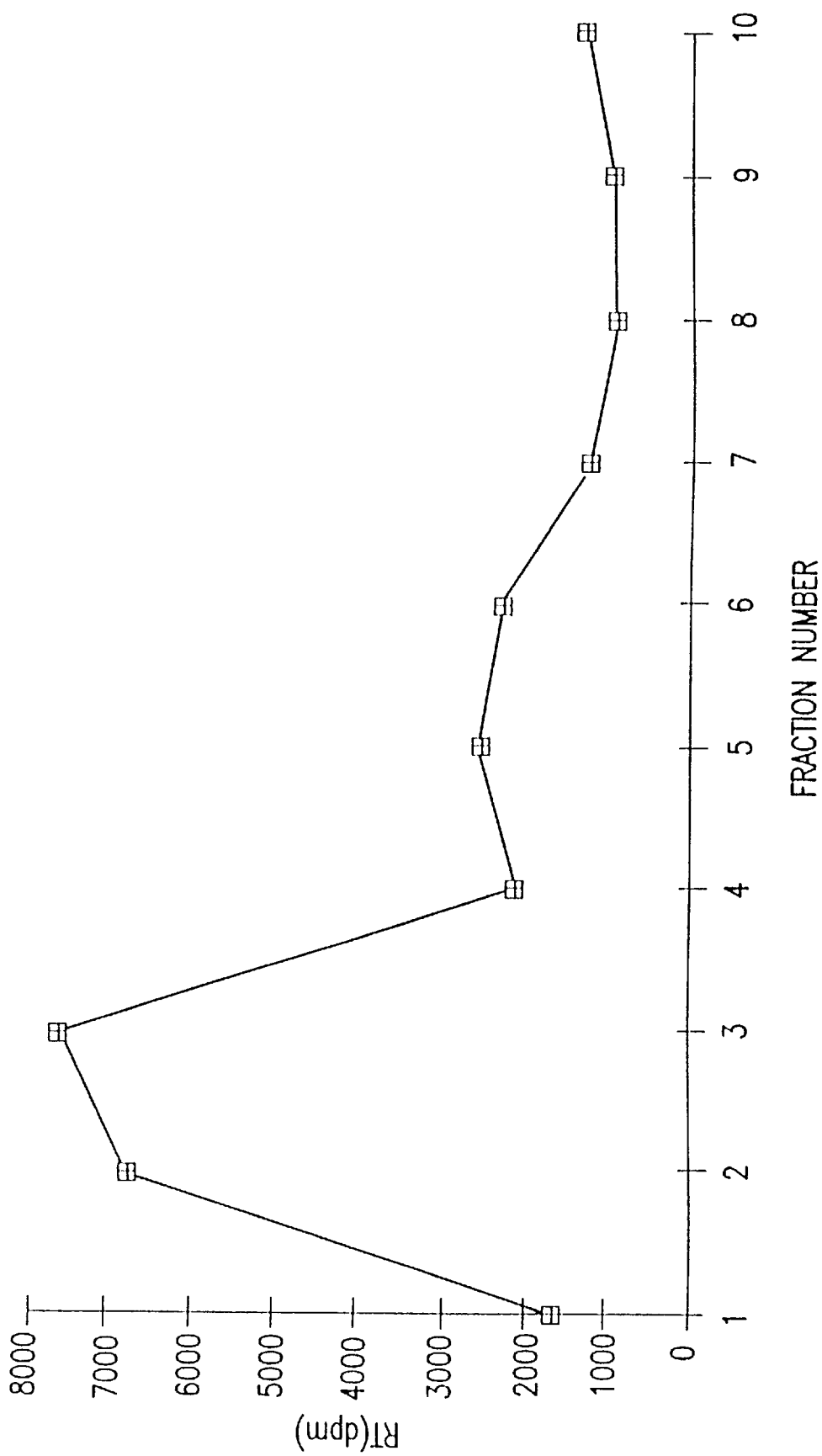
FIG. 6 is a representation of the reverse transcriptase (RT) activity in dpm (disintegrations per minute) in the sucrose fractions taken from a purification gradient of the virions produced by the B lymphocytes in culture from a patient suffering from MS, FIG. 7 gives, under the same conditions as in FIG. 6, the assay of the reverse transcriptase activity in the culture of a B lymphocyte line obtained from a control free from multiple sclerosis.
Figure 7:
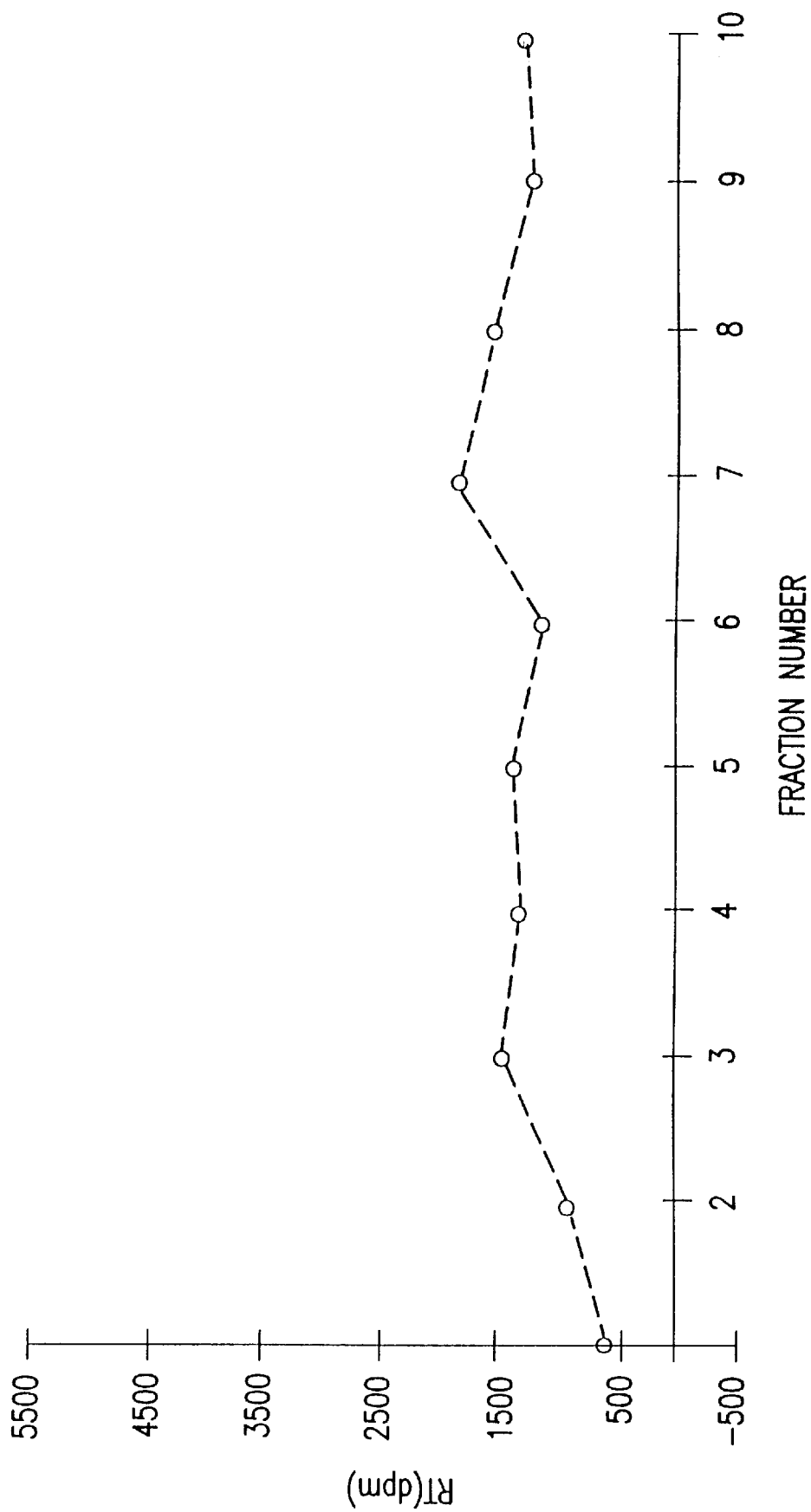

EXAMPLE 3
OBTAINING CLONES DESIGNATED MSRV-1B AND MSRV-2B, DEFINING A FAMILY MSRV-1 and MSRV2, BY "NESTED" PCR AMPLIFICATION OF THE CONSERVED POL REGIONS OF RETROVIRUSES ON PREPARATIONS OF B LYMPHOCYTES FROM A NEW CASE OF MS The same PCR technique, modified according to the technique of Shih (33), was used to amplify and sequence the RNA nucleic acid material present in a purified fraction of virions at the peak of "LM7-like" reverse transcriptase activity on a sucrose gradient according to the technique described by H. Perron (34), and according to the protocols mentioned in Example 2, from a spontaneous lymphoblastoid line obtained by self-immortalization in culture of B lymphocytes from an MS patient who was seropositive for the Epstein-Barr virus (EBV), after setting up the blood lymphoid cells in culture in a suitable culture medium containing a suitable concentration of cyclosporin A. A representation of the reverse transcriptase activity in the sucrose fractions taken from a purification gradient of the virions produced by this line is presented in FIG. 6. Similarly, the culture supernatants of a B line obtained under the same conditions from a control free from multiple sclerosis were treated under the same conditions, and the assay of reverse transcriptase activity in the sucrose gradient fractions proved negative throughout (background), and is presented in FIG. 7. Fraction 3 of the gradient corresponding to the MS B line and the same fraction without reverse transcriptase activity of the non-MS control gradient were analyzed by the same RT-PCR technique as before, derived from Shih (33), followed by the same steps of cloning and sequencing as described in Examples 1 and 2.

It is particularly noteworthy that the MSRV-1 and MSRV-2 type sequences are to be found only in the material associated with a peak of "LM7-like" reverse transcriptase activity originating from the MS B lymphoblastoid line. These sequences were not to be found with the material from the control (non-MS) B lymphoblastoid line in 26 recombinant clones taken at random. Only Mo-MuLV type contaminant sequences, originating from the commercial reverse transcriptase used for the cDNA synthesis step, and sequences without any particular retroviral analogy were to be found in this control, as a result of the "consensus" amplification of homologous polymerase sequences which is produced by this PCR technique. Furthermore, the absence of a concentrated target which competes for the amplification reaction in the control sample permits the amplification of dilute contaminants. The difference in results is manifestly highly significant (chi-squared, $p<0.001$).

EXAMPLE 4
OBTAINING A CLONE PSJ17, DEFINING A RETROVIRUS MSRV-1, BY REACTION OF ENDOGENOUS REVERSE TRANSCRIPTASE WITH A VIRION PREPARATION ORIGINATING FROM THE PLI-2 LINE.

This approach is directed towards obtaining reverse-transcribed DNA sequences from the supposedly retroviral RNA in the isolate using the reverse transcriptase activity present in this same isolate. This reverse transcriptase activity can theoretically function only in the presence of a retroviral RNA linked to a primer tRNA or hybridized with short strands of DNA already reverse-transcribed in the retroviral particles (39). Thus, the obtaining of specific retroviral sequences in a material contaminated with cellular nucleic acids was optimized according to these authors by means of the specific enzymatic amplification of the portions of viral RNAs with a viral reverse transcriptase activity. To this end, the authors determined the particular physico-chemical conditions under which this enzymatic activity of reverse transcription on RNAs contained in virions could be effective in vitro. These conditions correspond to the technical description of the protocols presented below (endogenous RT reaction, purification, cloning and sequencing).

The molecular approach consisted in using a preparation of concentrated but unpurified virion obtained from the culture supernatants of the PLI-2 line, prepared according to the following method: the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virion. This concentrated but unpurified viral sample was used to perform a so-called endogenous reverse transcription reaction as will now be described: a volume of 200 μl of virion purified according to the protocol described above, and containing a reverse transcriptase activity of approximately 1–5 million dpm, is thawed at 37° C. until a liquid phase appears, and then placed on ice. A 5-fold concentrated buffer was prepared with the following components: 500 mM Tris-HCl pH 8.2; 75 mM NaCl; 25 mM MgCl$_2$; 75 mM DTT and 0.10% NP 40. 100 μl of 5× buffer +25 μl of a 100 mM solution of DATP+25 μl of a 100 mM solution of dTTP+25 μl of a 100 mM solution of dGTP +25 μl of a 100 mM solution of dCTP+100 μl of sterile distilled water+200 μl of the virion suspension (RT activity of 5 million DPM) in PBS were mixed and incubated at 42° C. for 3 hours. After this incubation, the reaction mixture is added directly to a buffered phenol/chloroform/isoamyl alcohol mixture (Sigma ref. P 3803); the aqueous phase is collected and one volume of sterile distilled water is added to the organic phase to reextract the residual nucleic acid material. The collected aqueous phases are combined, and the nucleic acids contained are precipitated by adding 3M sodium acetate pH 5.2 to $\frac{1}{10}$ volume+2 volumes of ethanol+1 μl of glycogen (Boehringer-Mannheim ref. 901 393) and placing the sample at –20° C. for 4 h or overnight at +4° C. The precipitate obtained after centrifugation is then washed with 70% ethanol and resuspended in 60 ml of distilled water. The products of this reaction were then purified, cloned and sequenced according to the protocol which will now be described: blunt-ended DNAs with unpaired adenines at the ends were generated: a "filling-in" reaction was first performed: 25 μl of the previously purified DNA solution were mixed with 2 μl of a 2.5 mM solution containing, in equimolar amounts, dATP+dGTP+dTTP+dCTP/1 μl of T4 DNA polymerase (Boehringer-Mannheim ref. 1004 786)/5 μl of 10× "incubation buffer for restriction enzyme" (Boehringer-Mannheim ref. 1417 975)/1 μl of a 1% bovine serum albumin solution/16 μl of sterile distilled water. This mixture was incubated for 20 minutes at 11° C. 50 μl of TE buffer and 1 μl of glycogen (Boehringer-Mannheim ref. 901 393) were added thereto before extraction of the nucleic acids with phenol/chloroform/isoamyl alcohol (Sigma ref. P 3803) and precipitation with sodium acetate as described above. The DNA precipitated after centrifugation is resuspended in 10 μl of 10 mM Tris buffer pH 7.5. 5 μl of this suspension were then mixed with 20 μl of 5× Taq buffer, 20 μl of 5 mM dATP, 1 μl (5U) of Taq DNA polymerase (Amplitaq™) and 54 μl of sterile distilled water. This mixture is incubated for 2 h at 75° C. with a film of oil on the surface of the solution. The DNA suspended in the aqueous solution drawn off under the film of oil after incubation is precipitated as described above and resuspended in 2 μl of sterile distilled water. The DNA obtained was inserted into a plasmid using the TA cloning kit™. The 2 μl of DNA solution were mixed with 5 μl of sterile distilled water, 1 μl of a 10-fold concentrated ligation buffer "10× LIGATION BUFFER", 2 μl of "pCR™ VECTOR" (25 ng/ml) and 1 μl of "TA DNA LIGASE". This mixture was incubated overnight at 12° C. The following steps were carried out according to the instructions of the TA Cloning® kit (British Biotechnology). At the end of the procedure, the white colonies of recombinant (white) bacteria were picked out in order to be cultured and to permit extraction of the plasmids incorporated according to the so-called "miniprep" procedure (36). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA cloning kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "model 373 A Automatic Sequencer" apparatus according to the manufacturer's instructions.

Discriminating analysis on the computerized data banks of the sequences cloned from the DNA fragments present in the reaction mixture enabled a retroviral type sequence to be revealed. The corresponding clone PSJ17 was completely sequenced, and the sequence obtained, presented in FIG. 8 and identified by SEQ ID NO9, was analyzed using the Geneworks® software on the updated "Genebank®" data banks. An identical sequence already described could not be found by analysis of the data banks. Only a partial homology with some known retroviral elements was to be found. The most useful relative homology relates to an endogenous retrovirus designated ERV-9, or HSERV-9, depending on the references (40).

EXAMPLE 5

PCR AMPLIFICATION OF THE NUCLEIC ACID SEQUENCE CONTAINED BETWEEN THE 5' REGION DEFINED BY THE CLONE "POL MSRV-1B" AND THE 3' REGION DEFINED BY THE CLONE PSJ17.

Five oligonucleotides, M001, M002-A, M003-BCD, P004 and P005, were defined in order to amplify the RNA originating from purified POL-2 virions. Control reactions were performed so as to check for the presence of contaminants (reaction with water). The amplification consists of an RT-PCR step according to the protocol described in Example 2, followed by a "nested" PCR according to the PCR protocol described in the document EP-A-0569272. In the first RT-PCR cycle, the primers M001 and P004 or P005 are used. In the second PCR cycle, the primers M002-A or M003-BCD and the primer P004 are used. The primers are positioned as follows:

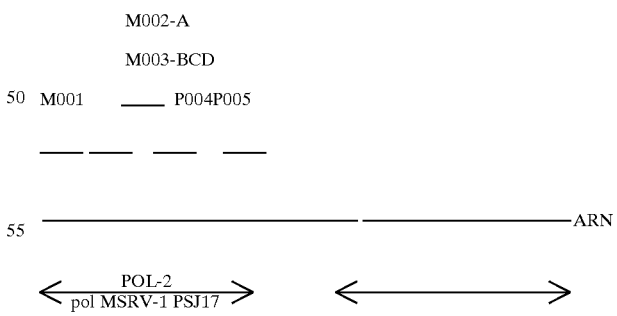

Their composition is:
primer M001: GGTCITICCICAIGG (SEQ ID NO20)
primer M002-A: TTAGGGATAGCCCTCATCTCT (SEQ ID NO21)
primer M003-BCD: TCAGGGATAGCCCCCATCTAT (SEQ ID NO22)
primer P004: AACCCTTTGCCACTACATCAATTT (SEQ ID NO23)

primer P005: GCGTAAGGACTCCTAGAGCTATT (SEQ ID NO24)

The "nested" amplification product obtained, and designated M003-P004, is presented in FIG. 9, and corresponds to the sequence SEQ ID NO8.

EXAMPLE 6
AMPLIFICATION AND CLONING OF A PORTION OF THE MSRV-1 RETROVIRAL GENOME USING A SEQUENCE ALREADY IDENTIFIED, IN A SAMPLE OF VIRUS PURIFIED AT THE PEAK OF REVERSE TRANSCRIPTASE ACTIVITY

A PCR technique derived from the technique published by Frohman (41) was used. The technique derived makes it possible, using a specific primer at the 3' end of the genome to be amplified, to elongate the sequence towards the 5' region of the genome to be analyzed. This technical variant is described in the documentation of the firm "Clontech Laboratories Inc., (Palo-Alto Calif., USA) supplied with its product "5'-AmpliFINDER™ RACE Kit", which was used on a virion fraction purified as described above.

The specific 3' primers used in the kit protocol for the synthesis of the cDNA and the PCR amplification are, respectively, complementary to the following MSRV-1 sequences:

cDNA:TCATCCATGTACCGAAGG (SEQ ID NO25)

amplification:ATGGGGTTCCCAAGTTCCCT (SEQ ID NO26)

The products originating from the PCR were purified after purification on agarose gel according to conventional methods (36), and then resuspended in 10 ml of distilled water. Since one of the properties of Taq polymerase consists in adding an adenine at the 3' end of each of the two DNA strands, the DNA obtained was inserted directly into a plasmid using the TA Cloning kit™ (British Biotechnology). The 2 µl of DNA solution were mixed with 5 µl of sterile distilled water, 1 µl of a 10-fold concentrated ligation buffer "10× LIGATION BUFFER", 2 µl of "pCR™ VECTOR" (25 ng/ml) and 1 µl of "TA DNA LIGASE". This mixture was incubated overnight at 12° C. The following steps were carried out according to the instructions of the TA Cloning® kit (British Biotechnology). At the end of the procedure, the white colonies of recombinant (white) bacteria were picked out in order to be cultured and to permit extraction of the plasmids incorporated according to the so-called "miniprep" procedure (36). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning Kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "model 373 A automatic sequencer" apparatus according to the manufacturer's instructions.

This technique was applied first to two fractions of virion purified as described below on sucrose from the "POL-2" isolate produced by the PLI-2 line on the one hand, and from the MS7PG isolate produced by the LM7PC line on the other hand: the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virions. The concentrated virus is then applied to a sucrose gradient in sterile PBS buffer (15 to 50% weight/weight) and ultracentrifuged at 35,000 rpm (100,000 g) for 12 h at +4° C. in a swing-out rotor. 10 fractions are collected, and 20 µl are withdrawn from each fraction after homogenization to assay the reverse transcriptase activity therein according to the technique described by H. Perron (24). The fractions containing the peak of "LM7-like" RT activity are then diluted in sterile PBS buffer and ultracentrifuged for one hour at 35,000 rpm (100,000 g) to sediment the viral particles. The pellet of purified virion thereby obtained is then taken up in a small volume of a buffer which is appropriate for the extraction of RNA. The cDNA synthesis reaction mentioned above is carried out on this RNA extracted from purified extracellular virion. PCR amplification according to the technique mentioned above enabled the clone F1-11 to be obtained, whose sequence, identified by SEQ ID NO2, is presented in FIG. 10.

This clone makes it possible to define, with the different clones previously sequenced, a region representative of the "pol" gene of the MSRV-1 retrovirus, as presented in FIG. 11. This sequence, designated SEQ ID NO1, is reconstituted from different clones overlapping one another at their ends, correcting the artifacts associated with the primers and with the amplification or cloning techniques which would artificially interrupt the reading frame of the whole.

In FIG. 11, the potential reading frame with its translation into amino acids is presented below the nucleic acid sequence.

EXAMPLE 7
CAPTURE, AMPLIFICATION AND CLONING OF A PORTION OF THE MSRV-2 GENOME USING A SEQUENCE ALREADY IDENTIFIED, IN A CULTURE INFECTED WITH MSRV-2

The supernatants of a cell culture expressing "LM7-like" reverse transcriptase activity similar to that described by H. Perron (24) were collected regularly over several weeks and stored frozen at −80° C. after adding 10% of glycerol. The set of supernatants was then thawed so as to concentrate the infective particles by ultra-centrifugation and to purify them by centrifugation to equilibrium on a sucrose gradient; the reverse transcriptase activity was then measured in the different fractions collected on the gradient according to the methodology described by H. Perron (34).

The different fractions representing the peak of reverse transcriptase activity were pooled so as to extract the nucleic acids therefrom according to a protocol intended for the purification of RNA (35), but the nucleic acids extracted were not treated with DNase. A PCR amplification derived from the technique described by Shih (33) was performed directly on this nucleic acid sample not treated with DNase, according to an RNA amplification method as described in the document EP-A-0,569,272, in a total volume of 100 µl containing 200 ng of RNA, 1 µl of RNA Guard and 33 µmol of each mixture of primers (MOP) which are described by Shih (33) and identical to those used for the direct (DNA) PCR; 0.25 mM each dNTP, 10 µl of 10× buffer, 2.5 u of Tag enzyme and 0.4 µl of RT enzyme (RT-AMV; 10 u) are also added to the samples. The amplification cycles are carried out as follows: denaturation of the RNA 65° C./10 minutes, synthesis of the cDNA 50° C./8 minutes, then the cycles are identical to those of the PCR described by Shih (33). Control reactions were performed so as to check for the absence of contaminants (reaction with water). The products were analyzed on 10% acrylamide gel.

The samples amplified by RT-PCR were then cloned and sequenced according to the techniques described in Example 1.

The majority of the clones sequenced from the RT-PCR product corresponds to the MSRV-2A sequence and its equivalent MSRV-2B described above in Examples 1 to 3.

Moreover, after removal of the artifactual sequences, the other clones sequenced prove to correspond to MSRV-1 type sequences as are described in Examples 1 to 3.

After verification of the sequences present in this nucleic acid material originating from these purified fractions containing infective particles, at least a part of which is associated with reverse transcriptase activity, the remaining nucleic acid material was used to perform a specific capture of nucleic acids carrying the MSRV2 sequence previously identified and described in Examples 1 to 3.

In a prior step, the genetic material carrying the MSRV2 sequence was amplified by a one-directional PCR technique of 50 cycles using a single primer. This primer is coupled to a biotin molecule at its 3' end, permits one-directional amplification from 3' to 5' and corresponds to the following sequence identified under SEQ ID NO38:

5' TAAAGATCTAGAATTCGGCTATAGGCG-GCATCCGGCAACT 3'

Thereafter, capture was performed in solution with magnetic beads coupled to avidin (Dynabeads®) according to the instructions of the manufacturer (Dynal) and, after a series of washes at room temperature enabling nucleic acids not coupled to a biotin to be removed, a PCR was performed directly on these washed beads with a specific primer at the 3' end and a primer at the 5' end provided by a solution of oligonucleotide of 10 bases (10-mer) with a random sequence.

The specific amplification primer oriented from 3' to 5' corresponds to the sequence identified by SEQ ID NO13:

5' GCATCCGGCAACTGCACG 3'

The PCR performed at 35° C. over 40 cycles with these primers enabled the genetic material specifically biotinylated by the first PCR step and captured on the Dynabeads® beads to be amplified. After cloning with the "TA cloning" kit of the DNA amplified by this second PCR step and sequencing of the recombinant clones, according to the techniques described in Example 1, a sequence of 748 base pairs was obtained. This nucleic acid sequence SEQ ID NO12 is presented in FIG. 12. This elongated sequence will be designated hereafter MSRV-2EL1.

The reverse sequence complementary to the primer SEQ ID NO13 is present at the 3' end and is boxed in FIG. 12. Upstream of this primer, the sequence already identified in the MSRV-2A and MSRV-2B clones is to be found.

Figure 13B:
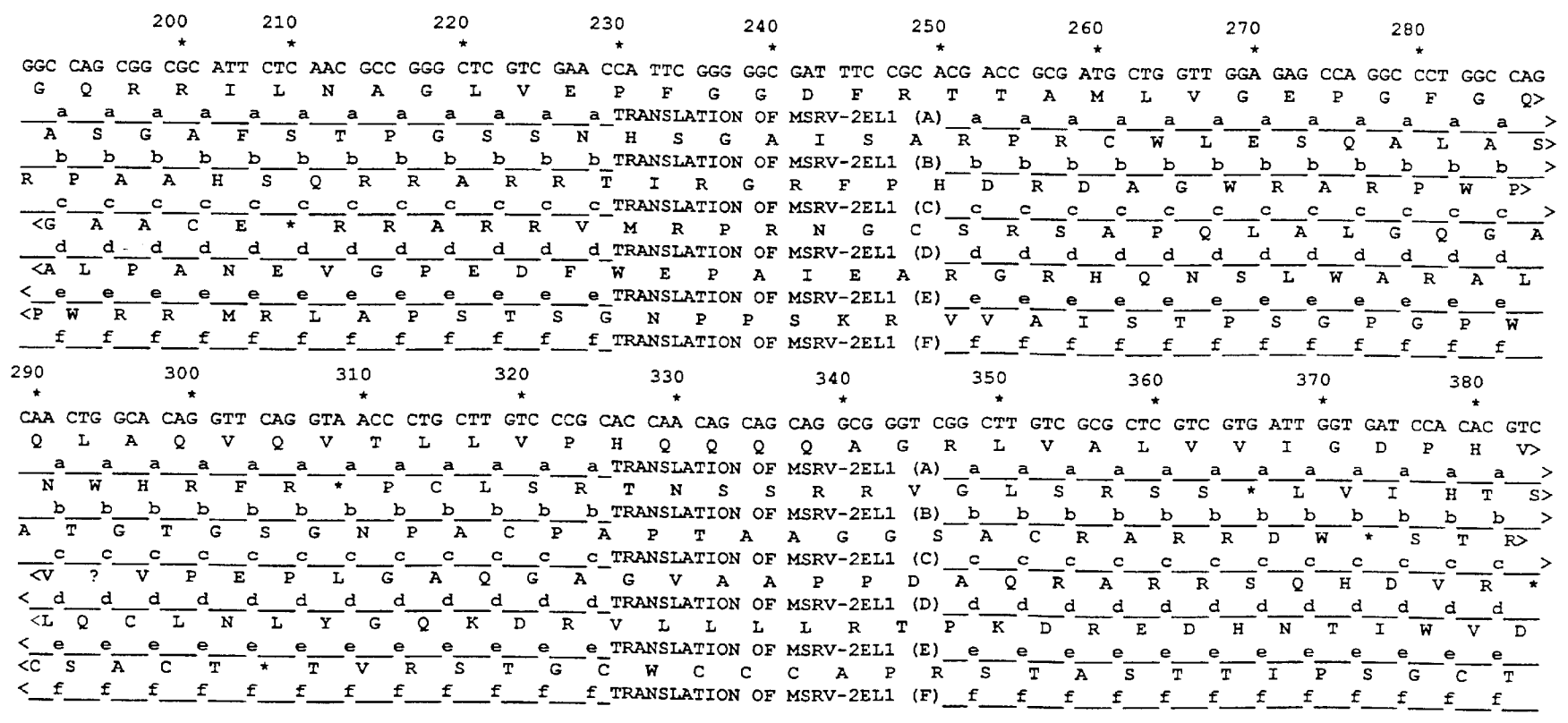
Figure 13C:
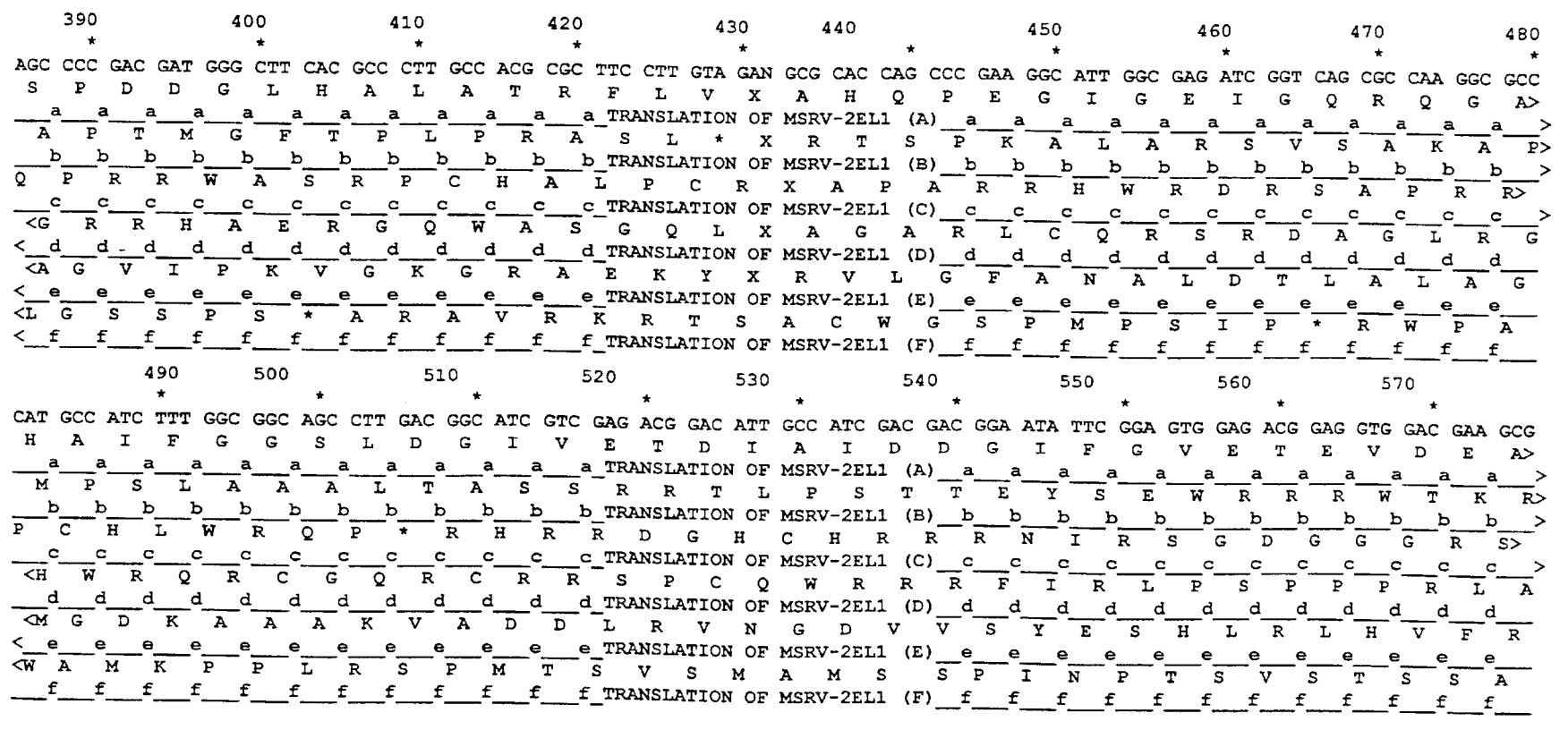
Figure 13D:
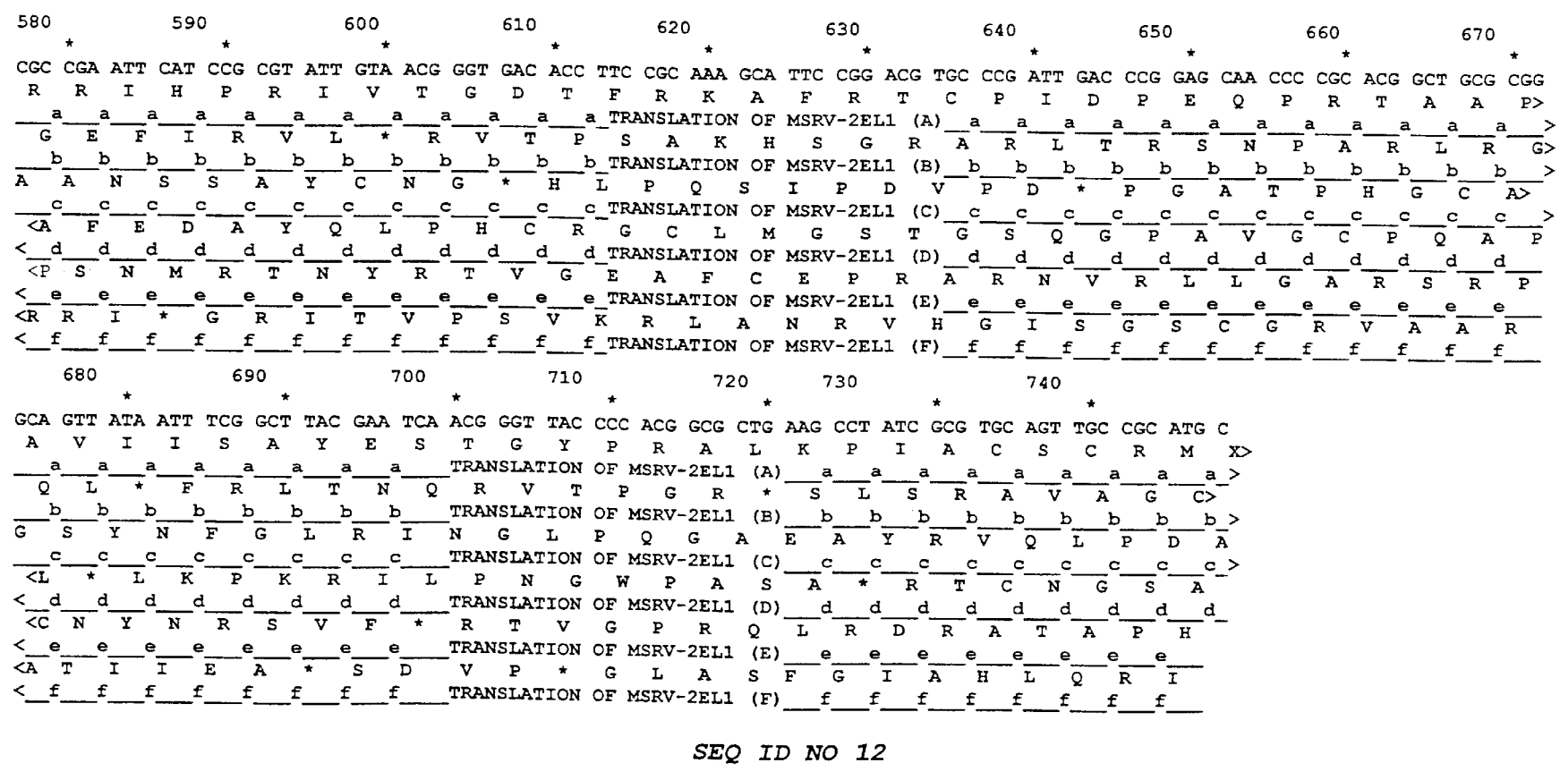
Figure 13A:
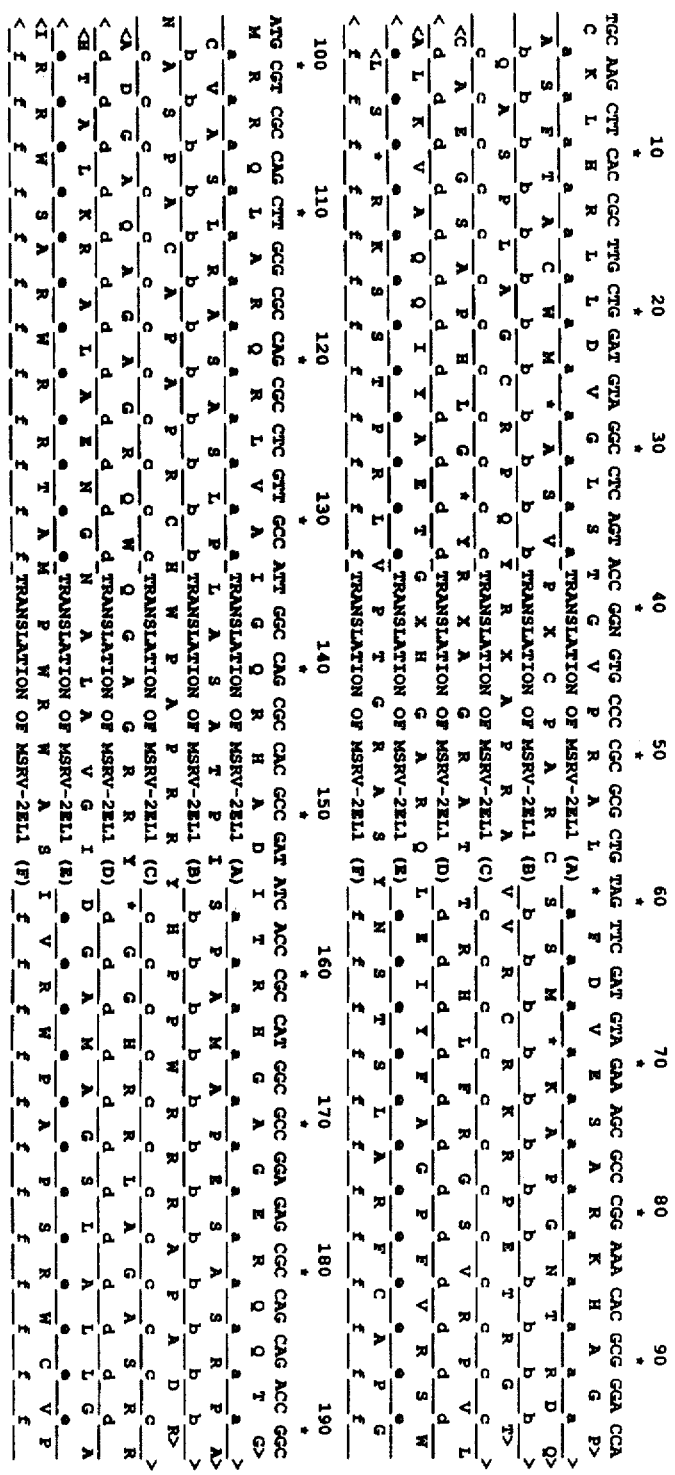

The translation of this sequence into amino acids according to the 6 possible reading frames is presented in FIG. 13.

An alignment of the MSRV2-A sequence (SEQ ID NO10) with the MSRV-2EL1 sequence (SEQ ID NO12) is presented in FIG. 14. It will be noted that the MSRV-2A sequence is strictly identical to the elongated sequence, apart from a few differences in the region corresponding to the degenerate primers used for obtaining MSRV-2A. This region is underlined in this figure; moreover, the hybridization region of the primer SEQ ID NO13 (apart from the cloning tail) is boxed, that of the primer SEQ ID NO14 is presented between square brackets. The true sequence of the MSRV-2 genome in this region is probably that of MSRV-2EL1, where it has not been imposed by hybridized primers having low stringency as is the case for MSRV-2A (and MSRV-2B likewise).

The MSRV-2EL1 sequence hence corresponds to a new sequenced region of the MSRV-2 genome. This was verified using new PCR primers defined in MSRV-2EL1 and MSRV-2A, which permitted a specific amplification on the nucleic acids used for the cloning described in this example.

The examples which follow present different results of specific MSRV2 amplifications which confirm the relationship with the presence of corresponding infective agent in the cell cultures described, to permit the isolation of an LM7 type virus (24), and also, in vivo, in patients suffering from MS.

The result of interrogation of the Genebank® data bank, updated in August 1994, with the MSRV-2EL1 sequence does not show any significant homology with genetic sequences known to date. However, the interrogation of the possible translations into amino acids according to the 6 potential reading frames of this MSRV-2EL1 sequence shows partial homologies with bacterial, viral or cellular sequences.

The absence of PCR amplification with specific primers on normal human DNA shows that the sequence in question is not one of cellular origin. MSRV-2 is hence an infective agent exogenous to man. However, the degenerate nature of the mixtures of primers used according to variants of the technique described by Shih (33), which enabled the first sequence elements designated MSRV-2A and MSRV-2B to be identified, may have permitted the unforeseen amplification of a genome not belonging to a retrovirus, or even to a gene coding for an RNA-dependent DNA polymerase. The almost invariable co-detection of MSRV-1 in cultures originating from MS and expressing reverse transcriptase activity may be explained by a pathological association between two different agents, at least one of which is a retrovirus (MSRV-1).

The detection in patients of these two types of sequence described in the examples which follow corroborates a pathological association. However, only one of these elements may suffice to explain the pathology induced in MS.

EXAMPLE 8
DETECTION OF SPECIFIC MSRV-2 SEQUENCES IN DIFFERENT SAMPLES OF HUMAN CELLS ORIGINATING FROM PATIENTS SUFFERING FROM MS OR FROM CONTROLS

The MSRV-2EL1 sequence (SEQ ID NO12) enabled several pairs of oligonucleotide primers which could be used for the amplification of specific DNA or RNA by the PCR technique to be defined.

The primers defined below enabled a specific detection of the MSRV-2 genome in different human cells to be carried out by an RT-PCR step according to an RNA amplification method as described in the document EP-A-0,569,272.

The primers used are the following:
5' primer, identified by SEQ ID NO14
    5'GTAGTTCGATGTAGAAAGCG 3'
3' primer, identified by SEQ ID NO15
    5'GCATCCGGCAACTGCACG 3'

The PCR is performed according to a succession of 35 cycles linking together, after the cDNA synthesis step, 1 min at 94° C., 1 min at 54° C. and 1 min at 72° C.

The total RNA extracted from different cell types (35), without DNase treatment, was used in this RT-PCR reaction.

Figure 15:
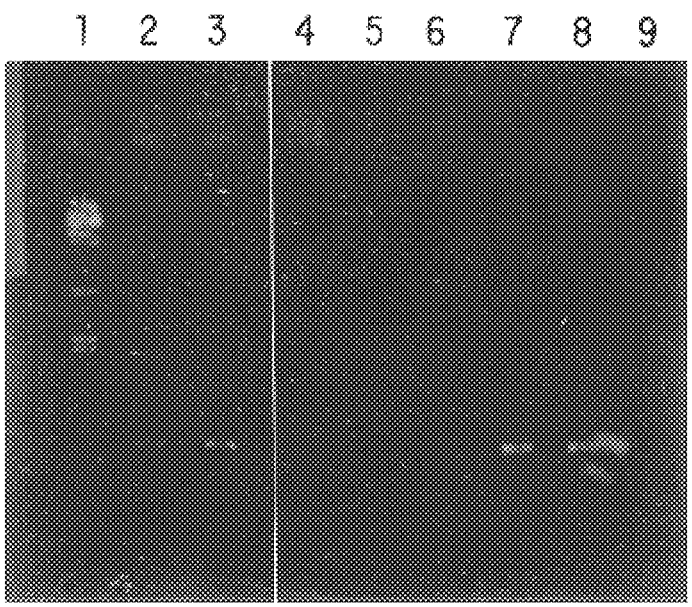

FIG. 15 presents the results of PCR using a photograph under ultraviolet light of an ethidium bromide-impregnated agarose gel, in which an electrophoresis of PCR amplification products applied separately to the different wells was performed.

Well number 1 contains a mixture of DNA molecular weight markers, and wells 2 to 9 represent, in order, the products amplified from the total RNAs of the following cells:

2—LM7PC (ECACC No. 93010817);
3—PLI2 (ECACC No. 92072201);
4—human medulloblastoma cells;
5—MRC-5 (human embryonic lung fibroblasts);
6—human blood mononuclear cells from a healthy donor;
7—cells originating from a mixture of B lymphoblastoid lines derived from the peripheral blood of different patients suffering from MS;
8—cells originating from a B lymphoblastoid line derived from the peripheral blood of a patient suffering from MS;
9—control not containing nucleic acids ("water" control).

The existence of a band of specific DNA of approximately 700 base pairs, corresponding to the expected size, which is amplified in the samples originating from patients suffering from MS (LM7PC, PLI2, B lymphocyte lines) and not in the cells tested originating from controls not suffering from MS (MRC5, blood mononuclear cells and medulloblastoma cells), can be seen.

EXAMPLE 9
DETECTION OF SPECIFIC MSRV-1 and MSRV-2 SEQUENCES IN DIFFERENT SAMPLES OF PLASMA ORIGINATING FROM PATIENTS SUFFERING FROM MS OR FROM CONTROLS.

A PCR technique similar to the one described in Example 8 was used to detect the MSRV-1 and MSRV-2 genomes in plasmas obtained after taking blood samples from patients suffering from MS and from non-MS controls onto EDTA.

Extraction of the RNAs from plasma was performed according to a technique described by P. Chomzynski (35), after adding one volume of buffer containing guanidinium thiocyanate to 1 ml of plasma stored frozen at −80° C. after collection.

For MSRV-2, the PCR was performed under the same conditions and with the same primers as those described in Example 8.

However, similar results were also obtained with the following PCR primers in two successive amplifications by "nested" PCR on samples of nucleic acids not treated with DNase.

The primers used for this first step of 40 cycles with a hybridization temperature of 48° C. are the following:
5' primer, identified by SEQ ID NO27
5' GCCGATATCACCCGCCATGG 3', corresponding to a 5' MSRV-2 PCR primer, for a first PCR on patients' sample,
3' primer, identified by SEQ ID NO28
5' GCATCCGGCAACTGCACG 3', corresponding to a 3' MSRV-2 PCR primer, for a first PCR on patients' sample After this step, 10 μl of the amplification product are taken and used to carry out a second, so-called "nested" PCR amplification with primers located within the region already amplified. This second step takes place over 35 cycles, with a primer hybridization ("annealing") temperature of 50° C. The reaction volume is 100 μl.

The primers used for this second step are the following:
5' primer, identified by SEQ ID NO29
5' CGCGATGCTGGTTGGAGAGC 3', corresponding to a 5' MSRV-2 PCR primer, for a nested PCR on patients' sample,
3' primer, identified by SEQ ID NO30
5' TCTCCACTCCGAATATTCCG 3', corresponding to a 3' MSRV-2 PCR primer, for a nested PCR on patients' sample.

For MSRV-1, the amplification was performed in two steps. Furthermore, the nucleic acid sample is treated beforehand with DNase, and a control PCR without RT (AMV reverse transcriptase) is performed on the two amplification steps so as to verify that the RT-PCR amplification comes exclusively from the MSRV-1 RNA. In the event of a positive control without RT, the initial aliquot sample of RNA is again treated with DNase and amplified again.

The protocol for treatment with DNase lacking RNAse activity is as follows: the extracted RNA is aliquoted in the presence of "RNAse inhibitor" (Boehringer-Mannheim) in water treated with DEPC at a final concentration of 1 μg in 10 μl; to these 10 μl, 1 μl of "RNAse-free DNAse" (Boehringer-Mannheim) and 1.2 μl of pH 5 buffer containing 0.1M sodium acetate and 5 mM $MgSO^4$ are added; the mixture is incubated for 15 min at 20° C. and brought to 95° C. for 1.5 min in a "thermocycler".

The first MSRV-1 RT-PCR step is performed according to a variant of the RNA amplification method as described in Patent Application No. EP 0,569,272 A1. In particular, the cDNA synthesis step is performed at 42° C. for one hour; the PCR amplification takes place over 40 cycles, with a primer hybridization ("annealing") temperature of 53° C. The reaction volume is 100 μl.

The primers used for this first step are the following:
5' primer, identified by SEQ ID NO16
5' AGGAGTAAGGAAACCCAACGGAC 3'
3' primer, identified by SEQ ID NO17
5' TAAGAGTTGCACAAGTGCG 3'

After this step, 10 μl of the amplification product are taken and used to carry out a second, so-called "nested" PCR amplification with primers located within the region already amplified. This second step takes place over 35 cycles, with a primer hybridization ("annealing") temperature of 53° C. The reaction volume is 100 μl.

The primers used for this second step are the following:
5' primer, identified by SEQ ID NO18
5' TCAGGGATAGCCCCCATCTAT 3'
3' primer, identified by SEQ ID NO19
5' AACCCTTTGCCACTACATCAATTT 3'.

Figure 16:

FIG. 16 presents the results of PCR in the form of a photograph under ultraviolet light of an ethidium bromide-impregnated agarose gels, in which an electrophoresis of the PCR amplification products applied separately to the different wells was performed.

The photograph shows the result of specific MSRV-2 amplification:
well number 8 contains a mixture of DNA molecular weight markers, and wells 1 to 7 represent, in order, the products amplified from the total RNAs of plasmas originating from 4 healthy controls free from MS (wells 1 to 4) and from 3 patients suffering from MS at different stages of the disease (wells 5 to 7).

In this series, MSRV-2 nucleic acid material is detected in the plasma of one case of MS out of the 3 tested, and in none of the 4 control plasmas. Other results obtained on more extensive series confirm these results.

Figure 17:
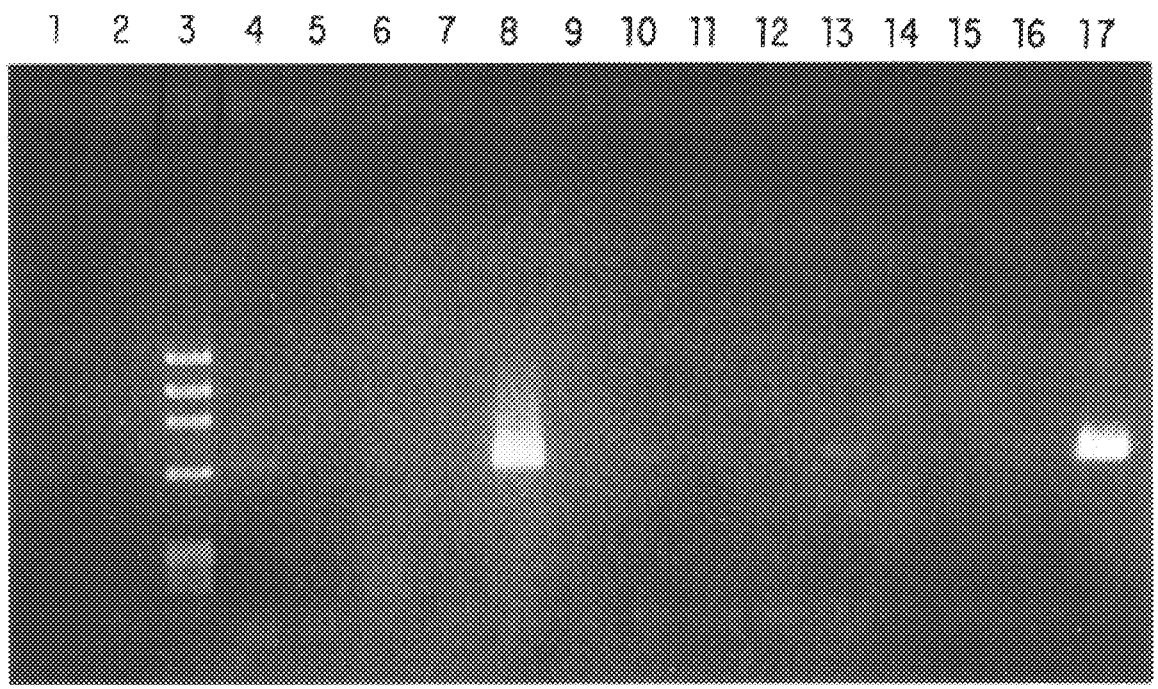
FIG. 17 also gives the results of a PCR, in the form of a photograph under ultraviolet light of an ethidium bromide-impregnated agarose gel, of the amplification products obtained from the primers identified by SEQ ID NO 16, SEQ ID NO 17, SEQ ID NO 18 and SEQ ID NO 19. The photograph shows the results of specific amplification by MSRV-1 "nested" RT-PCR.

FIG. 17 shows the result of specific amplification by MSRV-1 "nested" RT-PCR:
well No. 1 contains the PCR product produced with water alone, without the addition of AMV reverse transcriptase; well No. 2 contains the PCR product produced with water alone, with addition of AMV reverse transcriptase; well number 3 contains a mixture of DNA molecular weight markers; wells 4 to 13 contain, in order, the products amplified from the total RNAs extracted from sucrose gradient fractions (collected in a downward direction), on which gradient a pellet of virion originating from a supernatant of a culture infected with MSRV-1 and MSRV-2 was centrifuged to equilibrium according to the protocol described by Perron (34); to well 14 nothing was applied; to wells 15 to 17, the amplified products of RNA extracted from plasmas originating from 3 different patients suffering from MS at different stages of the disease were applied.

The MSRV-1 retroviral genome is indeed to be found in the sucrose gradient fraction containing the peak of reverse transcriptase activity measured according to the technique described by H. Perron (24), with a very strong intensity (fraction 5 of the gradient, deposited in well No. 8). A slight amplification has taken place in the first fraction (well No. 4), probably corresponding to RNA released by lysed particles which floated at the surface of the gradient; similarly, aggregated debris sedimented in the last fraction (tube bottom), carrying with it a few copies of the MSRV-1 genome which have given rise to an amplification of low intensity.

Of the 3 MS plasmas tested in this series, MSRV-1 RNA turned up in one case, producing a very intense amplification (well No. 17).

In this series, the MSRV-1 retroviral RNA genome, probably corresponding to particles of extracellular virus present in the plasma in extremely small numbers, was detected by "nested" RT-PCR in one case of MS out of the 3 tested. Other results obtained on more extensive series confirm these results.

Furthermore, the specificity of the sequences amplified by these PCR techniques may be verified and evaluated by the "ELOSA" technique as described by F. Mallet (42) and in the document FR-2,663,040.

Figure 3B:
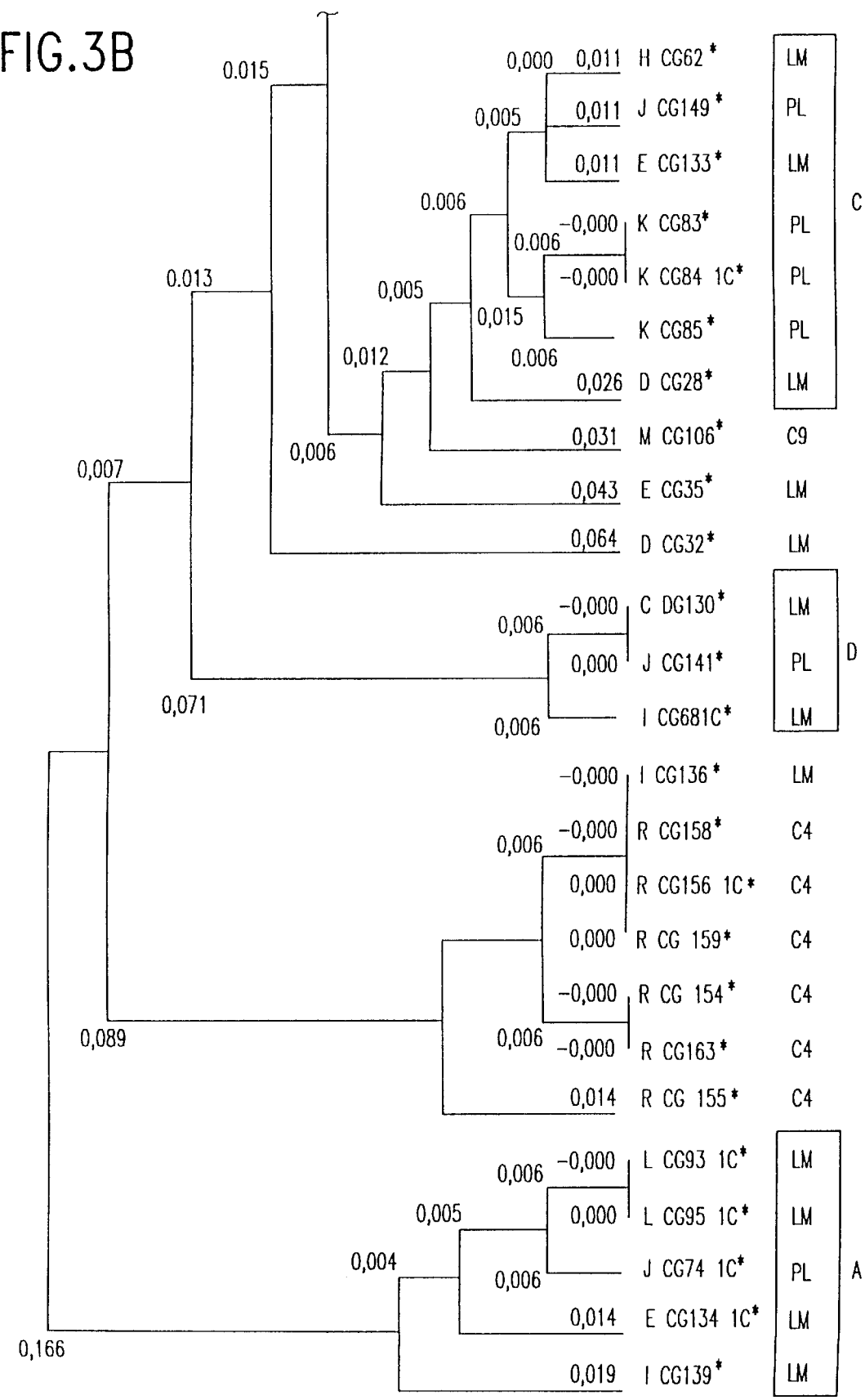

For MSRV-1, the products of the nested PCR described above may be tested in two ELOSA systems enabling a consensus A and a consensus B+C+D of MSRV-1 to be detected separately, corresponding to the subfamilies described in Example 2 and FIGS. 2, 3 and 4. In effect, the sequences closely resembling the consensus B+C+D are to be found essentially in the RNA samples originating from MSRV-1 virions purified from cultures or amplified in extracellular biological fluids of MS patients, whereas the sequences closely resembling the consensus A are essentially to be found in normal human cellular DNA.

The ELOSA/MSRV-1 system for the capture and specific hybridization of the PCR products of the subfamily A uses a capture oligonucleotide cpV1A with an amine bond at the 5' end and a biotinylated detection oligonucleotide dpV1A having as their sequence, respectively:

cpV1A identified by SEQ ID NO31
  5' GATCTAGGCCACTTCTCAGGTCCAGS 3', corresponding to the ELOSA capture oligonucleotide for the products of MSRV-1 nested PCR performed with the primers identified by SEQ ID NO16 and SEQ ID NO17, optionally followed by amplification with the primers identified by SEQ ID NO18 and SEQ ID NO19 on samples from patients.

dpV1A identified by SEQ ID NO32
  5' CATCTITTTGGICAGGCAITAGC 3' corresponding to the ELOSA detection oligonucleotide for the subfamily A of the products of MSRV-1 nested PCR performed with the primers identified by SEQ ID NO16 and SEQ ID NO17, optionally followed by amplification with the primers identified by SEQ ID NO18 and SEQ ID NO19 on samples from patients.

The ELOSA/MSRV-1 system for the capture and specific hybridization of the PCR products of the subfamily B+C+D uses the same biotinylated detection oligonucleotide dpV1A and a capture oligonucleotide cpV1B with an amine bond at the 5' end having as its sequence:

dpV1B identified by SEQ ID NO33
  5' CTTGAGCCAGTTCTCATACCTGGA 3', corresponding to the ELOSA capture oligonucleotide for the subfamily B+C+D of the products of MSRV-1 nested PCR performed with the primers identified by SEQ ID NO16 and SEQ ID NO17, optionally followed by amplification with the primers identified by SEQ ID NO18 and SEQ ID NO19 on samples from patients.

This ELOSA detection system enabled it to be verified that none of the PCR products thus amplified from DNase-treated plasmas of MS patients contained a sequence of the subfamily A, and that all were positive with the consensus of the subfamilies B, C and D.

For MSRV-2, a similar ELOSA technique was evaluated on isolates originating from infected cell cultures, using the following PCR amplification primers, 5' primer, identified by SEQ ID NO34
  5' AGTGYTRCCMCARGGCGCTGAA 3', corresponding to a 5' MSRV-2 PCR primer, for PCR on sample from cultures, 3' primer, identified by SEQ ID NO35
  5' GMGGCCAGCAGSAKGTCATCCA 3', corresponding to a 3' MSRV-2 PCR primer, for PCR on sample from cultures, and the capture oligonucleotides with an amine bond at the 5' end cpV2 and the biotinylated detection oligonucleotide dpV2 having as their respective sequences:

cpV2 identified by SEQ ID NO36
  5' GGATGCCGCCTATAGCCTCTAC 3', corresponding to an ELOSA capture oligonucleotide for the products of MSRV-2 PCR performed with the primers SEQ ID NO34 and SEQ ID NO35, or optionally with the degenerate primers defined by Shih (33), dpV2 identified by SEQ ID NO37
  5' AAGCCTATCGCGTGCAGTTGCC 3', corresponding to an ELOSA detection oligonucleotide for the products of MSRV-2 PCR performed with the primers SEQ ID NO34 and SEQ ID NO35, or optionally with the degenerate primers defined by Shih (33) This PCR amplification system with a pair of primers different from those which were described previously for amplification on the samples from patients made it possible to confirm the infection with MSRV-2 of in vitro cultures and of samples of nucleic acids used for the molecular biology studies.

All things considered, our first results of PCR detection of the genome of pathogenic and/or infective agents, it is possible that free "virus" may circulate in the blood stream of patients in an acute, virulent phase, outside the nervous system. This is compatible with the almost invariable presence of "gaps" in the blood-brain barrier of patients in an active phase of MS.

It is thus already conceivable, as a result of the discoveries made and the methods developed by the inventors, to carry out a diagnosis of MSRV-1 and/or MSRV-2 infection and/or reactivation and to evaluate a therapy in MS on the basis of its efficacy to "negative" the detection of these agents in the patients' biological fluids. Furthermore, early detection in individuals not yet displaying neurological signs of MS could make it possible to institute a treatment which would be all the more effective with respect to the subsequent clinical course for the fact that it would precede the lesion stage which corresponds to the onset of neurological disorders. Now, at the present time, a diagnosis of MS cannot be established before a symptomatology of neurological lesions has set in, and hence no treatment is instituted before the emergence of a clinical picture suggestive of lesions of the central nervous system which are already significant. The diagnosis of an MSRV-1 and/or MSRV-2 infection and/or reactivation in man is hence of decisive importance, and the present invention provided the means of doing this.

It is thus possible, apart from carrying out a diagnosis of MSRV-1 and/or MSRV-2 infection and/or reactivation, to evaluate a therapy in MS on the basis of its efficacy to "negative" the detection of these agents in the patients' biological fluids. BIBLIOGRAPHY (1) Norrby E., Prog. Med. Virol., 1978; 24, 1–39
(2) Johnson R. T., "Handbook of clinical neurology, 47 Demyelinating diseases", Vinken P. and Bruyn G. W., eds. Amsterdam, Elsevier Science Publishing, 1985, 319–336
(3) Cook 1980
(4) Rosati 1988
(5) Riisse 1991
(6) Elian 1990
(7) Lisak R. P. and Zweiman B., New Engl. J. Med. 1977; 297, 850–853
(8) Lassnamnn H. and Wisniewski H. M., Arch. Neurol. 1979; 36, 490–497
(9) Eirayama M. et al., Neurology 1986; 36, 276–278
(10) Kenneth G. W. et al., Annals of Neurology 1986; 20, 20–25
(11) Suzumura A. et al., Journal of Neuroimmunology 1986; 11, 137–147
(12) Tourtelotte W. et al., Journal of Neurochemistry 1986; 46, 1086–1093
(13) Field E. J., The Lancet 1989, I, 1272
(14) Fujinamn R. S. and Oldstone M. B. A., "Molecular mimicry: Cross-reactivity between microbes and host proteins as a cause of autoimmunity" Oldstone M. B. A., ed. Current Topics in Microbiology and Immunology, vol. 145, Berlin, Springer-Verlag, 1989
(15) Rudge P., Journal of Neurology, Neurosurgery and Psychiatry 1991; 54, 853–855
(16) Gessain A. et al., J. Infect. Disease 1988; 1226–1234
(17) Koprowski H. et al., Nature 1985; 318, 154
(18) Ohta M. et al., J. Immunol. 1986; 137, 3440
(19) Reddy E. P. et al., Science 1989; 243, 529
(20) Greenberg S. J. et al., Proc. Natl. Acad. Sci. USA 1989; 86, 2878
(21) Richardson J. H. et al., Science 1989; 246, 821
(22) Hauser S. L. et al., Nature 1986; 322, 176
(23) Karpas A. et al., Nature 1986; 322, 177
(24) Perron E. et al., Res. Virol. 1989, 140, 551–561
(25) Perron H. et al., "Current concepts in multiple sclerosis" Wietholter et al., eds. Amsterdam, Elsevier, 1991, 111–116
(26) Perron H. et al., The Lancet 1991, 337, 862–863
(27) Perron H. et al., J. Gen. Virol. 1993, 74, 65–72(28) Fields and Knipe, Fundamental Virology 1986, Rev Press N.Y.
(29) Nielsen P. E. et al., Science 1991; 254, 1497–1500
(30) Maniatis et al., Molecular Cloning, Cold Spring Harbor, 1982
(31) Southern. E. M., J. Mol. Biol. 1975, 98, 503
(32) Dunn A. R. and Hassel J. A., Cell 1977, 12, 23
(33) Shih et al., J. Virol. 1989, 63, 64–75
(34) Perron H. et al., Res. Vir. 1992, 143, 337–350
(35) Chomzynski P. and N. Sacchi, Analytical Biochemistry 1987, 162, 156–159
(36) Sambrook J., Fritsch E. F., and Maniatis T., Molecular cloning, a laboratory manual. Cold Spring Harbor Laboratory Press, 1989
(37) Meyerhans et al., Cell 1989, 58, 901–910
(38) Linial M. L. and Miller A. D., "Current topics in microbiology and immunobiology. Retroviruses, strategies of replication" vol. 157, 125–152; Swanstrom R. and Vogt P. K., eds., Springer-Verlag, Heidelberg 1990
(39) Lori F. et al., J. Virol. 1992, 66, 5067–5074
(40) La Mantia et al., Nucleic Acids Research 1991, 19, 1513–1520
(41) Frogman et al., Proc. Natl. Acad. Sci. USA 1988, 85, 8998–9002
(42) F. Mallet et al., Journal of Clinical Microbiology 1993; 31, 1444–1449

What is claimed is:

1. An isolated virus comprising a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and complementary sequences complementary thereto.

2. The isolated virus according to claim 1, wherein the nucleotide sequence is SEQ ID NO: 1 or a sequence complementary thereto.

3. The isolated virus according to claim 1, wherein the nucleotide sequences is SEQ ID NO: 2 or a sequence complementary thereto.

4. The isolated virus according to claim 1, wherein the nucleotide sequences is SEQ ID NO: 3 or a sequence complementary thereto.

5. The isolated virus according to claim 1, wherein the nucleotide sequences is SEQ ID NO: 4 or a sequence complementary thereto.

6. The isolated virus according to claim 1, wherein the nucleotide sequences is SEQ ID NO: 5 or a sequence complementary thereto.

7. The isolated virus according to claim 1, wherein the nucleotide sequences is SEQ ID NO: 6 or a sequence complementary thereto.

8. The isolated virus according to claim 1, wherein the nucleotide sequences is SEQ ID NO: 7 or a sequence complementary thereto.

9. The isolated virus according to claim 1, wherein the nucleotide sequences is SEQ ID NO: 8 or a sequence complementary thereto.

10. The isolated virus according to claim 1, wherein the nucleotide sequences is SEQ ID NO: 9 or a sequence complementary thereto.

* * * * *

UNITED STATES PATENT AND TRADEMARK OFFICE
CERTIFICATE OF CORRECTION

PATENT NO. : 5,871,745
DATED : February 16, 1999
INVENTOR(S) : Herve Perron, Francois Mallet, Bernard Mandrand, Frederic Bedin and Frederic Beseme It is certified that error appears in the above-identified patent and that said Letters Patent is hereby corrected as shown below:

Please substitute attached Figures 8, 11A, 11B, 12, 13A, 13B and 13D for patented Figures 8, 11A, 11B, 12, 13A, 13B, and 13D.

Signed and Sealed this

Twelfth Day of February, 2002

Attest:

JAMES E. ROGAN
Attesting Officer        Director of the United States Patent and Trademark Office

FIG. 8

```
CAAGCCACCC  AAGAACTCTT  AAATTTCCTC  ACTACCTGTG  GCTACAAGGT   50
TTCCAAACCA  AAGGCTCAGC  TCTGCTCACA  GGAGATTAGA  TACTTAGGGT  100
TAAAATTATC  CAAAGGCACC  AGGGGCCTCA  GTGAGGAACG  TATCCAGCCT  150
ATACTGGGTT  ATCCTCATCC  CAAAACCCTA  AAGCAACTAA  GAGGGTTCCT  200
TAGCATGATC  AGGTTTCTGC  CGAAAACAAG  ATTCCCAGGT  ACAACCAAAA  250
TAGCCAGACC  ATTATATACA  CTAATTAAGG  AAACTCAGAA  AGCCAATACC  300
TATTTAGTAA  GATGGACACC  TAAACAGAAG  GCTTCCAGG   CCCTAAAGAA  350
GGCCCTAACC  CAAGCCCCAG  TGTTCAGCTT  GCCAACAGGG  CAAGATTTTT  400
CTTTATATGG  CACAGAAAAA  ACAGGAATCG  CTCTAGGAGT  CCTTACACAG  450
GTCCGAGGGA  TGAGCTTGCA  ACCCGTGGCA  TACCTGAATA  AGGAAATTGA  500
TGTAGTGGCA  AAGGGTTGGC  CTCATNGTTT  ATGGGTAATG  GNGGCAGTAG  550
CAGTCTNAGT  ATCTGAAGCA  GTTAAAATAA  TACAGGGAAG  AGATCTTNCT  600
GTGTGGACAT  CTCATGATGT  GAACGGCATA  CTCACTGCTA  AAGGAGACTT  650
GTGGTTGTCA  GACAACCATT  TACTTAANTA  TCAGGCTCTA  TTACTTGAAG  700
AGCCAGTGCT  GNGACTGCGC  ACTTGTGCAA  CTCTTAAACC  C           741
```

SEQ ID NO 9

FIG. 11A

```
        10         20         30         40         50         60         70
         *          *          *          *          *          *          *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R>
 a   a   a   a   a   a   a   a   TRANSLATION OF MSRV-1 POL  (A)  a   a   a   a   a   a   a   a >

80         90        100        110        120        130        140
         *          *          *          *          *          *          *
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I   P>
 a   a   a   a   a   a   a   a   TRANSLATION OF MSRV-1 POL  (A)  a   a   a   a   a   a   a   a >

150        160        170        180        190        200        210
         *          *          *          *          *          *          *
GAG GAA GCA GAG TGG TTT ACA GTC CTG GAC CTT AAG GAT GCC TTT TTC TGC ATC CCT GTA CGT CCT GAC TCT
 E   E   A   E   W   F   T   V   L   D   L   K   D   A   F   F   C   I   P   V   R   P   D   S>
 a   a   a   a   a   a   a   a   TRANSLATION OF MSRV-1 POL  (A)  a   a   a   a   a   a   a   a >

220        230        240        250        260        270        280
         *          *          *          *          *          *          *
CAA TTC TTG TTT GCC TTT GAA GAT CCT TTG AAC CCA ACG TCT CAA CTC ACC TGG ACT|GTT TTA CCC CAA GGG|
 Q   F   L   F   A   F   E   D   P   L   N   P   T   S   Q   L   T   W   T | V   L   P   Q   G>
 a   a   a   a   a   a   a   a   TRANSLATION OF MSRV-1 POL  (A)  a   a   a   a   a   a   a   a >

290        300        310        320        330        340        350        360
         *          *          *          *          *          *          *          *
TTC AGG GAT AGC CCC CAT CTA TTT GGC CAG GCA TTA GCC CAA GAC TTG AGT CAA TTC TCA TAC CTG GAC ACT
 F   R   D   S   P   H   L   F   G   Q   A   L   A   Q   D   L   S   Q   F   S   Y   L   D   T>
 a   a   a   a   a   a   a   a   TRANSLATION OF MSRV-1 POL  (A)  a   a   a   a   a   a   a   a >

370        380        390        400        410        420        430
         *          *          *          *          *          *          *
CTT GTC CTT CAG|TAC ATG GAT GAT|TTA CTT TTA GTC GCC CGT TCA GAA ACC TTG TGC CAT CAA GCC ACC CAA
 L   V   L   Q | Y   M   D   D | L   L   L   V   A   R   S   E   T   L   C   H   Q   A   T   Q>
 a   a   a   a   a   a   a   a   TRANSLATION OF MSRV-1 POL  (A)  a   a   a   a   a   a   a   a >

440        450        460        470        480        490        500
         *          *          *          *          *          *          *
GAA CTC TTA ACT TTC CTC ACT ACC TGT GGC TAC AAG GTT TCC AAA CCA AAG GCT CGG CTC TGC TCA CAG GAG
 E   L   L   T   F   L   T   T   C   G   Y   K   V   S   K   P   K   A   R   L   C   S   Q   E>
 a   a   a   a   a   a   a   a   TRANSLATION OF MSRV-1 POL  (A)  a   a   a   a   a   a   a   a >

510        520        530        540        550        560        570
         *          *          *          *          *          *          *
ATT AGA TAC TNA GGG CTA AAA TTA TCC AAA GGC ACC AGG GCC CTC AGT GAG GAA CGT ATC CAG CCT ATA CTG
 I   R   Y   X   G   L   K   L   S   K   G   T   R   A   L   S   E   E   R   I   Q   P   I   L>
 a   a   a   a   a   a   a   a   TRANSLATION OF MSRV-1 POL  (A)  a   a   a   a   a   a   a   a >

580        590        600        610        620        630        640
         *          *          *          *          *          *          *
GCT TAT CCT CAT CCC AAA ACC CTA AAG CAA CTA AGA GGG TTC TTG GCA ATA ACA GGT TTC TGC CGA AAA CAG
 A   Y   P   H   P   K   T   L   K   Q   L   R   G   F   L   G   I   T   G   F   C   R   K   Q>
 a   a   a   a   a   a   a   a   TRANSLATION OF MSRV-1 POL  (A)  a   a   a   a   a   a   a   a >

650        660        670        680        690        700        710        720
         *          *          *          *          *          *          *          *
ATT CCC AGG TAC ASC CCA ATA GCC AGA CCA TTA TAT ACA CTA ATT ANG GAA ACT CAG AAA GCC AAT ACC TAT
 I   P   R   Y   X   P   I   A   R   P   L   Y   T   L   I   X   E   T   Q   K   A   N   T   Y>
 a   a   a   a   a   a   a   a   TRANSLATION OF MSRV-1 POL  (A)  a   a   a   a   a   a   a   a >

730        740        750        760        770        780        790
         *          *          *          *          *          *          *
TTA GTA AGA TGG ACA CCT ACA GAA GTG GCT TTC CAG GCC CTA AAG AAG GCC CTA ACC CAA GCC CCA GTG TTC
 L   V   R   W   T   P   T   E   V   A   F   Q   A   L   K   K   A   L   T   Q   A   P   V   F>
 a   a   a   a   a   a   a   a   TRANSLATION OF MSRV-1 POL  (A)  a   a   a   a   a   a   a   a >
```

FIG. 11B

```
          800         810         820         830         840         850         860
           *           *           *           *           *           *           *
    AGC TTG CCA ACA GGG CAA GAT TTT TCT TTA TAT GCC ACA GAA AAA ACA GGA ATA GCT CTA GGA GTC CTT ACG
     S   L   P   T   G   Q   D   F   S   L   Y   A   T   E   K   T   G   I   A   L   G   V   L   T>
    __a___a___a___a___a___a___a____TRANSLATION OF MSRV-1 POL    (A)___a___a___a___a___a___a___a__>

870         880         890         900         910         920         930
           *           *           *           *           *           *           *
    CAG GTC TCA GGG ATG AGC TTG CAA CCC GTG GTA TAC CTG AGT AAG GAA ATT GAT GTA GTG GCA AAG GGT TGG
     Q   V   S   G   M   S   L   Q   P   V   V   Y   L   S   K   E   I   D   V   V   A   K   G   W>
    __a___a___a___a___a___a___a____TRANSLATION OF MSRV-1 POL    (A)___a___a___a___a___a___a___a__>

940         950         960         970         980         990        1000
           *           *           *           *           *           *           *
    CCT CAT NGT TTA TGG GTA ATG GNG GCA GTA GCA GTC TNA GTA TCT GAA GCA GTT AAA ATA ATA CAG GGA AGA
     P   H   X   L   W   V   M   X   A   V   A   V   X   V   S   E   A   V   K   I   I   Q   G   R>
    __a___a___a___a___a___a___a____TRANSLATION OF MSRV-1 POL    (A)___a___a___a___a___a___a___a__>

1010        1020        1030        1040        1050        1060        1070        1080
     *           *           *           *           *           *           *           *
    GAT CTT NCT GTG TGG ACA TCT CAT GAT GTG AAC GGC ATA CTC ACT GCT AAA GGA GAC TTG TGG TTG TCA GAC
     D   L   X   V   W   T   S   H   D   V   N   G   I   L   T   A   K   G   D   L   W   L   S   D>
    __a___a___a___a___a___a___a____TRANSLATION OF MSRV-1 POL    (A)___a___a___a___a___a___a___a__>

1090        1100        1110        1120        1130        1140        1150
           *           *           *           *           *           *           *
    AAC CAT TTA CTT AAN TAT CAG GCT CTA TTA CTT GAA GAG CCA GTG CTG NGA CTG CGC ACT TGT GCA ACT CTT
     N   H   L   L   X   Y   Q   A   L   L   L   E   E   P   V   L   X   L   R   T   C   A   T   L
    __a___a___a___a___a___a___a____TRANSLATION OF MSRV-1 POL    (A)___a___a___a___a___a___a___a__>

AAA CCC
     K   P>
    __a__>
```

SEQ ID NO 1

FIG. 12

```
         10              20        30              40
          *               *         *               *
   TGCAAGCTTCACCGC  TTGCTGGATGTAGGC   CTCAGTACCGGNGTG
         50     60         70              80        90
          *      *          *               *         *
   CCCCGCGCGCTGTAG  TTCGATGTAGAAAGC   GCCCGGAAACACGCG
              100           110       120         130
               *             *         *           *
   GGACCAATGCGTCGC  CAGCTTGCGCGCCAG   CGCCTCGTTGCCATT
        140    150         160            170      180
          *      *           *              *        *
   GGCCAGCGCCACGCC  GATATCACCCGCCAT   GGCGCCGGAGAGCGC
              190           200       210         220
               *             *         *           *
   CAGCAGACCGGCGGC  CAGCGGCGCATTCTC   AACGCCGGGCTCGTC
        230    240         250            260      270
          *      *           *              *        *
   GAACCATTCGGGGGC  GATTTCCGCACGACC   GCGATGCTGGTTGGA
              280           290       300         310
               *             *         *           *
   GAGCCAGGCCCTGGC  CAGCAACTGGCACAG   GTTCAGGTAACCCTG
        320    330         340            350      360
          *      *           *              *        *
   CTTGTCCCGCACCAA  CAGCAGCAGGCGGGT   CGGCTTGTCGCGCTC
              370           380       390         400
               *             *         *           *
   GTCGTGATTGGTGAT  CCACACGTCAGCCCC   GACGATGGGCTTCAC
        410    420         430            440      450
          *      *           *              *        *
   GCCCTTGCCACGCGC  TTCCTTGTAGANGCG   CACCAGCCCGAAGGC
              460           470       480         490
               *             *         *           *
   ATTGGCGAGATCGGT  CAGCGCCAAGGCGCC   CATGCCATCTTTGGC
        500    510         520            530      540
          *      *           *              *        *
   GGCAGCCTTGACGGC  ATCGTCGAGACGGAC   ATTGCCATCGACGAC
              550           560       570         580
               *             *         *           *
   GGAATATTCGGAGTG  GAGACGGAGGTGGAC   GAAGCGCGGCGAATT
        590    600         610            620      630
          *      *           *              *        *
   CATCCGCGTATTGTA  ACGGGTGACACCTTC   CGCAAAGCATTCCGG
              640           650       660         670
               *             *         *           *
   ACGTGCCCGATTGAC  CCGGAGCAACCCCGC   ACGGCTGCGCGGGCA
        680    690         700            710      720
          *      *           *              *        *
   GTTATAATTTCGGCT  TACGAATCAACGGGT   TACCCCAGGGCGCTG
              730           740
               *             *
   AAGCCTATCGCGTGC  AGTTGCCGGATGC
```

SEQ ID NO 12

FIG. 13B

FIG. 13D

SEQ ID NO 12

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
        ( A ) LENGTH: 1158 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 1:

```
CCCTTTGCCA  CTACATCAAT  TTAGGAGTA  AGGAAACCCA  ACGGACAGTG  GAGGTTAGTG        60

CAAGAACTCA  GGATTATCAA  TGAGGCTGTT  GTTCCTCTAT  ACCCAGCTGT  ACCTAACCCT      120
```

| TATACAGTGC | TTTCCCAAAT | ACCAGAGGAA | GCAGAGTGGT | TTACAGTCCT | GGACCTTAAG | 180 |
| GATGCCTTTT | TCTGCATCCC | TGTACGTCCT | GACTCTCAAT | TCTTGTTTGC | CTTTGAAGAT | 240 |
| CCTTTGAACC | CAACGTCTCA | ACTCACCTGG | ACTGTTTTAC | CCCAAGGGTT | CAGGGATAGC | 300 |
| CCCCATCTAT | TTGGCCAGGC | ATTAGCCCAA | GACTTGAGTC | AATTCTCATA | CCTGGACACT | 360 |
| CTTGTCCTTC | AGTACATGGA | TGATTTACTT | TTAGTCGCCC | GTTCAGAAAC | CTTGTGCCAT | 420 |
| CAAGCCACCC | AAGAACTCTT | AACTTTCCTC | ACTACCTGTG | GCTACAAGGT | TTCCAAACCA | 480 |
| AAGGCTCGGC | TCTGCTCACA | GGAGATTAGA | TACTNAGGGC | TAAAATTATC | CAAAGGCACC | 540 |
| AGGGCCCTCA | GTGAGGAACG | TATCCAGCCT | ATACTGGCTT | ATCCTCATCC | CAAAACCCTA | 600 |
| AAGCAACTAA | GAGGGTTCCT | TGGCATAACA | GGTTTCTGCC | GAAAACAGAT | TCCCAGGTAC | 660 |
| ASCCCAATAG | CCAGACCATT | ATATACACTA | ATTANGGAAA | CTCAGAAAGC | CAATACCTAT | 720 |
| TTAGTAAGAT | GGACACCTAC | AGAAGTGGCT | TTCCAGGCCC | TAAAGAAGGC | CCTAACCCAA | 780 |
| GCCCCAGTGT | TCAGCTTGCC | AACAGGGCAA | GATTTTTCTT | TATATGCCAC | AGAAAAAACA | 840 |
| GGAATAGCTC | TAGGAGTCCT | TACGCAGGTC | TCAGGGATGA | GCTTGCAACC | CGTGGTATAC | 900 |
| CTGAGTAAGG | AAATTGATGT | AGTGGCAAAG | GGTTGGCCTC | ATNGTTATG | GGTAATGGNG | 960 |
| GCAGTAGCAG | TCTNAGTATC | TGAAGCAGTT | AAAATAATAC | AGGGAAGAGA | TCTTNCTGTG | 1020 |
| TGGACATCTC | ATGATGTGAA | CGGCATACTC | ACTGCTAAAG | GAGACTTGTG | GTTGTCAGAC | 1080 |
| AACCATTTAC | TTAANTATCA | GGCTCTATTA | CTTGAAGAGC | CAGTGCTGNG | ACTGCGCACT | 1140 |
| TGTGCAACTC | TTAAACCC | | | | | 1158 |

(2) INFORMATION FOR SEQ ID NO: 2:

(i) SEQUENCE CHARACTERISTICS:
        (A) LENGTH: 297 bases
        (B) TYPE: nucleotide
        (C) STRANDEDNESS: single-stranded
        (D) TOPOLOGY: linear (ii) MOLECULE TYPE: cDNA (xi) SEQUENCE DESCRIPTION: SEQ ID NO: 2:

| CCCTTTGCCA | CTACATCAAT | TTAGGAGTA | AGGAAACCCA | ACGGACAGTG | GAGGTTAGTG | 60 |
| CAAGAACTCA | GGATTATCAA | TGAGGCTGTT | GTTCCTCTAT | ACCCAGCTGT | ACCTAACCCT | 120 |
| TATACAGTGC | TTTCCCAAAT | ACCAGAGGAA | GCAGAGTGGT | TTACAGTCCT | GGACCTTAAG | 180 |
| GATGCCTTTT | TCTGCATCCC | TGTACGTCCT | GACTCTCAAT | TCTTGTTTGC | CTTTGAAGAT | 240 |
| CCTTTGAACC | CAACGTCTCA | ACTCACCTGG | ACTGTTTTAC | CCCAAGGGTT | CAAGGGA | 297 |

(2) INFORMATION FOR SEQ ID NO: 3:

(i) SEQUENCE CHARACTERISTICS:
        (A) LENGTH: 85 bases
        (B) TYPE: nucleotide
        (C) STRANDEDNESS: single-stranded
        (D) TOPOLOGY: linear (ii) MOLECULE TYPE: cDNA (xi) SEQUENCE DESCRIPTION: SEQ ID NO: 3:

| GTTTAGGGAT | ANCCCTCATC | TCTTTGGTCA | GGTACTGGCC | CAAGATCTAG | GCCACTTCTC | 60 |
| AGGTCCAGSN | ACTCTGTYCC | TTCAG | | | | 85 |

(2) INFORMATION FOR SEQ ID NO: 4:

(i) SEQUENCE CHARACTERISTICS:

(A) LENGTH: 86 bases
(B) TYPE: nucleotide
(C) STRANDEDNESS: single-stranded
(D) TOPOLOGY: linear (ii) MOLECULE TYPE: cDNA (xi) SEQUENCE DESCRIPTION: SEQ ID NO: 4:

GTTCAGGGAT AGCCCCCATC TATTTGGCCA GGCACTAGCT CAATACTTGA GCCAGTTCTC    60

ATACCTGGAC AYTCTYGTCC TTCGGT    86

(2) INFORMATION FOR SEQ ID NO: 5:

(i) SEQUENCE CHARACTERISTICS:
(A) LENGTH: 85 bases
(B) TYPE: nucleotide
(C) STRANDEDNESS: single-stranded
(D) TOPOLOGY: linear (ii) MOLECULE TYPE: cDNA (xi) SEQUENCE DESCRIPTION: SEQ ID NO: 5:

GTTCARRGAT AGCCCCCATC TATTTGGCCW RGYATTAGCC CAAGACTTGA GYCAATTCTC    60

ATACCTGGAC ACTCTTGTCC TTYRG    85

(2) INFORMATION FOR SEQ ID NO: 6:

(i) SEQUENCE CHARACTERISTICS:
(A) LENGTH: 85 bases
(B) TYPE: nucleotide
(C) STRANDEDNESS: single-stranded
(D) TOPOLOGY: linear (ii) MOLECULE TYPE: cDNA (xi) SEQUENCE DESCRIPTION: SEQ ID NO: 6:

GTTCAGGGAT AGCTCCCATC TATTTGGCCT GGCATTAACC CGAGACTTAA GCCAGTTCTY    60

ATACGTGGAC ACTCTTGTCC TTTGG    85

(2) INFORMATION FOR SEQ ID NO: 7:

(i) SEQUENCE CHARACTERISTICS:
(A) LENGTH: 111 bases
(B) TYPE: nucleotide
(C) STRANDEDNESS: single-stranded
(D) TOPOLOGY: linear (ii) MOLECULE TYPE: cDNA (xi) SEQUENCE DESCRIPTION: SEQ ID NO: 7:

GTGTTGCCAC AGGGGTTTAR RGATANCYCY CATCTMTTTG GYCWRGYAYT RRCYCRAKAY    60

YTRRGYCAVT TCTYAKRYSY RGSNAYTCTB KYCCTTYRGT ACATGGATGA C    111

(2) INFORMATION FOR SEQ ID NO: 8:

(i) SEQUENCE CHARACTERISTICS:
(A) LENGTH: 645 bases
(B) TYPE: nucleotide
(C) STRANDEDNESS: single-stranded
(D) TOPOLOGY: linear (ii) MOLECULE TYPE: cDNA (xi) SEQUENCE DESCRIPTION: SEQ ID NO: 8:

TCAGGGATAG CCCCCATCTA TTTGGCCAGG CATTAGCCCA AGACTTGAGT CAATTCTCAT    60

ACCTGGACAC TCTTGTCCTT CAGTACATGG ATGATTTACT TTAGTCGCC CGTTCAGAAA   120

```
CCTTGTGCCA  TCAAGCCACC  CAAGAACTCT  TAACTTTCCT  CACTACCTGT  GGCTACAAGG    180

TTTCCAAACC  AAAGGCTCGG  CTCTGCTCAC  AGGAGATTAG  ATACTNAGGG  CTAAAATTAT    240

CCAAAGGCAC  CAGGGCCCTC  AGTGAGGAAC  GTATCCAGCC  TATACTGGCT  TATCCTCATC    300

CCAAAACCCT  AAAGCAACTA  AGAGGGTTCC  TTGGCATAAC  AGGTTTCTGC  CGAAAACAGA    360

TTCCCAGGTA  CASCCCAATA  GCCAGACCAT  TATATACACT  AATTANGGAA  ACTCAGAAAG    420

CCAATACCTA  TTTAGTAAGA  TGGACACCTA  CAGAAGTGGC  TTTCCAGGCC  CTAAAGAAGG    480

CCCTAACCCA  AGCCCCAGTG  TTCAGCTTGC  CAACAGGGCA  AGATTTTCT  TTATATGCCA    540

CAGAAAAAAC  AGGAATAGCT  CTAGGAGTCC  TTACGCAGGT  CTCAGGGATG  AGCTTGCAAC    600

CCGTGGTATA  CCTGAGTAAG  GAAATTGATG  TAGTGGCAAA  GGGTT                    645
```

(2) INFORMATION FOR SEQ ID NO: 9:

(i) SEQUENCE CHARACTERISTICS:
        (A) LENGTH: 741 bases
        (B) TYPE: nucleotide
        (C) STRANDEDNESS: single-stranded
        (D) TOPOLOGY: linear (ii) MOLECULE TYPE: cDNA (xi) SEQUENCE DESCRIPTION: SEQ ID NO: 9:

```
CAAGCCACCC  AAGAACTCTT  AAATTTCCTC  ACTACCTGTG  GCTACAAGGT  TTCCAAACCA     60

AAGGCTCAGC  TCTGCTCACA  GGAGATTAGA  TACTTAGGGT  TAAAATTATC  CAAAGGCACC    120

AGGGGCCTCA  GTGAGGAACG  TATCCAGCCT  ATACTGGGTT  ATCCTCATCC  CAAAACCCTA    180

AAGCAACTAA  GAGGGTTCCT  TAGCATGATC  AGGTTTCTGC  CGAAAACAAG  ATTCCCAGGT    240

ACAACCAAAA  TAGCCAGACC  ATTATATACA  CTAATTAAGG  AAACTCAGAA  AGCCAATACC    300

TATTTAGTAA  GATGGACACC  TAAACAGAAG  GCTTTCCAGG  CCCTAAAGAA  GGCCCTAACC    360

CAAGCCCCAG  TGTTCAGCTT  GCCAACAGGG  CAAGATTTTT  CTTTATATGG  CACAGAAAAA    420

ACAGGAATCG  CTCTAGGAGT  CCTTACACAG  GTCCGAGGGA  TGAGCTTGCA  ACCCGTGGCA    480

TACCTGAATA  AGGAAATTGA  TGTAGTGGCA  AAGGGTTGGC  CTCATNGTTT  ATGGGTAATG    540

GNGGCAGTAG  CAGTCTNAGT  ATCTGAAGCA  GTTAAAATAA  TACAGGGAAG  AGATCTTNCT    600

GTGTGGACAT  CTCATGATGT  GAACGGCATA  CTCACTGCTA  AAGGAGACTT  GTGGTTGTCA    660

GACAACCATT  TACTTAANTA  TCAGGCTCTA  TTACTTGAAG  AGCCAGTGCT  GNGACTGCGC    720

ACTTGTGCAA  CTCTTAAACC  C                                                 741
```

(2) INFORMATION FOR SEQ ID NO: 10:

(i) SEQUENCE CHARACTERISTICS:
        (A) LENGTH: 93 bases
        (B) TYPE: nucleotide
        (C) STRANDEDNESS: single-stranded
        (D) TOPOLOGY: linear (ii) MOLECULE TYPE: cDNA (xi) SEQUENCE DESCRIPTION: SEQ ID NO: 10:

```
TGGAAAGTGT  TGCCACAGGG  CGCTGAAGCC  TATCGCGTGC  AGTTGCCGGA  TGCCGCCTAT     60

AGCCTCTACA  TGGATGACAT  CCTGCTGGCC  TCC                                    93
```

(2) INFORMATION FOR SEQ ID NO: 11:

(i) SEQUENCE CHARACTERISTICS:
        (A) LENGTH: 96 bases (B) TYPE: nucleotide
(C) STRANDEDNESS: single-stranded
(D) TOPOLOGY: linear (i i) MOLECULE TYPE: cDNA (x i) SEQUENCE DESCRIPTION: SEQ ID NO: 11:

```
TTGGATCCAG TGYTGCCACA GGGCGCTGAA GCCTATCGCG TGCAGTTGCC GGATGCCGCC    60
TATAGCCTCT ACGTGGATGA CCTSCTGAAG CTTGAG                              96
```

(2) INFORMATION FOR SEQ ID NO: 12:

(i) SEQUENCE CHARACTERISTICS:
      (A) LENGTH: 748 bases
      (B) TYPE: nucleotide
      (C) STRANDEDNESS: single-stranded
      (D) TOPOLOGY: linear (i i) MOLECULE TYPE: cDNA (x i) SEQUENCE DESCRIPTION: SEQ ID NO: 12:

```
TGCAAGCTTC ACCGCTTGCT GGATGTAGGC CTCAGTACCG GNGTGCCCCG CGCGCTGTAG    60
TTCGATGTAG AAAGCGCCCG GAAACACGCG GGACCAATGC GTCGCCAGCT TGCGCGCCAG   120
CGCCTCGTTG CCATTGGCCA GCGCCACGCC GATATCACCC GCCATGGCGC CGGAGAGCGC   180
CAGCAGACCG GCGGCCAGCG GCGCATTCTC AACGCCGGGC TCGTCGAACC ATTCGGGGGC   240
GATTTCCGCA CGACCGCGAT GCTGGTTGGA GAGCCAGGCC CTGGCCAGCA ACTGGCACAG   300
GTTCAGGTAA CCCTGCTTGT CCCGCACCAA CAGCAGCAGG CGGGTCGGCT TGTCGCGCTC   360
GTCGTGATTG GTGATCCACA CGTCAGCCCC GACGATGGGC TTCACGCCCT TGCCACGCGC   420
TTCCTTGTAG ANGCGCACCA GCCCGAAGGC ATTGGCGAGA TCGGTCAGCG CCAAGGCGCC   480
CATGCCATCT TTGGCGGCAG CCTTGACGGC ATCGTCGAGA CGGACATTGC CATCGACGAC   540
GGAATATTCG GAGTGGAGAC GGAGGTGGAC GAAGCGCGGC GAATTCATCC GCGTATTGTA   600
ACGGGTGACA CCTTCCGCAA AGCATTCCGG ACGTGCCCGA TTGACCCGGA GCAACCCCGC   660
ACGGCTGCGC GGGCAGTTAT AATTTCGGCT TACGAATCAA CGGGTTACCC CAGGGCGCTG   720
AAGCCTATCG CGTGCAGTTG CCGGATGC                                      748
```

(2) INFORMATION FOR SEQ ID NO: 13:

(i) SEQUENCE CHARACTERISTICS:
      (A) LENGTH: 18 bases
      (B) TYPE: nucleotide
      (C) STRANDEDNESS: single-stranded
      (D) TOPOLOGY: linear (i i) MOLECULE TYPE: cDNA (x i) SEQUENCE DESCRIPTION: SEQ ID NO: 13:

```
GCATCCGGCA ACTGCACG                                                  18
```

(2) INFORMATION FOR SEQ ID NO: 14:

(i) SEQUENCE CHARACTERISTICS:
      (A) LENGTH: 20 bases
      (B) TYPE: nucleotide
      (C) STRANDEDNESS: single-stranded
      (D) TOPOLOGY: linear (i i) MOLECULE TYPE: cDNA (x i) SEQUENCE DESCRIPTION: SEQ ID NO: 14:

```
GTAGTTCGAT GTAGAAAGCG                                                20
```

( 2 ) INFORMATION FOR SEQ ID NO: 15:

( i ) SEQUENCE CHARACTERISTICS:
        ( A ) LENGTH: 18 bases
        ( B ) TYPE: nucleotide
        ( C ) STRANDEDNESS: single-stranded
        ( D ) TOPOLOGY: linear ( i i ) MOLECULE TYPE: cDNA ( x i ) SEQUENCE DESCRIPTION: SEQ ID NO: 15:

GCATCCGGCA ACTGCACG                                                18

( 2 ) INFORMATION FOR SEQ ID NO: 16:

( i ) SEQUENCE CHARACTERISTICS:
        ( A ) LENGTH: 23 bases
        ( B ) TYPE: nucleotide
        ( C ) STRANDEDNESS: single-stranded
        ( D ) TOPOLOGY: linear ( i i ) MOLECULE TYPE: cDNA ( x i ) SEQUENCE DESCRIPTION: SEQ ID NO: 16:

AGGAGTAAGG AAACCCAACG GAC                                   23

( 2 ) INFORMATION FOR SEQ ID NO: 17:

( i ) SEQUENCE CHARACTERISTICS:
        ( A ) LENGTH: 19 bases
        ( B ) TYPE: nucleotide
        ( C ) STRANDEDNESS: single-stranded
        ( D ) TOPOLOGY: linear ( i i ) MOLECULE TYPE: cDNA ( x i ) SEQUENCE DESCRIPTION: SEQ ID NO: 17:

TAAGAGTTGC ACAAGTGCG                                              19

( 2 ) INFORMATION FOR SEQ ID NO: 18:

( i ) SEQUENCE CHARACTERISTICS:
        ( A ) LENGTH: 21 bases
        ( B ) TYPE: nucleotide
        ( C ) STRANDEDNESS: single-stranded
        ( D ) TOPOLOGY: linear ( i i ) MOLECULE TYPE: cDNA ( x i ) SEQUENCE DESCRIPTION: SEQ ID NO: 18:

TCAGGGATAG CCCCCATCTA T                                     21

( 2 ) INFORMATION FOR SEQ ID NO: 19:

( i ) SEQUENCE CHARACTERISTICS:
        ( A ) LENGTH: 24 bases
        ( B ) TYPE: nucleotide
        ( C ) STRANDEDNESS: single-stranded
        ( D ) TOPOLOGY: linear ( i i ) MOLECULE TYPE: cDNA ( x i ) SEQUENCE DESCRIPTION: SEQ ID NO: 19:

AACCCTTTGC CACTACATCA ATTT                                  24

( 2 ) INFORMATION FOR SEQ ID NO: 20:

( i ) SEQUENCE CHARACTERISTICS:

( A ) LENGTH: 15 bases
            ( B ) TYPE: nucleotide
            ( C ) STRANDEDNESS: single- stranded
            ( D ) TOPOLOGY: linear ( i i ) MOLECULE TYPE: cDNA ( i x ) FEATURE:
            ( B ) LOCATION: 5, 7, 10, 13
            ( D ) OTHER INFORMATION: G represents inosine (i)

( x i ) SEQUENCE DESCRIPTION: SEQ ID NO: 20:

GGTCGTGCCG CAGGG 15

( 2 ) INFORMATION FOR SEQ ID NO: 21:

( i ) SEQUENCE CHARACTERISTICS:
            ( A ) LENGTH: 21 bases
            ( B ) TYPE: nucleotide
            ( C ) STRANDEDNESS: single- stranded
            ( D ) TOPOLOGY: linear ( i i ) MOLECULE TYPE: cDNA ( x i ) SEQUENCE DESCRIPTION: SEQ ID NO: 21:

TTAGGGATAG CCCTCATCTC T 21

( 2 ) INFORMATION FOR SEQ ID NO: 22:

( i ) SEQUENCE CHARACTERISTICS:
            ( A ) LENGTH: 21 bases
            ( B ) TYPE: nucleotide
            ( C ) STRANDEDNESS: single- stranded
            ( D ) TOPOLOGY: linear ( i i ) MOLECULE TYPE: cDNA ( x i ) SEQUENCE DESCRIPTION: SEQ ID NO: 22:

TCAGGGATAG CCCCCATCTA T 21

( 2 ) INFORMATION FOR SEQ ID NO: 23:

( i ) SEQUENCE CHARACTERISTICS:
            ( A ) LENGTH: 24 bases
            ( B ) TYPE: nucleotide
            ( C ) STRANDEDNESS: single- stranded
            ( D ) TOPOLOGY: linear ( i i ) MOLECULE TYPE: cDNA ( x i ) SEQUENCE DESCRIPTION: SEQ ID NO: 23:

AACCCTTTGC CACTACATCA ATTT 24

( 2 ) INFORMATION FOR SEQ ID NO: 24:

( i ) SEQUENCE CHARACTERISTICS:
            ( A ) LENGTH: 23 bases
            ( B ) TYPE: nucleotide
            ( C ) STRANDEDNESS: single- stranded
            ( D ) TOPOLOGY: linear ( i i ) MOLECULE TYPE: cDNA ( x i ) SEQUENCE DESCRIPTION: SEQ ID NO: 24:

GCGTAAGGAC TCCTAGAGCT ATT 23

( 2 ) INFORMATION FOR SEQ ID NO: 25:

( i ) SEQUENCE CHARACTERISTICS:
            ( A ) LENGTH: 18 bases ( B ) TYPE: nucleotide
                ( C ) STRANDEDNESS: single- stranded
                ( D ) TOPOLOGY: linear ( i i ) MOLECULE TYPE: cDNA ( x i ) SEQUENCE DESCRIPTION: SEQ ID NO: 25:

TCATCCATGT ACCGAAGG         18

( 2 ) INFORMATION FOR SEQ ID NO: 26:

( i ) SEQUENCE CHARACTERISTICS:
                ( A ) LENGTH: 20 bases
                ( B ) TYPE: nucleotide
                ( C ) STRANDEDNESS: single- stranded
                ( D ) TOPOLOGY: linear ( i i ) MOLECULE TYPE: cDNA ( x i ) SEQUENCE DESCRIPTION: SEQ ID NO: 26:

ATGGGGTTCC CAAGTTCCCT         20

( 2 ) INFORMATION FOR SEQ ID NO: 27:

( i ) SEQUENCE CHARACTERISTICS:
                ( A ) LENGTH: 20 bases
                ( B ) TYPE: nucleotide
                ( C ) STRANDEDNESS: single- stranded
                ( D ) TOPOLOGY: linear ( i i ) MOLECULE TYPE: cDNA ( x i ) SEQUENCE DESCRIPTION: SEQ ID NO: 27:

GCCGATATCA CCCGCCATGG         20

( 2 ) INFORMATION FOR SEQ ID NO: 28:

( i ) SEQUENCE CHARACTERISTICS:
                ( A ) LENGTH: 18 bases
                ( B ) TYPE: nucleotide
                ( C ) STRANDEDNESS: single- stranded
                ( D ) TOPOLOGY: linear ( i i ) MOLECULE TYPE: cDNA ( x i ) SEQUENCE DESCRIPTION: SEQ ID NO: 28:

GCATCCGGCA ACTGCACG         18

( 2 ) INFORMATION FOR SEQ ID NO: 29:

( i ) SEQUENCE CHARACTERISTICS:
                ( A ) LENGTH: 20 bases
                ( B ) TYPE: nucleotide
                ( C ) STRANDEDNESS: single- stranded
                ( D ) TOPOLOGY: linear ( i i ) MOLECULE TYPE: cDNA ( x i ) SEQUENCE DESCRIPTION: SEQ ID NO: 29:

CGCGATGCTG GTTGGAGAGC         20

( 2 ) INFORMATION FOR SEQ ID NO: 30:

( i ) SEQUENCE CHARACTERISTICS:
                ( A ) LENGTH: 20 bases
                ( B ) TYPE: nucleotide
                ( C ) STRANDEDNESS: single- stranded
                ( D ) TOPOLOGY: linear ( i i ) MOLECULE TYPE: cDNA ( x i ) SEQUENCE DESCRIPTION: SEQ ID NO: 30:

TCTCCACTCC GAATATTCCG 20

( 2 ) INFORMATION FOR SEQ ID NO: 31:

( i ) SEQUENCE CHARACTERISTICS:
        ( A ) LENGTH: 26 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 31:

GATCTAGGCC ACTTCTCAGG TCCAGS 26

( 2 ) INFORMATION FOR SEQ ID NO: 32:

( i ) SEQUENCE CHARACTERISTICS:
        ( A ) LENGTH: 23 bases
        ( B ) TYPE: nucleotide
        ( C ) STRANDEDNESS: single- stranded
        ( D ) TOPOLOGY: linear ( i i ) MOLECULE TYPE: cDNA ( i x ) FEATURE:
        ( B ) LOCATION: 6, 12, 19
        ( D ) OTHER INFORMATION: G represents inosine (i)

( x i ) SEQUENCE DESCRIPTION: SEQ ID NO: 32:

CATCTGTTTG GGCAGGCAGT AGC 23

( 2 ) INFORMATION FOR SEQ ID NO: 33:

( i ) SEQUENCE CHARACTERISTICS:
        ( A ) LENGTH: 24 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 33:

CTTGAGCCAG TTCTCATACC TGGA 24

( 2 ) INFORMATION FOR SEQ ID NO: 34:

( i ) SEQUENCE CHARACTERISTICS:
        ( A ) LENGTH: 22 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 34:

AGTGYTRCCM CARGGCGCTG AA 22

( 2 ) INFORMATION FOR SEQ ID NO: 35:

( i ) SEQUENCE CHARACTERISTICS:
        ( A ) LENGTH: 22 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 35:

GMGGCCAGCA GSAKGTCATC CA 22

( 2 ) INFORMATION FOR SEQ ID NO: 36:

( i ) SEQUENCE CHARACTERISTICS:
        ( A ) LENGTH: 22 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 36:

GGATGCCGCC TATAGCCTCT AC 22

( 2 ) INFORMATION FOR SEQ ID NO: 37:

( i ) SEQUENCE CHARACTERISTICS:
        ( A ) LENGTH: 22 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 37:

AAGCCTATCG CGTGCAGTTG CC 22

( 2 ) INFORMATION FOR SEQ ID NO: 38:

( i ) SEQUENCE CHARACTERISTICS:
        ( A ) LENGTH: 40 bases
        ( B ) TYPE: nucleotide
        ( C ) STRANDEDNESS: single- stranded
        ( D ) TOPOLOGY: linear ( i i ) MOLECULE TYPE: cDNA ( x i ) SEQUENCE DESCRIPTION: SEQ ID NO: 38:

TAAAGATCTA GAATTCGGCT ATAGGCGGCA TCCGGCAAGT 40